United States Patent
Kamiya et al.

(10) Patent No.: US 9,688,777 B2
(45) Date of Patent: Jun. 27, 2017

(54) PROTEIN-POLYMER COMPLEX, TGASE SUBSTRATE-CONTAINING POLYMER, TGASE SUBSTRATE-CONTAINING MONOMER, METHOD FOR PRODUCING PROTEIN-POLYMER COMPLEX, AND METHOD FOR IMPROVING PROTEIN FUNCTION AT SOLID-LIQUID INTERFACE OR IN VICINITY OF SOLID-LIQUID INTERFACE

(71) Applicants: KYUSHU UNIVERSITY, NATIONAL UNIVERSITY CORPORATION, Fukuoka-shi, Fukuoka (JP); HITACHI ALOKA MEDICAL, LTD., Mitaka-shi, Tokyo (JP)

(72) Inventors: Noriho Kamiya, Fukuoka (JP); Rie Wakabayashi, Fukuoka (JP); Kensuke Yahiro, Fukuoka (JP); Kounosuke Hayashi, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/392,208

(22) PCT Filed: Jun. 27, 2014

(86) PCT No.: PCT/JP2014/067850
§ 371 (c)(1),
(2) Date: Dec. 23, 2015

(87) PCT Pub. No.: WO2014/208776
PCT Pub. Date: Dec. 31, 2014

(65) Prior Publication Data
US 2016/0251450 A1 Sep. 1, 2016

(30) Foreign Application Priority Data
Jun. 28, 2013 (JP) ................................. 2013-136878

(51) Int. Cl.
| C07K 17/08 | (2006.01) |
| C07K 14/00 | (2006.01) |
| G01N 33/68 | (2006.01) |
| C07K 5/062 | (2006.01) |
| C07K 14/315 | (2006.01) |
| C08G 61/12 | (2006.01) |
| C12N 9/42 | (2006.01) |
| C12N 9/96 | (2006.01) |
| G01N 33/543 | (2006.01) |

(52) U.S. Cl.
CPC .......... C07K 17/08 (2013.01); C07K 5/06034 (2013.01); C07K 14/00 (2013.01); C07K 14/315 (2013.01); C08G 61/128 (2013.01); C12N 9/2437 (2013.01); C12N 9/96 (2013.01); G01N 33/54306 (2013.01); G01N 33/68 (2013.01); C08G 2261/148 (2013.01); *C08G 2261/1426* (2013.01); *C08G 2261/1432* (2013.01); *C08G 2261/94* (2013.01); *C12Y 302/01004* (2013.01)

(58) Field of Classification Search
None
See application file for complete search history.

(56) References Cited

U.S. PATENT DOCUMENTS

| 5,543,332 A | 8/1996 | Lihme et al. |
| 6,013,526 A | 1/2000 | Takahara et al. |
| 6,252,053 B1 | 6/2001 | Ohbayashi et al. |
| 2001/0005583 A1 | 6/2001 | Ohbayashi et al. |
| 2004/0001892 A1 | 1/2004 | Healy et al. |
| 2011/0189671 A1 | 8/2011 | Kamiya et al. |

FOREIGN PATENT DOCUMENTS

| JP | 6-509167 A | 10/1994 |
| JP | 8-89278 A | 4/1996 |
| JP | 2000-88850 A | 3/2000 |
| JP | 2001-181299 A | 7/2001 |
| JP | 2008-54658 A | 3/2008 |
| JP | 2009-286701 A | 12/2009 |
| JP | 2010-47559 A | 3/2010 |
| WO | 2010/119583 A1 | 10/2010 |
| WO | 2011/014605 A1 | 2/2011 |
| WO | 2011/062965 A2 | 5/2011 |

OTHER PUBLICATIONS

Cuchiara, Michael P.; "Integration of self assembled microvascular networks with microfabricated peg-based hydrogels." Adv. Func. Mater. (2012) 22(21) p. 4511-4518.*
International Search Report dated Sep. 30, 2014, issued in counterpart application No. PCT/JP2014/067850 (2 pages).
Sugimura et al, "Novel site-specific immobilization of a functional protein using a preferred substrate sequence for transglutaminase 2", Journal of Biotechnology, 2007, vol. 131, pp. 121-127.
Spolaore, et al, "Local Unfolding Is Required for the Site-Specific Protein Modification by Transglutaminase", Biochemistry, 2012, vol. 51, pp. 8679-8689.
Fontana et al, "Site-specific modification and PEGylation of pharmaceutical proteins mediated by transglutaminase", Advanced Drug Delivecy Reviews, 2008, vol. 60, pp. 13-28.
Sato, "Enzymatic procedure for site-specific pegylation of proteins", Advanced Drug Delivery Reviews, 2002, vol. 54, pp. 487-504.

(Continued)

*Primary Examiner* — Fred Reynolds
(74) *Attorney, Agent, or Firm* — Westerman, Hattori, Daniels & Adrian, LLP

(57) ABSTRACT

Provided is a protein-polymer complex which is capable of detecting a target with good sensitivity. Specifically provided is a protein-polymer complex comprising a polymer having a glutamine (Gln) residue or a primary amine on a side chain, wherein either a protein having a primary amine is bound to the glutamine (Gln) residue, or a protein having a glutamine (Gln) residue is bound to the primary amine.

3 Claims, 22 Drawing Sheets

(56) References Cited

OTHER PUBLICATIONS

Sato et al., "Further Studies on the Site-Specific Protein Modification by Microbial Transglutaminase", Bioconjugate Chem., 2001, vol. 12, pp. 701-710.
Tanaka et al, "Exploring enzymatic catalysis at a solid surface: a case study with transglutaminase-mediated protein immobilization", Organic & Biomolecular Chemistry, 2007, vol. 5, pp. 1764-1770.
Notification of Transmittal of Translation of the International Preliminary Report on Patentability (Form/IB/338) with Form IPEA/409 issued in counterpart International Application No. PCT/P2014/067850 mailed Dec. 30, 2015. (5 pages).
Mitsuzawa et al., "The rosettazyme: A synthetic cellulosome," Journal of Biotechnology, vol. 143, 2009, pp. 139-144, Elsevier B.V.
Kim et al., "Enhancement of Cellulolytic Enzyme Activity by Clustering Cellulose Binding Domains on Nanoscaffolds," Small, vol. 7, No. 5, 2011, pp. 656-664, Wiley-VCH Verlag GmBH & Co. KGaA, Weinheim.
Extended European Search Report dated Dec. 8, 2016, issued in counterpart application No. 14816842.0 (7 pages).

* cited by examiner

[caTATG] : RESTRICTION ENZYME NdeI RECOGNITION SEQUENCE

[Ctcgag] : RESTRICTION ENZYME XhoI RECOGNITION SEQUENCE

[pET22 K-tag pG]

VECTOR-DERIVED SEQUENCE (LOWER CASE PORTION)
cgaaattaatacgactcactatagggggaattgtgagcggataacaatttgtt
taactttaagaaggagatata[caTATG]ACTTACATGATTACAAATTGGTCATTAAGGGGAAA B2 DOMAIN OF PROTEIN G
CCACCACTAAGGCGGTTGAGCGGGAAACGCCGAGAAGCGTTCAAGCAGTAGTGCTAAGGACAATGGTGT
TGATGGCGTGTGACCTATGGATGATGAAGAGCAGAGAACGCCTTCTGGGAGATTCTCCACCTCGGATT
GTCGACAATAAGTTCAATAAAGAGCAGAGAACGCCTTCTGGGAGATTCTCCACCTCGGATCTGAACG D DOMAIN OF PROTEIN A
AGGAGCAGGCGTAACGGTTAACGGGTTTTATTCAATCTCTGAAAGACGATCCGTCACAGAGCGCTAAGAGA
AGCAAAAAATTAAATGATGCCAGGCGCCGAAAGGCGGTGGGGATCCCTGGTTCCTCGTGGTTCTATG
AGACACAAAGGGTTCC[Ctcgag]baccaccaccaccactgagtccggctgctaacaaagcccgaaagg VECTOR-DERIVED SEQUENCE (LOWER CASE PORTION)
aagctgagttggctgctgccacgctgagcaataactagcataaccccttggggcctctaaacgggtctt

FIG. 12

PROTEIN-POLYMER COMPLEX, TGASE SUBSTRATE-CONTAINING POLYMER, TGASE SUBSTRATE-CONTAINING MONOMER, METHOD FOR PRODUCING PROTEIN-POLYMER COMPLEX, AND METHOD FOR IMPROVING PROTEIN FUNCTION AT SOLID-LIQUID INTERFACE OR IN VICINITY OF SOLID-LIQUID INTERFACE

TECHNICAL FIELD

The present invention relates to a protein-polymer complex, a TGase substrate-containing polymer, a TGase substrate-containing monomer, a method for producing a protein-polymer complex, a method for detecting a protein, an enzyme reaction method, and a method for improving protein function at, or in the vicinity of, a solid-liquid interface.

BACKGROUND ART

A variety of proteins exist in biological samples, and methods such as ELISA (Enzyme Linked ImmunoSorbent Assay) are known as methods for detecting and quantifying specific proteins.

ELISA is a method for quantitatively detecting a specific protein such as an antigen contained in a sample, by using an enzyme-labeled antibody and utilizing an antigen-antibody reaction, and is one technique that is widely used in immunological tests and the like. Known forms of ELISA include the direct adsorption method, the sandwich method and the competitive method.

For example, a primary antibody for a target substance (antigen) adsorbed to the surface of a solid phase is bound via an antigen-antibody reaction. The unreacted primary antibody is washed away, and an enzyme-labeled secondary antibody is then added and bound via a second antigen-antibody reaction. The unreacted labeled secondary antibody is then washed away, and when a chromogenic substrate is added, a color reaction occurs in proportion to the amount of the antigen. The absorbance of the thus generated colored material is measured using an absorbance meter or the like, and the amount of the antigen can be quantified by using a calibration curve prepared using standard samples of known concentration.

Further, methods using polymer antibodies and the like are also known as high-sensitivity antigen detection methods.

For example, Patent Document 1 discloses a method in which divinyl sulfone is reacted with a polymer such as dextran to introduce vinyl groups, and the resulting polymer is then reacted with an enzyme and an antibody to prepare a complex of the enzyme, the antibody and dextran.

Patent Document 2 discloses an enzyme-protein complex in which a peptide polymer having two or more basic amino groups or a polysaccharide having at least one introduced amino group, aldehyde group or vinyl group is used as a carrier, two or more enzymes are bound to the carrier, and a protein that exhibits specific binding affinity to another substance is then bound to at least one of the enzymes to form an enzyme-protein complex.

Patent Document 3 discloses an enzyme-antibody complex in which, using a peptide polymer having a multitude of basic amino groups or a polysaccharide having an introduced amino group as a carrier, one or more molecules of an enzyme having an introduced maleimide group or thiol group, and the carrier, into which either a thiol group has been introduced in the case where a maleimide group has been introduced into the enzyme, or a maleimide group has been introduced in the case where a thiol group has been introduced into the enzyme, are bound together covalently via these groups, a maleimide group is then introduced at the site of at least one residual amino group of the resulting complex, and a thiol group obtained by reduction of an antibody or antibody fragment is then covalently bound to the maleimide group of the complex.

However, in the enzyme-labeled secondary antibody described above or any of the polymer antibodies such as those described in Patent Documents 1 to 3, the enzyme labeling is introduced via a chemical binding method, and therefore the active center of the enzyme is modified, and there is a possibility that the activity of the enzyme may deteriorate.

On the other hand, it has been found that by using an enzyme complex in which a plurality of enzymes have been complexed with the molecule or material that functions as the scaffold, the efficiency of the enzyme reactions can be improved compared with that of the stand-alone enzymes. For example, natural cellulolytic enzymes can efficiently degrade cellulose, which has a strong crystal structure, and therefore there is growing demand for these cellulolytic enzymes as catalysts for the production of biofuels and chemical products using cellulose-based biomass, which is a renewable resource, as a raw material. This process is particularly desirable if inedible biomass can be used, because then there is no competition with food production. Natural systems exist which form enzyme complexes known as cellulosomes that can efficiently degrade cellulose. Tests are now being conducted into the production of artificial cellulolytic enzyme complexes which resemble cellulosomes.

Non-Patent Document 1 discloses that by binding a variety of different cellulases to a polymeric protein that functions as a scaffold, the cellulolytic activity could be increased.

Non-Patent Document 2 discloses that by separating the cellulase catalytic domains and the cellulose-binding domains, and using metal nanoparticles as a scaffold, the cellulolytic activity could be increased by increasing the proportion of cellulose-binding domains.

However, complexes such as those described in Non-Patent Documents 1 and 2 use a three dimensional nanomaterial such as a large protein complex or metal nanoparticles as the scaffold, and do not use a flexible one-dimensional polymer material such as a synthetic polymer as the scaffold molecule.

On the other hand, another method is known in which a transglutaminase (TGase) is used to achieve site-specific binding of an exogenous molecule, which is anionic and has a glutamine (Gln) residue that is recognizable by TGase, to a peptide or protein having a lysine (Lys) residue or a primary amine that is recognizable by TGase (for example, see Patent Document 4).

PRIOR ART DOCUMENTS

Patent Documents

Patent Document 1: JP H06-509167 A
Patent Document 2: JP 2001-181299 A
Patent Document 3: JP 2000-088850 A
Patent Document 4: JP 2008-54658 A Non-Patent Documents Non-Patent Document 1: Shigenobu Mitsuzawa et al., J. Biotechnol., vol. 143, pp. 139 to 144 (2009)
Non-Patent Document 2: Do-Myoung Kim et al., small, vol. 7, pp. 656 to 664 (2011)

SUMMARY OF THE INVENTION

Problems to be Solved by the Invention

Objects of the present invention are to provide a protein-polymer complex which is capable of detecting a target protein with good sensitivity, or has an enzyme reaction efficiency that is improved beyond that of the stand-alone enzyme, and also to provide a TGase substrate-containing polymer and a TGase substrate-containing monomer that can be used for obtaining the protein-polymer complex, a method for producing the protein-polymer complex, a method for detecting a protein using the protein-polymer complex, an enzyme reaction method that uses the protein-polymer complex, and a method for improving protein function at, or in the vicinity of, a solid-liquid interface using the protein-polymer complex.

Means for Solving the Problems

The present invention provides a protein-polymer complex comprising a polymer having a glutamine (Gln) residue or a primary amine on a side chain, wherein either a protein having a primary amine is bound to the glutamine (Gln) residue, or a protein having a glutamine (Gln) residue is bound to the primary amine.

Further, the present invention also provides a TGase substrate-containing polymer having a glutamine (Gln) residue or a lysine (Lys) residue on a side chain.

Furthermore, the present invention also provides a TGase substrate-containing monomer having a glutamine (Gln) residue or a lysine (Lys) residue that can be used in the production of a polymer having a glutamine (Gln) residue or a lysine (Lys) residue on a side chain.

Moreover, the present invention also provides a method for producing a protein-polymer complex, the method comprising a protein binding step of using a transglutaminase (TGase) to bind, to a polymer having a glutamine (Gln) residue or a primary amine on a side chain, either a protein having a primary amine to the glutamine (Gln) residue, or a protein having a glutamine (Gln) residue to the primary amine.

Further, the present invention also provides a method for detecting a protein, the method comprising binding, either directly or indirectly, a protein-polymer complex comprising a polymer having a glutamine (Gln) residue or a primary amine on a side chain, wherein either a protein having a primary amine is bound to the glutamine (Gln) residue or a protein having a glutamine (Gln) residue is bound to the primary amine, and a target protein that exists within a target material, binding a labeling molecule comprising a portion that binds specifically to the protein of the bound protein-polymer complex, and detecting the labeling molecule.

Furthermore, the present invention also provides an enzyme reaction method, wherein a protein-polymer complex, which comprises a polymer having a glutamine (Gln) residue or a primary amine on a side chain, in which either a protein having a primary amine is bound to the glutamine (Gln) residue or a protein having a glutamine (Gln) residue is bound to the primary amine, and in which the protein is an enzyme, acts upon a substrate.

Further, the present invention also provides a method for improving protein function at, or in the vicinity of, a solid-liquid interface, the method using a protein-polymer complex comprising a polymer having a glutamine (Gln) residue or a primary amine on a side chain, wherein either a protein having a primary amine is bound to the glutamine (Gln) residue, or a protein having a glutamine (Gln) residue is bound to the primary amine.

Advantages of the Invention

The present invention is able to provide a protein-polymer complex which is capable of detecting a target protein with good sensitivity, or has an enzyme reaction efficiency that is improved beyond that of the stand-alone enzyme, and also provide a TGase substrate-containing polymer and a TGase substrate-containing monomer that can be used for obtaining the protein-polymer complex, a method for producing the protein-polymer complex, a method for detecting a protein using the protein-polymer complex, an enzyme reaction method that uses the protein-polymer complex, and a method for improving protein function at, or in the vicinity of, a solid-liquid interface using the protein-polymer complex.

BRIEF DESCRIPTION OF THE DRAWINGS

FIG. 12 is a diagram illustrating the gene sequence of a vector used in an example.

EMBODIMENTS FOR CARRYING OUT THE INVENTION

Embodiments of the present invention are described below. These embodiments are merely examples of implementing the present invention, and the present invention is in no way limited by these embodiments.

In order to achieve one-dimensional accumulation of a protein on a polymer, investigations were conducted into the cross-linking of a polymer having an MTG-recognizable Gln residue or an MTG-recognizable primary amine on a side chain, and a protein having an MTG-recognizable Lys peptide tag or an MTG-recognizable Gln peptide tag.

The inventors of the present invention focused their attention on the site-specific protein-modifying ability possessed by transglutaminases (TGase) such as microbial transglutaminase (MTG), as a technique for introducing a protein into a polymer via covalent binding. TGase is an enzyme that catalyzes transacylation reactions, and for example, catalyzes covalent binding between the γ-carboxamide group of specific Gln residues (Q) within a protein, and the ε-amino group of a lysine residue (K) or any of various primary amines. Using this TGase, protein-polymer complexes containing an introduced protein such as an enzyme can be created. Because MTG or the like exhibits high substrate recognition, the reactive site of the polymer and the reactive tag portion of the enzyme or the like can be cross-linked selectively, enabling the enzyme or the like to be introduced with almost no reduction in activity. Further, because a polymer is used as the scaffold molecule, there are various advantages compared with the case where a nucleic acid such as DNA is used as the scaffold molecule, including higher chemical stability, ability to control the chemical properties via the combination of comonomers, as well as cost advantages. If an atom transfer radical polymerization method (ATRP) described below or similar is used in addition to conventional polymerization methods, then the degree of polymerization and the like can be controlled.

For example, by synthesizing a monomer that includes, as an MTG-recognizable Gln, an N-carbobenzyloxy glutaminyl glycine (Z-QG) (namely, a Z-QG-containing monomer), which is a Gln substrate that is widely used for measuring MTG activity, and then either polymerizing the monomer, or if necessary copolymerizing the monomer with a comonomer, the inventors investigated the production of Z-QG-containing polymers. It is thought that by varying the composition ratio between the Z-QG-containing monomer and the comonomer, it is possible to control the distance between Z-QG sites to a distance that is appropriate for substrate recognition in the MTG reaction, and to control the distance between proteins following accumulation.

Figure 1:
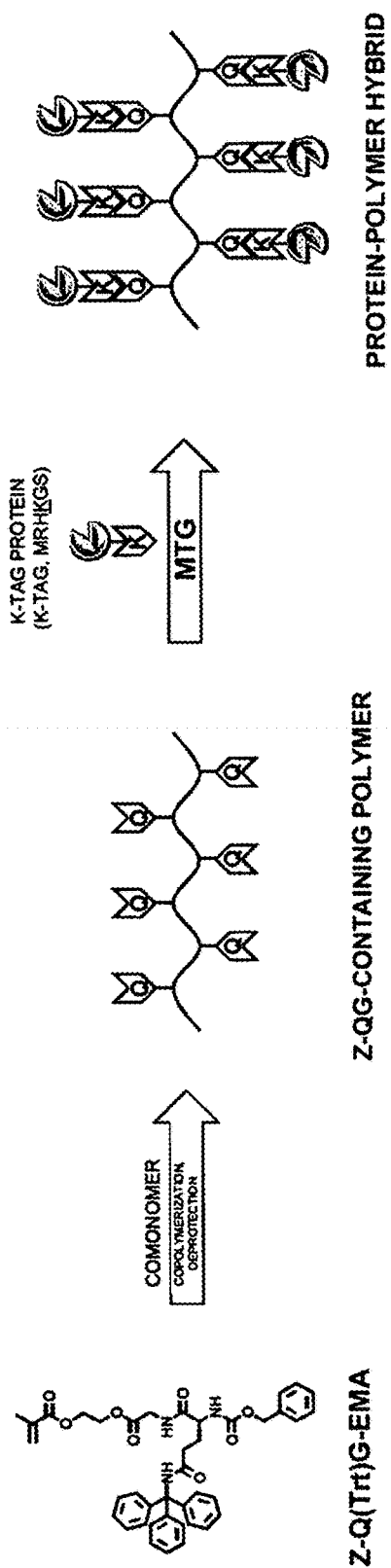
FIG. 1 is a schematic view illustrating one example of a method for producing a protein-polymer complex according to an embodiment of the present invention.

Specifically, as illustrated by the example in FIG. 1, by synthesizing a monomer Z-Q(Trt)G-EMA, which is a TGase substrate-containing monomer containing Z-QG having a Gln that is recognizable by TGase (MTG-recognizable Gln), and then either polymerizing this monomer, or if necessary copolymerizing the monomer with a comonomer, a Z-QG-containing polymer is obtained which is a TGase substrate-containing polymer that also contains Z-QG. Subsequently, by using a TGase such as MTG to achieve binding of a protein such as an enzyme having an introduced TGase-recognizable Lys such as MTG-recognizable Lys, a protein-polymer complex having a polymer:protein ratio of 1:n (wherein n is an integer of 1 or greater) can be produced.

If this protein-polymer complex is bound to a target protein, and a labeling enzyme containing a labeling portion is then bound to the protein of the bound protein-polymer complex, then a detection reaction for the target protein can be performed. Further, if a labeling enzyme containing a labeling portion is bound to the protein of the protein-polymer complex, and a target protein is then bound, then a detection reaction for the target protein can be performed. As a result, operations can be simplified considerably and the background can be reduced compared with conventional techniques, and because the bulk enzyme microbial transglutaminase (MTG) is used, cost reductions and the like can also be expected. Further, this protein-polymer complex can also be utilized in cascade enzyme reaction systems and enzyme reaction systems which degrade substrates concertedly.

In FIG. 1, the Gln residue in the TGase substrate-containing monomer such as Z-Q(Trt)G-EMA and the TGase substrate-containing polymer, and the primary amine such as the Lys residue in the protein may be reversed. In other words, by synthesizing a TGase substrate-containing monomer having a Lys or the like that is recognizable by TGase (MTG-recognizable Lys), and then either polymerizing this monomer, or if necessary copolymerizing the monomer with a comonomer, a TGase substrate-containing polymer having a Lys (MTG-recognizable Lys) or the like is obtained.

Subsequently, by using a TGase such as MTG to achieve binding of a protein such as an enzyme having an introduced TGase-recognizable Gln such as MTG-recognizable Gln, a protein-polymer complex having a polymer:protein ratio of 1:n (wherein n is an integer of 1 or greater) can be produced.

In this manner, any effects on the active site of the protein such as an enzyme can be suppressed, enabling the protein to be introduced into the polymer in a site-specific manner.

In the present description, a "polymer" is a large organic molecule which has a structure composed of repeating monomer units, has a backbone composed mainly of carbon-carbon bonds, is formed from carbon, hydrogen and nitrogen atoms and the like, and has a weight-average molecular weight of at least 10,000, and as such, differs from biopolymers such as proteins and nucleic acids.

The TGase substrate-containing monomer according to an embodiment of the present invention is a monomer having a glutamine (Gln) residue or a lysine (Lys) residue that can be used in the production of a polymer having a glutamine (Gln) residue or a lysine (Lys) residue on a side chain. There are no particular limitations on the TGase substrate-containing monomer having a glutamine (Gln) residue or a lysine (Lys) residue, provided the monomer has a glutamine (Gln) residue or a lysine (Lys) residue, and can be used to obtain a polymer via a polymerization reaction. Examples of the monomer include a methacrylate ester, acrylate ester, methacrylamide, acrylamide or styrene derivative having a glutamine (Gln) residue or a lysine (Lys) residue. Among these, in terms of reactivity, ease of synthesis, and ease of synthesis in terms of applicability to the atom transfer radical polymerization method (ATRP) described below, an acrylate ester or methacrylate ester having a glutamine (Gln) residue or a lysine (Lys) residue is preferred.

Examples of acrylate esters or methacrylate esters having a glutamine (Gln) residue include the compounds of formula (1) shown below.

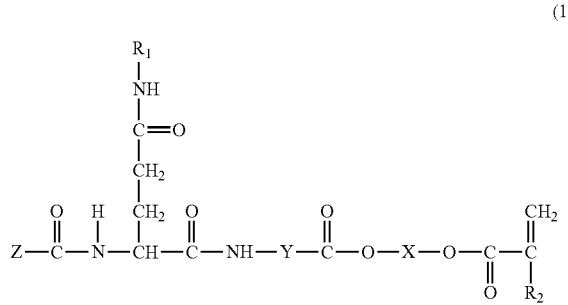

(1)

In formula (1), $R_1$ represents a hydrogen atom or a protective group, $R_2$ represents a hydrogen atom or a methyl group, each of X and Y independently represents an alkylene group having a carbon number of 1 to 48 or an alkenylene group having a carbon number of 2 to 48, and Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48.

Specific examples of the divalent groups represented by X and Y include, independently, alkylene groups having a carbon number of 1 to 48 such as a methylene group, ethylene group, propylene group or butylene group, and alkenylene groups having a carbon number of 2 to 48 such as an ethenylene group, propenylene group or butenylene group. Among these, each of X and Y preferably independently represents an alkylene group having a carbon number of 1 to 48, and more preferably represents an alkylene group having a carbon number of 1 to 4, and compounds in which X represents an ethylene group and Y represents a methylene group are particularly preferred. X may be further substituted with an ethenylene group or an oxyalkylene group such as $—(C_2H_4O)_n—$ or $—(C_3H_6O)_n—$ (wherein n represents the number of repeating units, and n=2, 4, 8, 12 or 24). A specific example of this type of X group is $—(C_2H_4O)_n—C_2H_4—$.

Examples of the substituent represented by Z include alkyl groups having a carbon number of 1 to 48 such as a methyl group, ethyl group or propyl group, alkoxy groups having a carbon number of 1 to 48 such as a methoxy group, ethoxy group or propoxy group, aryl groups having a carbon number of 6 to 48 such as a phenyl group or naphthyl group, aryloxy groups having a carbon number of 6 to 48 such as a phenyloxy group, arylalkyl groups having a carbon number of 7 to 48 such as a benzyl group, and arylalkyloxy groups having a carbon number of 7 to 48 such as a benzyloxy group. Among these, Z is preferably an arylalkyloxy group having a carbon number of 7 to 48, more preferably an arylalkyloxy group having a carbon number of 7 to 10, and Z is most preferably a benzyloxy group. Z may be further substituted with a dinitrophenyl group or L-3,4-dihydroxyphenyl group or the like. Further, in the combination with the aforementioned substituent represented by Y, at least one of Y and Z may be independently substituted with an amino acid other than Lys.

By appropriate selection of X and Y, the structure of the linker region that links the Z-QG and the polymer can be optimized, so that, for example, by introducing a flexible linker region, the reactivity of the MTG reaction that causes cross-linking between the polymer and the protein can be improved.

In the TGase substrate-containing monomer of the above formula (1), if $R_1$ is a hydrogen atom, then when polymerization is performed by atom transfer radical polymerization or the like, there is a possibility that the amino group of the Gln side chain may act as a ligand, and therefore $R_1$ is preferably protected with a protective group that exhibits significant steric hindrance.

Examples of the protective group include a trityl group, 4-methyltrityl group, 4-methoxytrityl group, 2,4,6-trimethoxybenzyl group, 1-cyclopropyl-1-methylethyl group, and dicyclopropylmethyl group.

In those cases where microbial TGase (MTG) is used, the MTG-recognizable Gln residue preferably exists as benzyloxycarbonyl-L-glutamylglycine (Z-QG), as illustrated in the TGase substrate-containing monomer of the above formula (1). Z-QG is preferable as it has a smaller molecular size than digoxigenin (DIG) or the like. In the TGase substrate-containing monomer represented by formula (1), the TGase substrate-containing monomer in which $R_1$ represents a trityl group, $R_2$ represents a methyl group, X represents an ethylene group, Y represents a methylene group, and Z represents a benzyloxy group is Z-Q(Trt)G-EMA, and the TGase substrate-containing monomer in which $R_1$ represents a hydrogen atom, $R_2$ represents a methyl group, X represents an ethylene group, Y represents a methylene group, and Z represents a benzyloxy group is Z-QG-EMA. Further, selection of a TGase substrate-containing monomer that does not contain both a TGase-recognizable Gln residue and a Lys residue or primary amine is preferred. This is because if the monomer contains both types of residue, then self cross-linking may occur, which has an adverse effect on the yield of the targeted protein-polymer complex.

There are no particular limitations on the comonomer that may be copolymerized with the TGase substrate-containing monomer, and examples include vinyl monomers such as methacrylic acid, acrylic acid, methacrylate esters, acrylate esters, methacrylamide, acrylamide, styrene, acrylonitrile and vinyl acetate. For example, in order to ensure adequate hydrophilicity relative to the comparatively hydrophobic Z-QG, the use of an acrylate ester or a methacrylate ester as a comonomer is preferable. Either a single comonomer or two or more comonomers may be used.

Further, other examples of comonomers that may be copolymerized with the TGase substrate-containing monomer include monomers having a phosphorylcholine group such as 2-methacryloyloxyethyl phosphorylcholine.

The ratio between the TGase substrate-containing monomer and the comonomer may be set as appropriate, and for example, the ratio of TGase substrate-containing monomer: comonomer is typically within a range from 3 mol:1,000 mol to 1 mol:24 mol.

The TGase substrate-containing polymer according to an embodiment of the present invention is a polymer having a glutamine (Gln) residue or lysine (Lys) residue on a side chain. There are no particular limitations on the polymerization method used for obtaining the TGase substrate-containing polymer, and examples include radical polymerization using a peroxide or an azo compound, radical polymerization mediated via a nitroxide (NMP), reversible addition fragmentation chain transfer polymerization (RAFT), atom transfer radical polymerization (ATRP), condensation polymerization, ring-opening polymerization and ionic polymerization. Among these, the use of an atom transfer radical polymerization method (ATRP) is preferred. The atom transfer radical polymerization method is a living radical polymerization method that uses a transition metal complex as a catalyst, and is a method that enables control of the molecular weight and molecular weight distribution, synthesis of block copolymers, control of the polymer architecture to produce linear, star-shaped or brush-shaped polymers or the like, and polymer terminal functional group modification by a nucleophilic substitution reaction of a terminal halogen atom following the reaction. The effectiveness of atom transfer radical polymerization is well known for controlled polymerization of a variety of vinyl monomers including styrene, acrylate esters, methacrylate esters and acrylonitrile.

Examples of the catalyst used in the atom transfer radical polymerization method (ATRP) include copper chloride, copper bromide and copper iodide. By using these transition metals in the form of a metal complex with an amine-based or imine-based multidentate ligand such as 2,2'-bipyridine, N,N,N',N'-tetramethylethylenediamine, diethylenetriamine, triethylenetetramine, tris[2-(dimethylamino)ethyl]amine or tris(2-pyridylmethyl)amine, good solubility can be ensured, and the catalyst is used in a state of controlled activity.

The initiator used in the atom transfer radical polymerization method (ATRP) is an organic compound having at least one atom that can undergo atom transfer, and an alkyl halide is mainly used. Specific examples include 2-hydroxyethyl 2-bromoisobutyrate, ethyl 2-chloroisobutyrate, methyl 2-bromoisobutyrate, methyl 2-chloroisobutyrate, benzyl bromide, benzyl chloride, 1-phenyl ethyl bromide, and 1-phenyl ethyl chloride.

Examples of the solvent used in the atom transfer radical polymerization method (ATRP) include toluene, N,N-dimethylformamide, acetone, methanol, ethanol and water.

Examples of methods for preparing the TGase substrate-containing monomer and the TGase substrate-containing polymer are described below in the examples. These are merely examples of methods for preparing a TGase substrate-containing monomer and a TGase substrate-containing polymer according to the present invention, and the invention is not limited to these particular examples.

Purification of the TGase substrate-containing monomer and the TGase substrate-containing polymer can be performed by high performance liquid chromatography (HPLC) or gel permeation chromatography (GPC) or the like. Further, identification of the TGase substrate-containing monomer can be performed by MALDI TOF-MS, NMR and IR and the like. Further, HPLC can be used to confirm the product and determine the yield.

The protein-polymer complex according to an embodiment of the present invention has a structure in which a protein having a primary amine is bound to a glutamine (Gln) residue in the TGase substrate-containing polymer having a glutamine (Gln) residue on a side chain. Further, the protein-polymer complex according to another embodiment of the present invention has a structure in which a protein having a glutamine (Gln) residue is bound to a primary amine in the TGase substrate-containing polymer having a primary amine on a side chain.

The protein-polymer complex according to the present embodiment may be obtained, for example, by a method that includes a protein binding step of using a transglutaminase (TGase) to bind a protein having a primary amine to a glutamine (Gln) residue of the TGase substrate-containing polymer having a glutamine (Gln) residue on a side chain. Further, the protein-polymer complex according to the present embodiment may also be obtained, for example, by a method that includes a protein binding step of using a transglutaminase (TGase) to bind a protein having a glutamine (Gln) residue to a primary amine of the TGase substrate-containing polymer having a primary amine on a side chain.

In the protein-polymer complex, there are no particular limitations on the ratio n of the protein relative to the polymer, provided that n is 1 or greater, and the value of n may be adjusted as required. In those cases where the protein-polymer complex is used in the detection or the like of a target protein described below, a large value for n enhances the detection sensitivity, and is consequently preferred. However, if n is too large, then the efficiency of the binding of the target protein via an antigen-antibody reaction or the like may sometimes deteriorate.

When the present description states that "binding is performed using TGase", with the exception of special circumstances, this description means that the obtained linking portion is generated as a result of a primary amine and a Gln residue forming an ε-(γ-glutamyl)lysine bond or a γ-glutamyl amide bond.

In the present embodiment, the Lys residue that is recognizable by TGase may be a primary amine. In this description, a Lys residue is used as an example, but unless specifically stated otherwise, the description also applies to primary amines. The term "primary amine" include not only organic amines, but also Lys and Gly and the like.

There are no particular limitations on the protein having a glutamine (Gln) residue and the protein having a primary amine, and examples include affinity molecules having the ability to bind to other biopolymers, such as protein A, protein G, low-molecular weight antibodies, single chain antibodies, avidin, streptavidin and lectin, and enzymes such as alkaline phosphatase, peroxidase and glutathione S-transferase.

In the protein-polymer complex according to the present embodiment, the protein may have a labeling portion. For example, a labeling protein such as a labeling enzyme having a labeling portion may be introduced, for example using a transglutaminase (TGase), into the TGase substrate-containing polymer. Examples of the method used for introducing the labeling protein include chemical modification methods and genetic engineering methods.

Examples of the labeling portion include enzymes, fluorescent dyes, compounds containing a radioactive isotope, labels that can be detected magnetically (such as magnetic nanoparticles), labels that can be detected thermally (such as temperature-responsive polymers) and labels that can be detected electrically (such as polymers containing ferrocene sites), although from the viewpoints of detection sensitivity and handling and the like, at least one of an enzyme and a fluorescent dye is preferable.

There are no particular limitations on the fluorescent dye, provided it is a material that emits fluorescence or phosphorescence in response to irradiation with ultraviolet light or visible light or the like of a selected wavelength. Examples of fluorescent dyes include fluorescein, rhodamine, dansyl and carbocyanine derivatives, whereas examples of fluorescent proteins include green fluorescent protein and variants thereof.

Examples of radioactive isotopes include deuterium ($^2$H), tritium ($^3$H), $^{10}$B, $^{13}$C, $^{15}$N and $^{18}$O.

It is thought that for TGase, a substrate that functions as a Lys residue donor has fewer structural restrictions than a substrate that functions as a Gln residue donor. Accordingly, there are cases where the labeling enzyme or the like that is to be modified has a TGase-recognizable Lys residue from the beginning, and cases where a tag comprising a TGase-recognizable Lys residue is added to the enzyme.

Examples of known good substrates for microbial TGase include peptides composed of an amino acid sequence represented by LLQG (SEQ ID NO: 1), LAQG (SEQ ID NO: 2), LGQG (SEQ ID NO: 3), PLAQSH (SEQ ID NO: 4), FERQHMDS (SEQ ID NO: 5) or TEQKLISEEDL (SEQ ID NO: 6), or peptides composed of an amino acid sequence represented by GLGQGGG (SEQ ID NO: 7), GFGQGGG (SEQ ID NO: 8), GVGQGGG (SEQ ID NO: 9) or GGLQGGG (SEQ ID NO: 10). Further, examples of known good substrates for guinea pig liver-derived TGase include benzyloxycarbonyl-L-glutamylphenylalanine (Z-QF), a peptide composed of an amino acid sequence represented by EAQQIVM (SEQ ID NO: 11), or peptides composed of an amino acid sequence represented by GGGQLGG (SEQ ID NO: 12), GGGQVGG (SEQ ID NO: 13), GGGQRGG (SEQ ID NO: 14), GQQQLG (SEQ ID NO: 15), PNPQLPF (SEQ ID NO: 16) or PKPQQFM (SEQ ID NO: 17). Depending on the type of TGase used, the Gln residue that is recognizable by TGase may exist as one of these types of peptides.

In substrate peptides in which the N-terminal is a glycine (G), the N-terminal amino group can function as a TGase substrate, and therefore by-products caused by self cross-linking may occur. Accordingly, in the case of substrate peptides in which the N-terminal is a glycine (G), the peptide can be protected from becoming a TGase substrate by substituting the hydrogen atoms of the N-terminal amino group with an appropriate group, thereby ensuring that the desired linkage occurs. In this description, unless specifically stated otherwise, the expression "N-terminal protection" is used to describe this type of protection. It is known that the reactivity varies depending on the method employed for the N-terminal protection. Specifically, it is known that for mammals-derived TGase, protection by N-terminal acetylation of GQQQLG (namely, Ac-GQQQLG) or conversion of the N-terminal amino acid to DOPA (L-3,4-dihydroxyphenylalanine) (namely, DOPA-GQQQLG) results in increased reactivity. These types of protection examples may also be utilized in the present embodiment.

The Lys residue (K) that is recognizable by TGase may exist as a peptide having an amino acid sequence represented by MKHKGS (SEQ ID NO: 18), MRHKGS (SEQ ID NO: 23), MRRKGS (SEQ ID NO: 24) or MHRKGS (SEQ ID NO: 25). Tagging with this type of peptide containing a TGase-recognizable Lys residue can be used for the purpose of binding a labeling enzyme or the like to a desired site on a protein, such as the C-terminal or N-terminal. Examples of other peptides containing a TGase-recognizable Lys residue and their amino acid sequences include modified S-peptide (GSGMKETAAARFERAHMDSGS (SEQ ID NO: 19)), MGGSTKHKIPGGS (SEQ ID NO: 20), N-terminal glycines (N-terminal GGG, N-terminal GGGGG (SEQ ID NO: 21)), and MKHKGGGSGGGSGS (SEQ ID NO: 22) in which the linker region between N-terminal MKHKGS and the target protein has been extended.

Proteins such as labeling enzymes having an added peptide containing a TGase-recognizable Lys residue at the C-terminal or N-terminal can be prepared as recombinant proteins using genetic engineering techniques. Purification of such recombinant proteins in which a TGase substrate peptide tag has been introduced at the C-terminal or N-terminal can be conducted by gel permeation chromatography or the like, using a purification peptide tag added at the N-terminal or C-terminal respectively (for example, a (His) 6-tag (hexahistidine tag)) (in order to avoid any deterioration in the reactivity of the TGase, the design should be made so that the purification peptide tag is introduced at a different terminal from the terminal containing the introduced substrate peptide tag). Confirmation of the amino acid sequence may be performed by using a DNA sequencer to confirm the gene sequence of the plasmid vector that codes the protein, or in the case of a substrate peptide introduced at the N-terminal, by direct identification by N-terminal analysis. Confirmation of the protein purification can be performed by SDS-PAGE or the like.

There are no particular limitations on the labeling enzyme, provided it possesses a property that enables detection to be performed using a coloration reaction or the like. Examples include alkaline phosphatase (AP), glutathione S-transferase (GST), luciferase and peroxidase. Of these, from the viewpoints of achieving high catalytic activity and good stability, alkaline phosphatase or peroxidase is preferred. From the viewpoint of facilitating introduction of a peptide tag, proteins that can be produced by genetic engineering are preferred.

In those cases where the protein-polymer complex is used under comparatively high temperature conditions (for example, 70° C. or higher), if a mesophile-derived enzyme is used, then loss of activity may be a concern. In such cases, an alkaline phosphatase derived from the hyperthermophile *Pyrococcus furiosus* (PfuAP) may be used as the target enzyme.

Furthermore, in the protein-polymer complex, the protein may be an enzyme that is stable relative to organic solvents and heat. This type of high-stability enzyme can be obtained by screening from the natural world (for example, see Chemistry and Chemical Industry, vol. 61 (No. 6), pp. 571 to 575 (2008), Taku Uchiyama and Kentaro Miyazaki, Bioscience and Industry, vol. 66 (No. 5), pp. 234 to 239 (2008), and Noriyuki Dokyu, Bioscience and Industry, vol. 66 (No. 12), pp. 667 to 670 (2008)), or by techniques for increasing the stability using protein engineering (for example, see Hiroyasu Ogino, Bio Industry, vol. 25 (No. 7), pp. 16 to 23 (2008), and Kentaro Miyazaki, Bio Industry, vol. 25 (No. 7), pp. 52 to 58 (2008)). By using these techniques, even enzymes derived from mesophiles can be converted to enzymes that exhibit favorable organic solvent resistance and heat resistance.

A variety of enzymes can be used as the transglutaminase (TGase). Currently known TGase varieties include those derived from mammals (guinea pig and human), invertebrates (insects, horseshoe crab, sea urchin), plants, bacteria and protists (myxomycetes), and in the case of human-derived TGase, eight isozymes have been discovered. An example of a preferred TGase that can be used favorably in the present embodiment, particularly in terms of stability, ease of handling, and bulk producibility and the like, is microbial transglutaminase (MTG).

When MTG is used in the present embodiment, based on the expected MTG catalysis, the binding reaction between the protein having a Lys residue and the TGase substrate-containing polymer is predicted to proceed in two stages, namely formation of an acyl-enzyme complex via a nucleophilic substitution reaction of the cysteine (Cys) residue that represents the MTG active center at the Gln of the TGase substrate-containing polymer, and a subsequent elimination of the MTG via a nucleophilic substitution reaction at the acyl-enzyme complex by the Lys of the protein containing the labeling portion.

In the present embodiment, the molar concentration ratio of the protein that is bound relative to the TGase substrate-containing polymer is preferably 2 or greater, and is more preferably 5 or greater. When the abbreviated term "concentration ratio" is used in this description, unless specifically stated otherwise, the term refers to a ratio between molar concentrations.

In those cases where MTG is used as the TGase to perform the binding reaction, in addition to ensuring that the molar concentration ratio satisfies a specific range as described above, the reaction is preferably performed at a pH of 5.5 to 8.0 and at a temperature of 4 to 50° C. (for example, at room temperature (18 to 22° C.)). Under such conditions, a satisfactorily high reaction rate can be achieved within 12 hours, preferably within 6 hours, and more preferably within 3 hours.

By using the protein-polymer complex according to the present embodiment, the function of the protein introduced into the protein-polymer complex can be improved at, or in the vicinity of, a solid-liquid interface. As examples of this improvement that is obtainable by using the protein-polymer complex of the embodiment described above, a method for detecting a protein which is capable of detecting a target protein with good sensitivity at, or in the vicinity of, a solid-liquid interface, and an enzyme reaction method which, compared with a stand-alone enzyme, exhibits enhanced enzyme reaction efficiency at, or in the vicinity of, a solid-liquid interface are described below.

<Method for Detecting Protein>

A method for detecting a protein according to an embodiment of the present invention is a method comprising binding, either directly or indirectly, the protein-polymer complex and a target protein that exists within a target material, binding a labeling molecule comprising a portion that binds specifically to the protein of the bound protein-polymer complex, and detecting the labeling molecule.

Further, a method for detecting a protein according to another embodiment of the present invention is a method comprising binding, either directly or indirectly, a protein-polymer complex comprising a labeling portion, and a target protein that exists within a target material, and detecting the labeling portion of the bound protein-polymer complex.

Examples of the protein that represents the detection target include IgG and antigenic proteins. By using the protein-polymer complex according to the present invention, primary antibodies of almost all animal types can be detected. The protein-polymer complex according to the present invention can yield a higher S/N ratio than conventional enzyme-labeled secondary antibodies. Further, the detection sensitivity can be similar or superior to that of conventional enzyme-labeled secondary antibodies, meaning the protein-polymer complex can be very versatile. By using the protein-polymer complex according to the present invention, binding to a multitude of primary antibodies can be achieved, and even in those cases where a plurality of target substances (antigens) are to be detected, because a separate antibody need not be prepared to bind each antigen specifically, the versatility can be excellent.

The protein-polymer complex and the method for detecting a protein according to embodiments of the present invention can be used in fundamental research fields such as western blot analysis, ELISA and immunohistochemistry (immunostaining), and also in fields such as pathological examination.

Further, the protein-polymer complex according to an embodiment of the present embodiment can also be used in the detection of antigens other than proteins that can be bound by antibodies, including low-molecular weight antigens such as digoxigenin, polypeptides, nucleic acids, and lipids and the like.

<Other Methods for Using the Protein-Polymer Complex>

In addition to the detection of proteins and the like, the protein-polymer complex according to an embodiment of the present embodiment can also be used in cascade enzyme reaction systems and enzyme reaction systems which degrade substrates concertedly, such as in the degradation of cellulose.

<Enzyme Reaction Method>

The protein-polymer complex according to an embodiment of the present invention can be used in enzyme reactions. In other words, a protein-polymer complex comprising a polymer having a glutamine (Gln) residue or a primary amine on a side chain, in which either a protein having a primary amine is bound to the glutamine (Gln) residue or a protein having a glutamine (Gln) residue is bound to the primary amine, and in which the protein is an enzyme, may act upon a substrate.

Examples of the enzyme include cellulases, which are enzymes that hydrolyze cellulose, and xylanases and chitinases, which are enzymes that act upon water-insoluble substrates. Cellulases are classified into three types, namely endoglucanase (EG) which randomly cleaves the non-crystalline regions inside cellulose, cellobiohydrolase (CBH) which degrades cellulose from the terminals into cellobiose units, and β-glucosidase (BGL) which degrades oligosaccharides to generate glucose.

By using a protein-polymer complex in which a plurality of enzymes have been complexed with the polymer, the efficiency of the enzyme reactions can be improved compared with the stand-alone enzymes.

EXAMPLES

A more detailed description of the present invention is presented below based on a series of examples and comparative examples, but the present invention is in no way limited by the following examples.

For MTG, a product manufactured by Ajinomoto Co., Inc. was used. For K-tag EGFP and wild-type EGFP, recombinant proteins prepared in *E. coli* were used. In terms of the reagents used in relation to monomer syntheses, Z-QG-OH and 2-hydroxyethyl methacrylate (HEMA) were purchased from Sigma-Aldrich Co., Ltd. Further, Z-Q(Trt)-OH, HCl·Gly-OEt, 1-ethyl-3-(3-dimethylaminopropyl)-carbodiimide hydrochloride (EDC), N,N'-dicyclohexylcarbodiimide (DCC), 1-hydroxybenzotriazole monohydrate (HOBt), N,N-diisopropylethylamine (DIEA) and N,N-dimethyl-4-aminopyridine (DMAP) were purchased from Watanabe Chemical Industries, Ltd. Triethylene glycol (TEG) and methacryloyl chloride were purchased from Tokyo Chemical Industry Co., Ltd. In terms of the reagents used in relation to the polymer syntheses, tert-butyl methacrylate (tBMA), CuCl, tris[2-(dimethylamino)ethyl]amine (Me$_6$TREN), 2-hydroxyethyl 2-bromoisobutyrate and 2-methacryloyloxyethyl phosphorylcholine (MPC) were purchased from Sigma-Aldrich Co., Ltd., and acrylamide, 2,2'-azobis(isobutyronitrile) (AIBN) and anhydrous toluene were purchased from Wako Pure Chemical Industries, Ltd. A Polystyrene Standard ReadyCal set was purchased from Sigma-Aldrich Co., Ltd., and LiBr.H$_2$O and trifluoroacetic acid (TFA) were purchased from Wako Pure Chemical Industries, Ltd. A 10 to 20% gradient gel (e-PAGEL (a registered trademark) E-R1020L) was purchased from ATTO Corporation. For all other reagents, commercially available products were used unless specifically stated otherwise. Nuclear magnetic resonance (NMR) spectral measurements were performed using an AV300M apparatus (manufactured by Bruker Corporation). Gel permeation chromatography (GPC) was performed using a high performance liquid chromatograph apparatus LaChrom Elite (pump: L2130, differential refractive index detector: L-2490, ultraviolet detector: L-2455, manufactured by Hitachi, Ltd.). Matrix-assisted laser desorption ionization time-of-flight mass analysis (MALDI-ToF MS) was performed using an Autoflex III (manufactured by Bruker Corporation). In the following examples, "room temperature" refers to a temperature of 18° C. to 28° C.

Example 1

[Evaluation of Reactivity of Z-QG-Containing Monomer with MTG]

In order to evaluate the reactivity of a Z-QG-containing monomer as a Gln substrate, an MTG-catalyzed reaction was performed using an enhanced green fluorescent protein (EGFP) containing a K-tag (MRHKGS) that had been introduced using genetic engineering techniques as a model protein. First, the Z-QG-containing monomer Z-QG-EMA was synthesized.

(Synthesis of Z-QG-EMA)

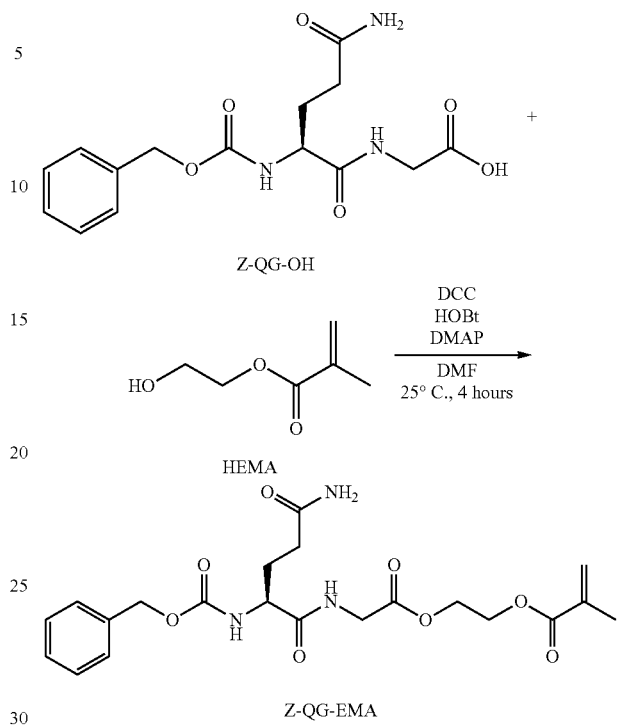

A 200 mL round-bottom flask was charged with Z-QG-OH (0.20 g, 0.59 mmol), N,N-dimethylformamide (DMF) (6.5 mL) was added, the mixture was cooled in ice, and then HEMA (0.17 g, 1.3 mmol, 2.2 eq./Z-QG-OH) was added. Subsequently, DCC (0.15 g, 0.71 mmol, 1.2 eq./Z-QG-OH) and HOBt (0.11 g, 0.73 mmol, 1.2 eq./Z-QG-OH) were added. DMAP (15 mg, 0.12 mmol, 0.21 eq./Z-QG-OH) was then added, the temperature was raised gradually to room temperature, and the mixture was then stirred at room temperature for 4 hours. A reaction trace was performed by thin layer chromatography (TLC), which confirmed the disappearance of the raw materials. The white precipitate that formed in the reaction solution was removed by suction filtration, the solvent was then removed by distillation under reduced pressure, and the resulting product was dissolved in ethyl acetate. A 10% aqueous solution of citric acid was added, and the resulting mixture was stirred at room temperature and then extracted twice into ethyl acetate. The organic phase was washed with a 5% aqueous solution of sodium bicarbonate and then a saturated saline solution, and following drying over anhydrous sodium sulfate, the solvent was removed by distillation under reduced pressure, yielding a crude product.

Following purification by flash column chromatography (silica gel, n-hexane:ethyl acetate=1:10 (v/v)), the solvent was removed by distillation under reduced pressure, yielding a white powder. Identification of the product was performed by $^1$H-NMR, $^1$H-$^1$H COSY and MALDI-ToF MS.

Figure 2:
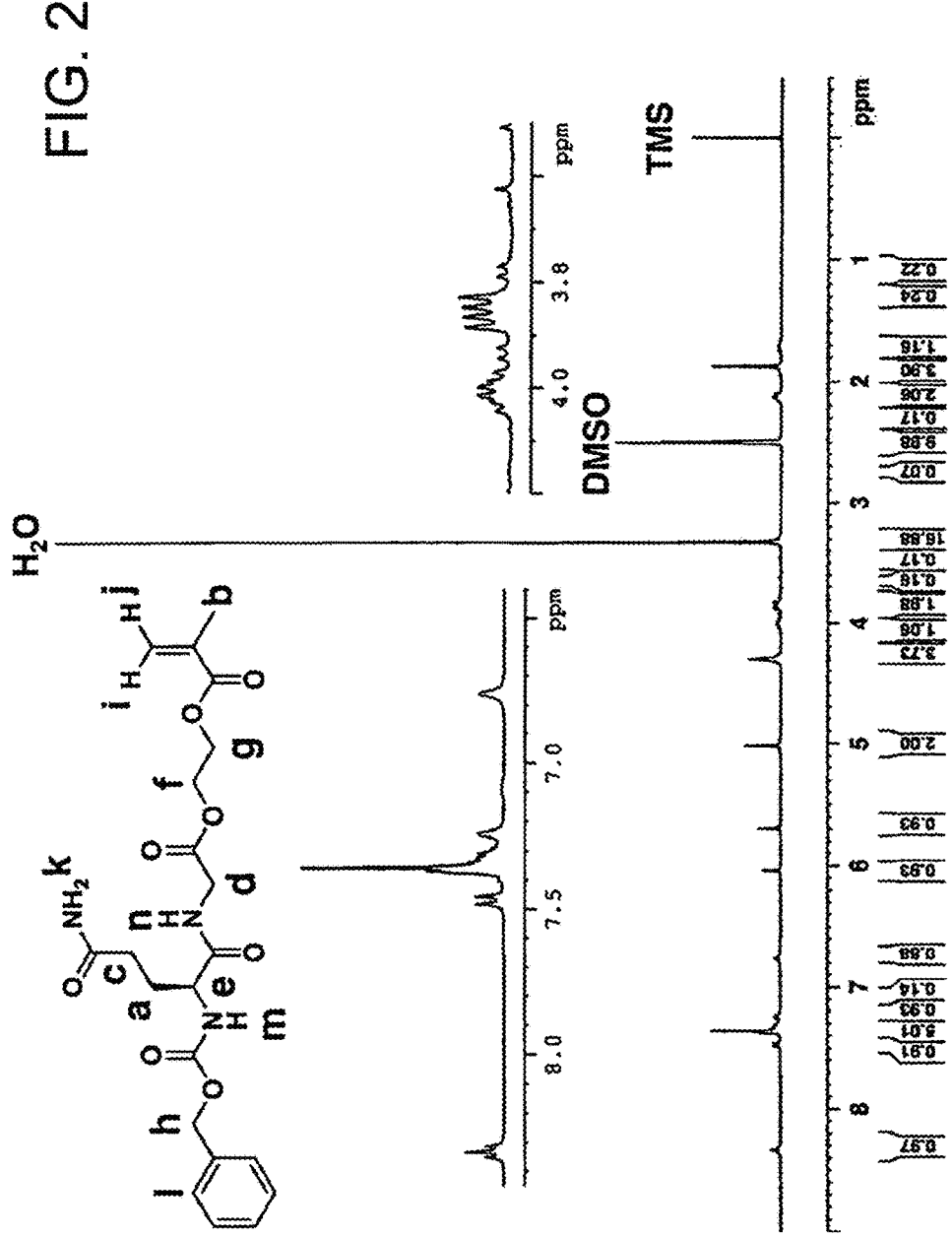
FIG. 2 is a diagram illustrating the $^1$H-NMR spectrum (300 MHz, DMSO-d6, TMS standard) of Z-QG-EMA in an example.

The product was a white powder (yield: 25 mg, 0.056 mmol, yield: 10%). The $^1$H-NMR spectrum and the peak assignments are shown in FIG. 2 and Table 1 respectively. Further, the results of MALDI-ToF MS analysis (matrix: dithranol) were as shown below. These results confirmed the production of Z-QG-EMA.

[M+H]+ (theoretical value: 450.46, measured value: -), [M+Na]+ (theoretical value: 472.44, measured value: 472.06)

TABLE 1

1H-NMR spectral assignments for Z-QG-EMA (300 MHz, DMSO-d6, TMS standard)

| Chemical shift δ (ppm) | Peak splitting (J Hz) | Assignment |
|---|---|---|
| 1.70 to 1.74 | m | a |
| 1.87 | m | a, b |
| 2.13 | m | c |
| 3.77 to 3.85 | m | d |
| 3.92 to 3.94 | m | e |
| 4.32 | br | f, g |
| 5.07 | s | h |
| 5.69 | s | i |
| 6.06 | s | j |
| 6.76 | br | k |
| 7.24 | br | k |
| 7.31 to 7.34 | m | l |
| 7.46 to 7.48 | d (6.0) | m |
| 8.31 to 8.35 | t (5.7) | n |

(Cross-Linking of Z-QG-EMA and K-Tag EGFP Using MTG)

Figure 27:
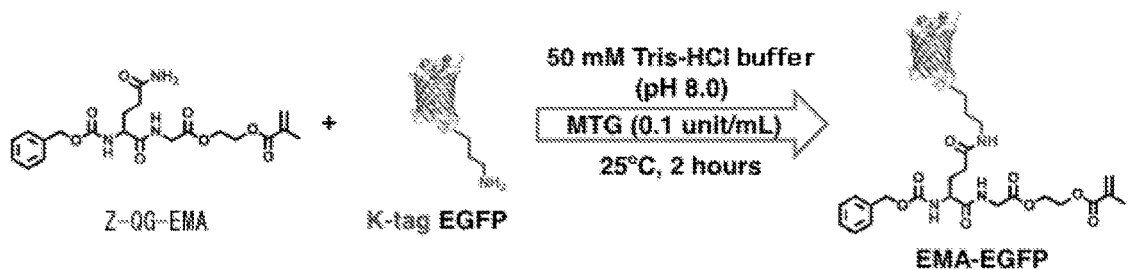
FIG. 27 illustrates a cross-linking reaction of Z-QG-EMA and K-tag EGFP using MTG.

In order to investigate whether a Z-QG-containing monomer would be recognized by MTG as a Gln residue, cross-linking of Z-QG-EMA and K-tag EGFP was performed using MTG as shown in FIG. 27. The composition of each reagent is shown in Table 2. The reaction time was set to 2 hours, the reaction temperature was set to 25° C., and samples of the reaction solution extracted after 5, 60 and 120 minutes were each treated with a 4-fold volume of a 1% aqueous solution of TFA to halt the reaction, and a reaction trace was performed by MALDI-ToF MS.

A sample to which MTG had not been added, and a sample to which wild-type EGFP with no introduced K-tag had been added were tested in a similar manner as negative controls.

TABLE 2

Composition of reaction solution for cross-linking using MTG

| Reagent | Final concentration |
|---|---|
| Z-QG-EMA in DMSO | 200 μM |
| K-tag EGFP | 10 μM |
| MTG | 0.1 unit/ml |
| Tris-HCl buffer solution (pH 8.0) | 50 mM |

Figure 3:
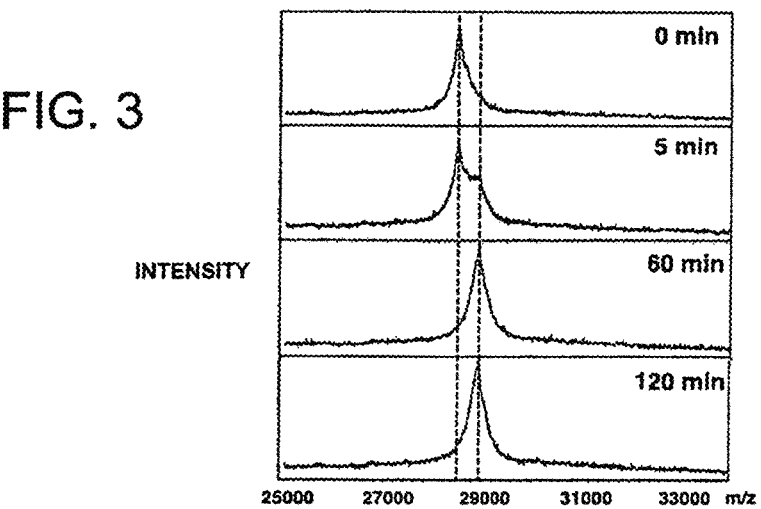
FIG. 3 is a diagram illustrating a reaction trace (matrix: α-CHCA) by MALDI-ToF MS in an example.
Figure 4:
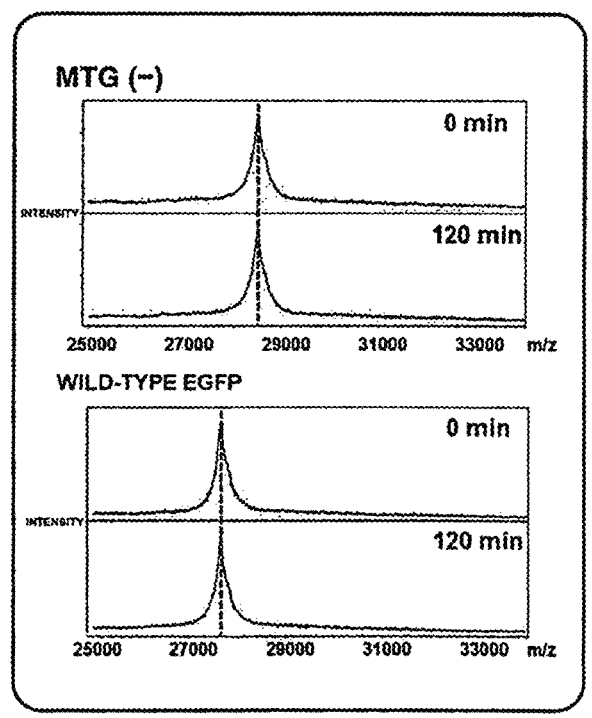
FIG. 4 is a diagram illustrating a reaction trace (negative control) by MALDI-ToF MS in an example.

The results of the MALDI-ToF MS measurements performed at each of the reaction times are shown in FIG. 3, FIG. 4 and Table 3. The appearance of a peak corresponding with the molecular weight of a molecule (EMA-EGFP) formed by a single molecule of Z-QG-EMA (Mw: 449.45) binding to the K-tag EGFP confirmed that the Z-QG-EMA was recognized as a Gln residue by MTG, and introduced into the K-tag EGFP. Further, 60 minutes after the start of the reaction, only the EMA-EGFP was detected, making it clear that the MTG reaction proceeds very efficiently. At this time, peaks corresponding with the molecular weights of molecules formed due to the binding of two or more molecules of the Z-QG-EMA were not detected. Further, in the case in which no MTG was added and the case in which wild-type EGFP was used, no change was observed in the mass spectrum. The above results suggested strongly that the Z-QG-EMA had been introduced specifically at the K-tag of the K-tag EGFP.

TABLE 3

| | Peak values | |
|---|---|---|
| | Theoretical value [M + H]+ | Measured value [M + Na]+ |
| K-tag EGFP | 28470.14 | 28495.55 |
| EMA-EGFP | 28902.56 | 28926.18 |

<Synthesis of Monomer Having MTG-Recognizable Glutamine (Gln) Residue (Z-QG-Containing Monomer)>

As illustrated by the reaction formulas shown below, a monomer having an MTG-recognizable glutamine (Gln) residue (Z-QG-containing monomer) was synthesized in three stages. When the Z-QG-containing monomer Z-QG-EMA is subjected to polymerization by atom transfer radical polymerization, there is a possibility that the amino group of the Gln side chain may act as a ligand. Accordingly, a monomer Z-QG(Trt)G-EMA was synthesized in which the amino group of the Gln side chain was protected with a trityl group that exhibits significant steric hindrance.

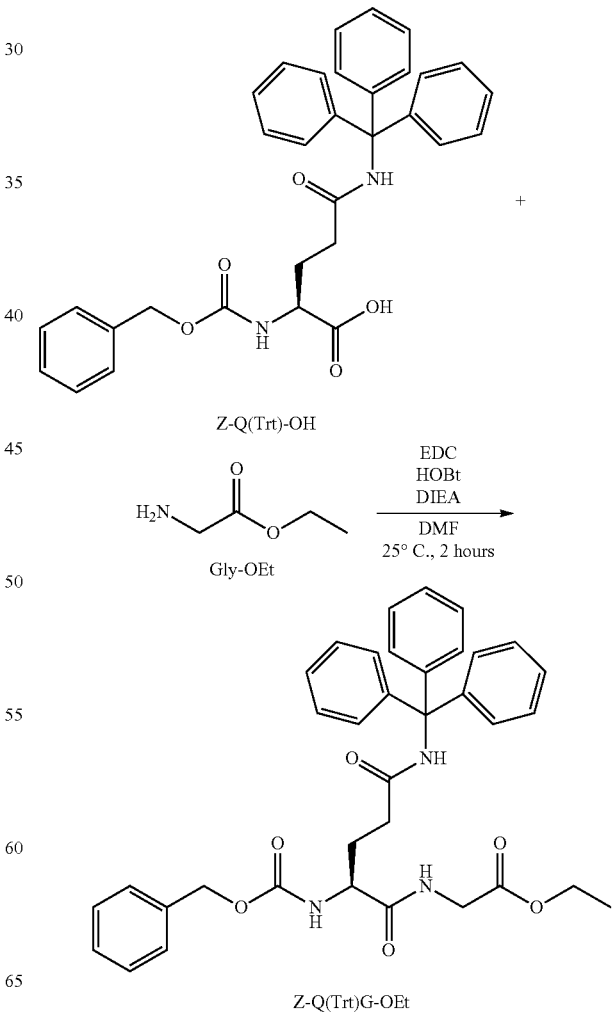

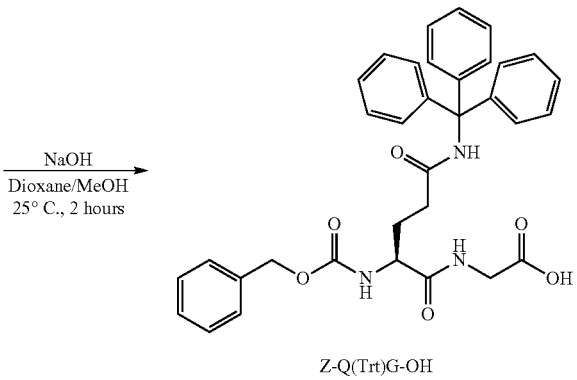

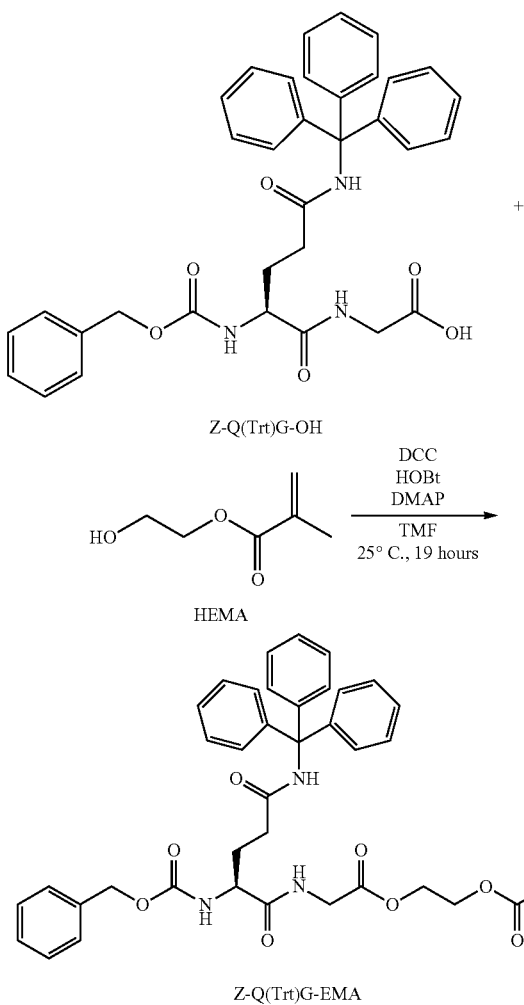

was raised gradually to room temperature, and the reaction solution was then stirred at room temperature for 2 hours. A reaction trace was performed by TLC, which confirmed the disappearance of the raw materials.

A 10% aqueous solution of citric acid was added to the reaction solution, and the resulting mixture was stirred at room temperature and then extracted twice into ethyl acetate. The organic phase was washed with a 5° aqueous solution of sodium bicarbonate and then a saturated saline solution, and following drying over anhydrous sodium sulfate, the solvent was removed by distillation under reduced pressure, yielding a crude product.

Following purification by flash column chromatography (silica gel, n-hexane:ethyl acetate=5:6 (v/v)), the solvent was removed by distillation under reduced pressure, yielding a white powder. Identification of the product was performed by $^1$H-NMR, $^1$H-$^1$H COSY and MALDI-ToF MS.

Figure 5:
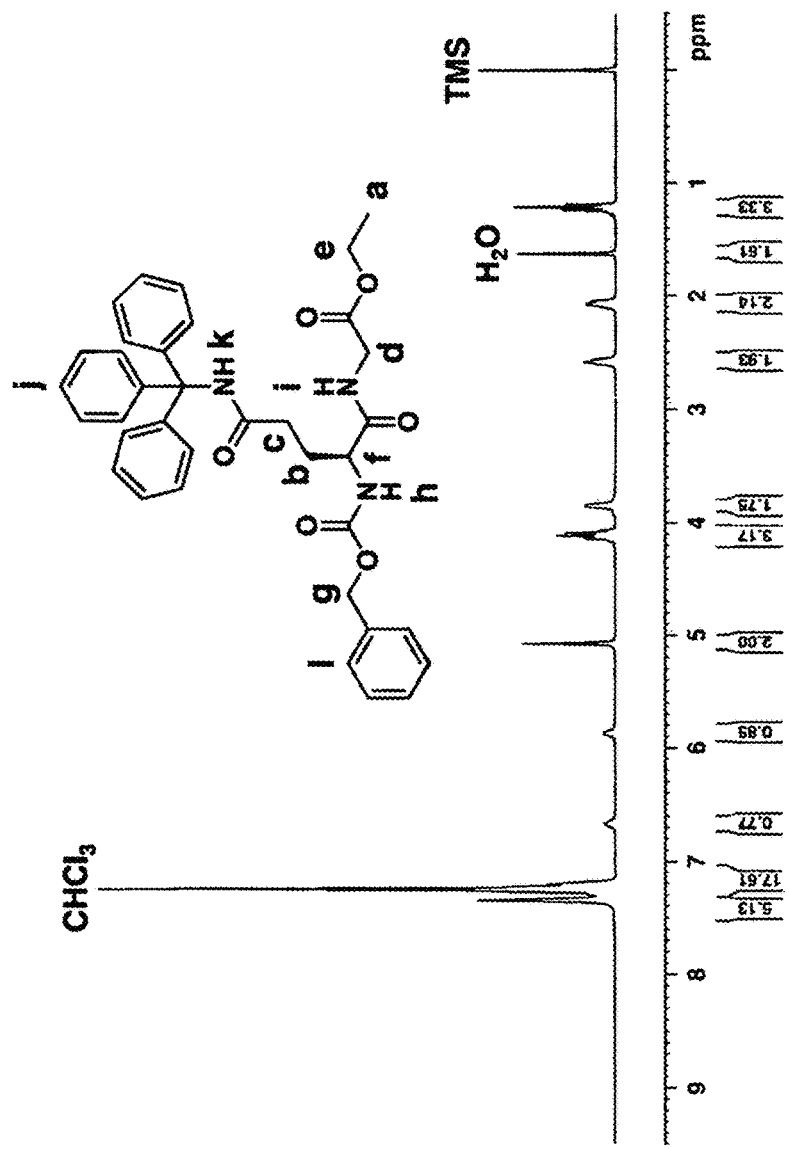
FIG. 5 is a diagram illustrating the $^1$H-NMR spectrum (300 MHz, CDCl$_3$, TMS standard) of Z-Q(Trt)G-OEt in an example.

The product was a white powder (yield: 0.58 g, 0.95 mmol, yield: 50%). The $^1$H-NMR spectrum and the peak assignments are shown in FIG. 5 and Table 4 respectively. Further, the results of MALDI-ToF MS analysis (matrix: dithranol) were as shown below. These results confirmed the production of Z-Q(Trt)G-OEt.

$[M+H]^+$ (theoretical value: 608.70, measured value: -), $[M+Na]^+$ (theoretical value: 630.39, measured value: 630.45), $[M+K]^+$ (theoretical value: 646.79, measured value: 646.44)

TABLE 4

$^1$H-NMR spectral assignments for Z-Q(Trt)G-OEt (300 MHz, CDCl$_3$, TMS standard)

| Chemical shift δ (ppm) | Peak splitting (J Hz) | Assignment |
|---|---|---|
| 1.19 to 1.24 | t (7.1) | a |
| 2.05 to 2.08 | m | b |
| 2.57 to 2.58 | m | c |
| 3.85 | s | d |
| 4.07 to 4.14 | m | e, f |
| 5.08 | s | g |
| 5.86 | br | h |
| 6.67 | br | i |
| 7.20 to 7.25 | m | j, k |
| 7.35 | m | l |

(Synthesis of Z-Q(Trt)G-OEt)

In a 200 mL round-bottom flask, Z-Q(Trt)-OH (1.0 g, 1.9 mmol) and HCl.Gly-OEt (0.54 g, 3.9 mmol, 2.1 eq./Z-Q(Trt)-OH) were dissolved in DMF (40 mL), DIEA (1.4 mL, 8.1 mmol, 4.3 eq./Z-Q(Trt)-OH) was added, and the solution was cooled in ice. Next, EDC (0.44 g, 2.3 mmol, 1.2 eq./Z-Q(Trt)-OH) and HOBt (0.35 g, 2.3 mmol, 1.2 eq./Z-Q(Trt)-OH) were dissolved in a small amount of DMF, and then added gradually to the above solution. The temperature (Synthesis of Z-Q(Trt)G-OH)

In a 100 mL round-bottom flask, Z-Q(Trt)G-OEt (0.40 g, 0.66 mmol) was dissolved in 1,4-dioxane (8.0 mL), methanol (2.0 mL) and a 1 M aqueous solution of sodium hydroxide (0.66 mL, 0.66 mmol, 1.0 eq./Z-Q(Trt)G-OEt) were added, and the resulting solution was stirred at room temperature for 50 minutes.

Subsequently, 0.01 M hydrochloric acid was added to the reaction solution to adjust the pH to 4, and the solution was stirred at room temperature to halt the reaction. Following removal of the solvent by distillation under reduced pressure, the residue was dissolved in ethyl acetate, washed with a 10% aqueous solution of citric acid, and then extracted twice into ethyl acetate. The extract was washed with a saturated saline solution, and following drying over anhydrous sodium sulfate, the solvent was removed by distillation under reduced pressure, yielding a crude product. When the product was investigated by TLC, residual raw materials were detected, and therefore 1,4-dioxane (5.0 mL) was added to the 100 mL round-bottom flask to dissolve the crude product, methanol (1.0 mL) and a 4 M aqueous solution of sodium hydroxide (0.16 mL, 0.64 mmol, 1.0 eq./Z-Q(Trt)G-OEt) were added, and the resulting solution was stirred at room temperature for 2 hours. A reaction trace was performed by TLC, which confirmed the disappearance of the raw materials.

Subsequently, a 10% aqueous solution of citric acid was added to the reaction solution, and the resulting mixture was stirred at room temperature and then extracted twice into ethyl acetate. The extract was then washed with a saturated saline solution, and following drying over anhydrous sodium sulfate, the solvent was removed by distillation under reduced pressure, yielding a crude product.

Following purification by flash column chromatography (silica gel, (1) dichloromethane:methanol=20:1 (v/v), (2) dichloromethane:methanol=15:1 (v/v), (3) dichloromethane:methanol=10:1 (v/v)), the solvent was removed by distillation under reduced pressure, yielding a white powder. Identification of the product was performed by $^1$H-NMR, $^1$H-$^1$H COSY and MALDI-ToF MS. Further, a fraction 1 obtained by column chromatography was also identified by MALDI-ToF MS.

Figure 6:
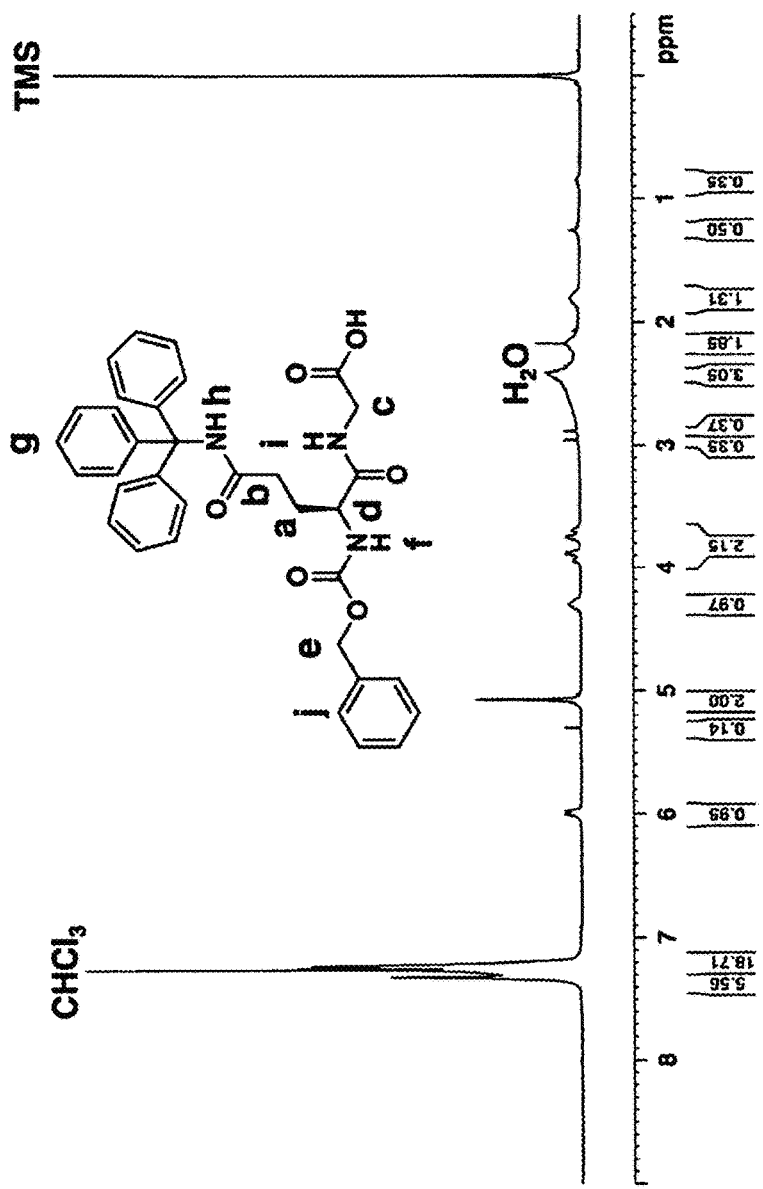
FIG. 6 is a diagram illustrating the $^1$H-NMR spectrum (300 MHz, CDCl$_3$, TMS standard) of Z-Q(Trt)G-OH in an example.

The product was a white powder (yield: 0.14 g, 0.25 mmol, yield: 38%). The $^1$H-NMR spectrum and the peak assignments are shown in FIG. 6 and Table 5 respectively. Further, the results of MALDI-ToF MS analysis (matrix: dithranol) were as shown below.

Product: $[M+H]^+$ (theoretical value: 580.65, measured value: -), $[M+Na]^+$ (theoretical value: 602.63, measured value: 602.39), $[M+K]^+$ (theoretical value: 618.74, measured value: 618.37)

Fraction 1: $[M+H]^+$ (theoretical value: 594.26, measured value: -), $[M+Na]^+$ (theoretical value: 616.24, measured value: 616.46), $[M+K]^+$ (theoretical value: 632.22, measured value: 632.45)

The above results confirmed the production of Z-Q(Trt)G-OH. Further, the MALDI-ToF MS results for the fraction 1 suggest the compound Z-Q(Trt)G-OMe represented by the formula shown below. In order to avoid the production of this Z-Q(Trt)G-OMe, the reaction solvent may be changed from a 1,4-dioxane/methanol system to a 1,4-dioxane/ethanol system.

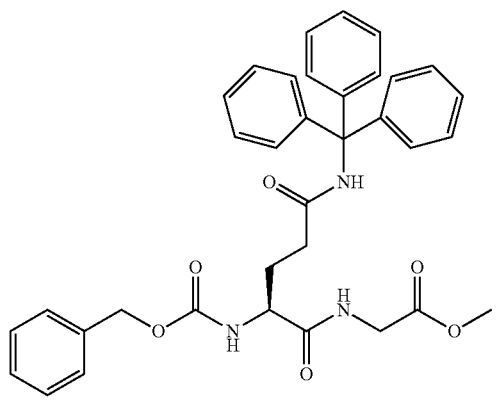 [SMILES: COC(=O)CNC(=O)[C@H](CCC(=O)NC(c1ccccc1)(c1ccccc1)c1ccccc1)NC(=O)OCc1ccccc1]

TABLE 5

$^1$H-NMR spectral assignments for Z-Q(Trt)G-OH (300 MHz, CDCl$_3$, TMS standard)

| Chemical shift δ (ppm) | Peak splitting (J Hz) | Assignment |
| --- | --- | --- |
| 1.81 | br | a |
| 2.17 | br | a |
| 2.39 to 2.47 | br | b |
| 3.71 to 3.96 | m | c |
| 4.30 | br | d |
| 5.07 | s | e |
| 5.98 to 6.00 | br | f |
| 7.23 to 7.26 | m | g, h, i |
| 7.32 | m | j |

(Synthesis of Z-Q(Trt)G-EMA)

A 200 mL round-bottom flask was charged with Z-Q(Trt)G-OH (0.10 g, 0.18 mmol), THF (7 mL) was added, and the solution was cooled in ice. HEMA (0.056 g, 0.43 mmol, 2.4 eq./Z-Q(Trt)G-OH) was then added. Subsequently, DCC (0.046 g, 0.22 mmol, 1.2 eq./Z-Q(Trt)G-OH) and HOBt (0.032 g, 0.21 mmol, 1.2 eq./Z-Q(Trt)G-OH) were dissolved in a small amount of THF, and then added gradually to the above solution. DMAP (3.5 mg, 0.029 mmol, 0.2 eq./Z-Q(Trt)G-OH) was then added, the temperature was raised gradually to room temperature, and the reaction solution was then stirred at room temperature for 19 and a half hours. A reaction trace was performed by TLC, which confirmed the disappearance of the raw materials.

The white precipitate that formed in the reaction solution was removed by suction filtration, the solvent was then removed by distillation under reduced pressure, and the resulting product was dissolved in ethyl acetate. A 10% aqueous solution of citric acid was added, and the resulting mixture was stirred at room temperature and then extracted twice into ethyl acetate. The organic phase was washed with a 5% aqueous solution of sodium bicarbonate and then a saturated saline solution, and following drying over anhydrous sodium sulfate, the solvent was removed by distillation under reduced pressure, yielding a crude product.

Following purification by flash column chromatography (silica gel, (1) n-hexane:ethyl acetate=3:2 (v/v), (2) n-hexane:ethyl acetate=1:1 (v/v)), the solvent was removed by distillation under reduced pressure, yielding a white powder. Identification of the product was performed by $^1$H-NMR, $^1$H-$^1$H COSY, MALDI-ToF MS and elemental analysis.

Figure 7:
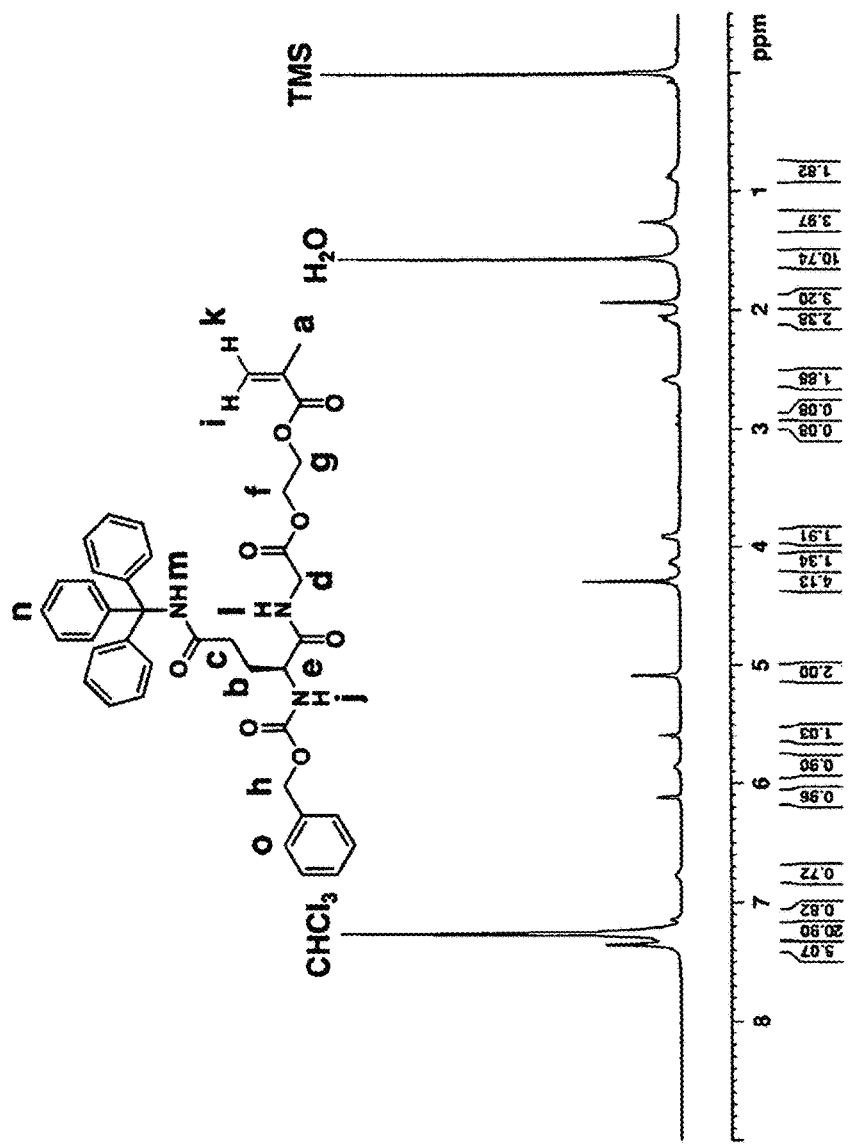
FIG. 7 is a diagram illustrating the $^1$H-NMR spectrum (300 MHz, CDCl$_3$, TMS standard) of Z-Q(Trt)G-EMA in an example.

The product was a white powder (yield: 67 mg, 0.096 mmol, yield: 55%). The $^1$H-NMR spectrum and the peak assignments are shown in FIG. 7 and Table 6 respectively. Further, the results of MALDI-ToF MS analysis (matrix: dithranol) were as shown below.

$[M+H]^+$ (theoretical value: 692.78, measured value: -), $[M+Na]^+$ (theoretical value: 714.76, measured value: 714.62), $[M+K]^+$ (theoretical value: 730.87, measured value: 730.61)

The results of the elemental analysis are shown in Table 7.

The $^1$H-NMR spectrum suggests a ratio Z-Q(Trt)G-EMA:DMF=1:0.03 (mol/mol), and a combination of Z-Q(Trt)G-EMA+0.5H$_2$O+0.03DMF yields a match with the measured values within a margin of error of 0.3%. The above results confirmed the production of Z-Q (Trt) G-EMA.

TABLE 6

$^1$H-NMR spectral assignments for Z-Q(Trt)G-EMA (300 MHz, CDCl$_3$, TMS standard)

| Chemical shift δ (ppm) | Peak splitting (J Hz) | Assignment |
|---|---|---|
| 1.94 | s | a |
| 2.09 | m | b |
| 2.59 | m | c |
| 3.90 to 3.92 | d (5.1) | d |
| 4.13 to 4.14 | m | e |
| 4.29 | s | f, g |
| 5.09 | s | h |
| 5.59 | s | i |
| 5.85 | br | j |
| 6.12 | s | k |
| 6.77 | br | l |
| 7.14 | m | m |
| 7.24 to 7.27 | m | n |
| 7.35 | m | o |

TABLE 7

Results of elemental analysis

| Element | Content [%] | | | |
|---|---|---|---|---|
| | C | H | N | O |
| Measured value | 68.42 | 6.11 | 5.99 | 19.48 |
| Theoretical value | 69.45 | 5.97 | 6.07 | 18.50 |
| Theoretical value (+0.5H$_2$O + 0.03DMF) | 68.49 | 6.05 | 6.04 | 19.42 |

[Synthesis of Polymer Having MTG-Recognizable Gln (Z-QG-Containing Polymer)]

From the viewpoints of MTG substrate recognition and protein function retention, it is thought that it is desirable that a certain spacing is maintained between the Z-QG sites that function as MTG reaction sites. Accordingly, as shown in the reaction formulas shown below, a copolymerization was conducted with tert-butyl methacrylate (tBMA) to synthesize a polymer (Z-Q(Trt)G-containing polymer) formed from Z-Q(Trt)G-EMA and tBMA. By subsequently conducting deprotection of the tert-butyl group and the trityl group that has functioned as a protective group for the Gln side chain, a polymer (Z-QG-containing polymer) formed from Z-QG-EMA and methacrylate was synthesized.

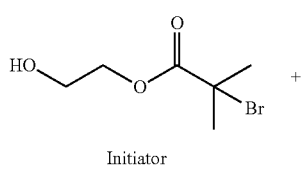

Initiator

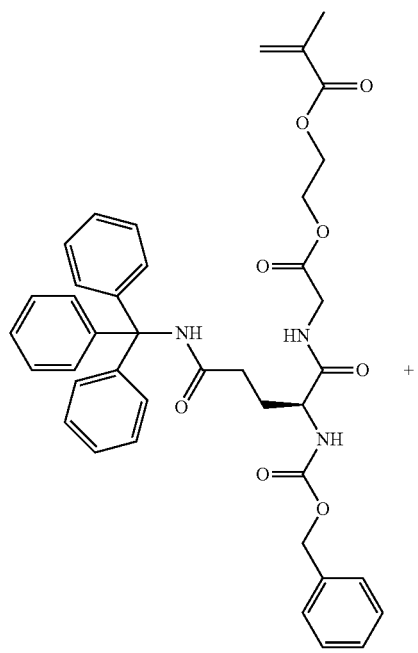

Z-Q(Trt)G-EMA

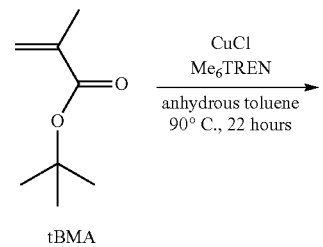

tBMA

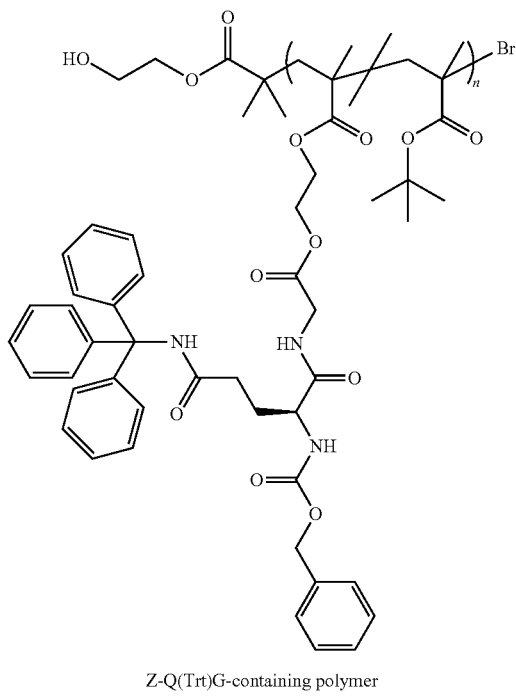

Z-Q(Trt)G-containing polymer

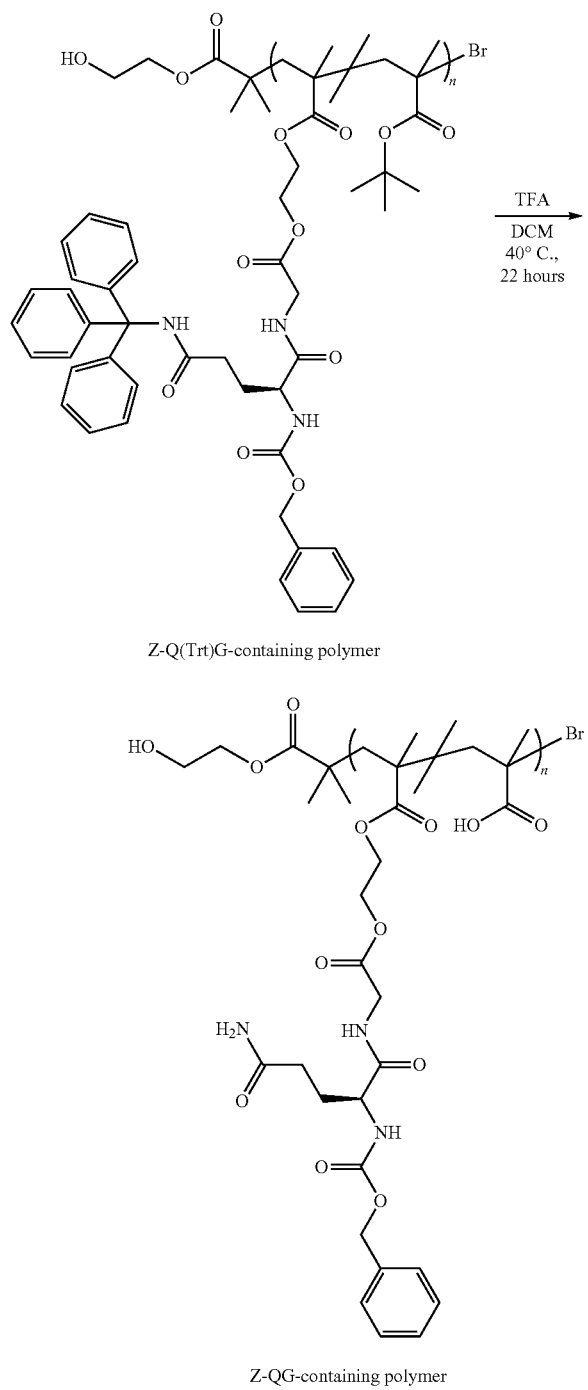

Z-Q(Trt)G-containing polymer

Z-QG-containing polymer (Synthesis of Z-Q(Trt)G-Containing Polymer)

An atom transfer radical polymerization was performed using the procedure described below so that Z-Q(Trt)G-EMA/Z-Q(Trt)G-containing monomer=4% and the degree of polymerization reached 50. The reason for setting the degree of polymerization to 50 was so that, in the ¹H-NMR, the degree of polymerization could be easily calculated from the ratio between the integral of the peak derived from the initiator and the integral of the peak derived from the polymer main chain. The final concentration of each of the reagents is shown in Table 8.

TABLE 8

Composition of ATRP reaction solution

|  | Reagent | Final concentration |
|---|---|---|
| Z-QG-containing monomer | Z-Q(Trt)G-EMA | 92 mM |
| Comonomer | tBMA | 2.2M |
| Catalyst | CuCl | 51 mM |
| Ligand | tris[2-(dimethylamino)ethyl]amine (Me₆TREN) | 0.15M |
| Initiator | 2-hydroxyethyl 2-bromoisobutyrate | 48 mM |

A 10 mL Schlenk flask A was charged with Z-Q(Trt)G-EMA (44.7 mg, 0.0646 mmol) and CuCl (3.52 mg, 0.0356 mmol), the flask was then sealed with a septum stopper, and the atmosphere inside the flask was substituted with argon. Similarly, a 10 mL Schlenk flask B and a 10 mL test tube C were also each sealed with a septum stopper, and the internal atmosphere was substituted with argon. To the Schlenk flask A were added tBMA (250 μL, 1.54 mmol) and anhydrous toluene (50 μL). To the Schlenk flask B were added 2-hydroxyethyl 2-bromoisobutyrate (50 μL, 0.345 mmol) and anhydrous toluene (1.03 mL). Each of the Schlenk flasks A and B was subjected to three freeze-deaeration repetitions. The test tube C was charged with Me₆TREN(tris[2-(dimethylamino)ethyl]amine: 100 μL, 0.374 mmol) and anhydrous toluene (1.07 mL), and the solution was subjected to argon bubbling. Subsequently, 300 μL of the solution from the test tube C was added to the Schlenk flask A, and another freeze-deaeration was performed. The Schlenk flask A was then placed in a 90° C. oil bath, and once a substantially uniform solution had been obtained, 100 μL of the solution from the Schlenk flask B was added to the Schlenk flask A to initiate the reaction. After 22 hours, the system was opened and the reaction was halted. The obtained green-brown solid was dissolved in THF and passed through a silica column, and the green precipitate was removed by passing an adequate amount of dichloromethane through the column. The solvent was removed by distillation under reduced pressure, yielding a light yellow solid. The product was identified by ¹H-NMR.

The thus obtained light yellow solid was dissolved in a small amount of THF (150 μL) and then added dropwise to a cooled mixed solvent of methanol:water=4:1 (v/v), and following stirring using a vortex stirrer, a centrifugal separation (8,000 rpm, 3 min) was performed, and the supernatant was removed. This operation was repeated 5 times, and the resulting product was then freeze dried overnight to obtain a white powder. The product was identified by ¹H-NMR. The molecular weight and the molecular weight distribution of the product were determined by GPC. The GPC analysis was performed using a differential refractive index (RI) detector and an ultraviolet detector (UV, 269 nm) for detection, and using 5 mM LiBr-containing DMF as the eluent at a flow rate of 1.0 mL/min, with analysis performed relative to standard polystyrenes.

Figure 8:
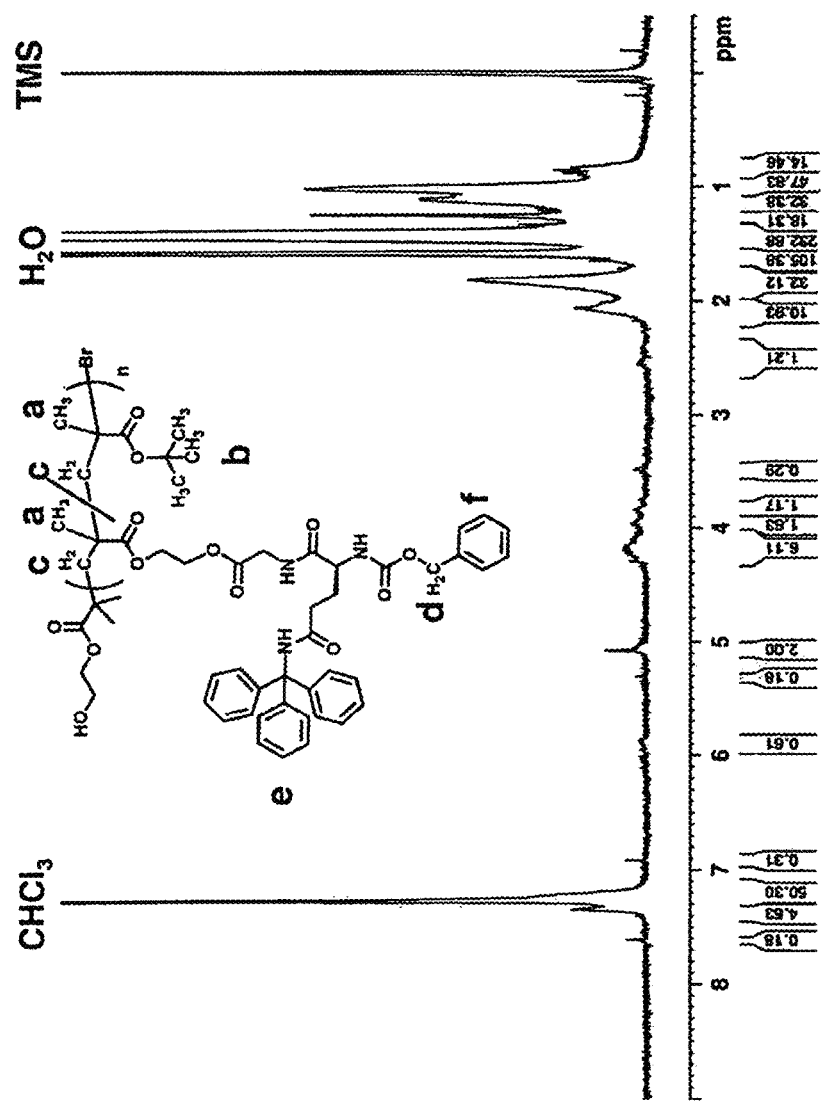
FIG. 8 is a diagram illustrating the $^1$H-NMR spectrum (300 MHz, CDCl$_3$, TMS standard) of a Z-Q(Trt)G-containing polymer (following purification) in an example.

The crude product was a light yellow solid (yield: 151 mg), and the purified product was a white powder (yield: 76 mg). The ¹H-NMR spectrum and the peak assignments of the purified product are shown in FIG. 8 and Table 9 respectively. A precipitation operation was used to confirm that the residual monomers (Z-Q(Trt)G-EMA and tBMA) had been removed. Further, based on peak integrals, it was estimated that about 4% of Z-QG had been introduced into the polymer chain.

TABLE 9

¹H-NMR spectral assignments for Z-Q(Trt)G-containing polymer
(following purification) (300 MHz, CDCl₃, TMS standard)

| Chemical shift δ (ppm) | Peak splitting (J Hz) | Assignment |
| --- | --- | --- |
| 0.8 to 1.2 | br | a |
| 1.3 to 1.5 | br | b |
| 1.7 to 2.2 | br | c |
| 5.08 | s | d |
| 7.26 | m | e |
| 7.35 | m | f |

Figure 9:
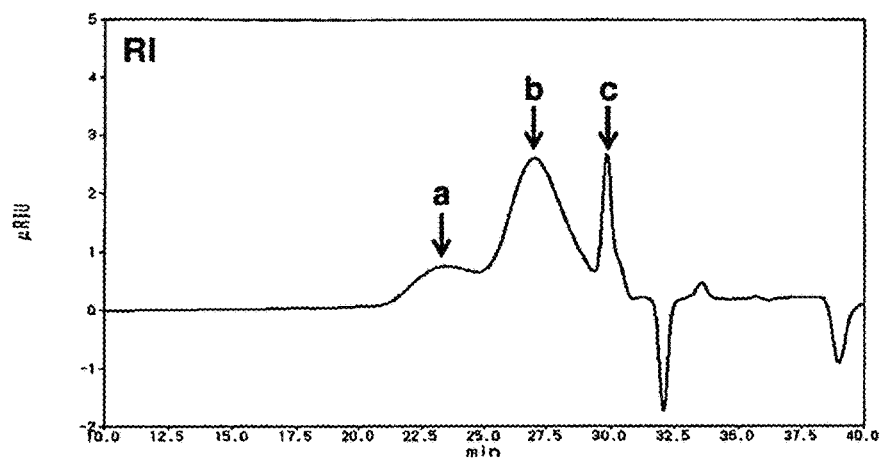
FIG. 9 is a diagram illustrating a GPC measurement result (RI detection, 5 mM LiBr-containing DMF, 1.0 mL/min, polystyrene standards) in an example.
Figure 10:
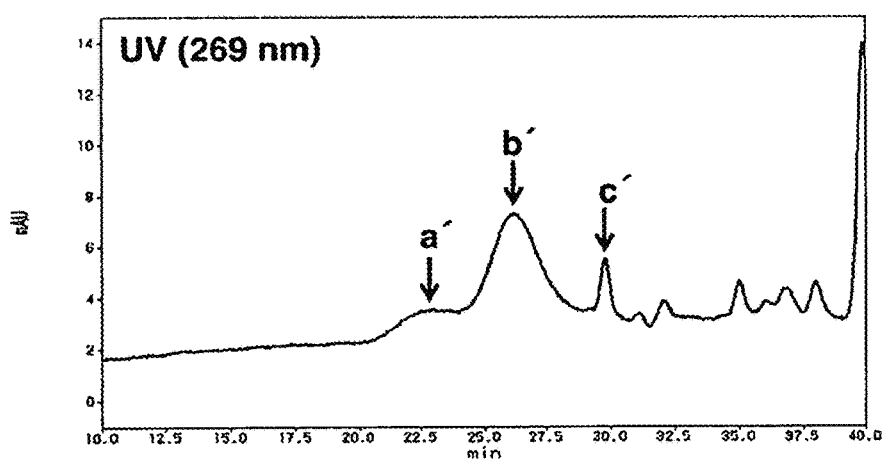
FIG. 10 is a diagram illustrating a GPC measurement result (UV detection (269 nm), 5 mM LiBr-containing DMF, 1.0 mL/min, polystyrene standards) in an example.

The results of measuring the molecular weight and the molecular weight distribution for the product by GPC are shown in FIG. 9, FIG. 10 and Tables 10 and 11.

TABLE 10

Peak information in GPC chromatogram (RI detection)

| | Mn | Mw | Polydispersity (Mw/Mn) | Degree of polymerization | Z-QG number/ polymer chain |
| --- | --- | --- | --- | --- | --- |
| a | 58 kDa | 71 kDa | 1.2 | 353 | 14 |
| b | 13 kDa | 14 kDa | 1.1 | 79 | 3.2 |
| c | 5.4 kDa | 5.4 kDa | 1.0 | 33 | 1.3 |

TABLE 11

Peak information in GPC chromatogram (UV detection)

| | Mn | Mw | Polydispersity (Mw/Mn) | Degree of polymerization | Z-QG number/ polymer chain |
| --- | --- | --- | --- | --- | --- |
| a' | 58 kDa | 69 kDa | 1.2 | 353 | 14 |
| b' | 10 kDa | 12 kDa | 1.2 | 61 | 2.4 |
| c' | 4.7 kDa | 4.8 kDa | 1.0 | 29 | 1.1 |

Synthesis was conducted with the aim of producing a Z-Q(Trt)G-containing polymer having a degree of polymerization of 50 (theoretical molecular weight: 8.2 kDa), but production of polymer components having a higher molecular weight was confirmed. In both the RI detection and the UV detection, three molecular weight distributions were confirmed, making it clear that three types of Z-Q(Trt)G-containing polymers had been produced. It is thought that because the scale of the polymer synthesis was a very small 0.7 mL, there is a possibility that non-uniform reactions may have occurred in the reaction system.

(Synthesis of Z-QG-Containing Polymer)

Deprotection was performed for the trityl group that represents the protective group for the Gln residue of the obtained Z-Q(Trt)G-containing polymer, and the tert-butyl group of the comonomer.

A 25 mL round-bottom flask was charged with the Z-Q(Trt)G-containing polymer (60 mg), dichloromethane (5 mL) and TFA (5.0 mL) were added, and the resulting mixture was stirred for 22 hours in a 40° C. oil bath. The product was then concentrated using a rotary evaporator and added dropwise to cooled diethyl ether, and following stirring using a vortex stirrer, a centrifugal separation (8,000 rpm, 3 min) was performed, and the supernatant was removed. This operation was repeated 5 times, yielding a light brown solid. This solid was dissolved in ammonia water (pH 11), and then freeze dried overnight to obtain a white powder. The product was identified by ¹H-NMR.

Figure 11:
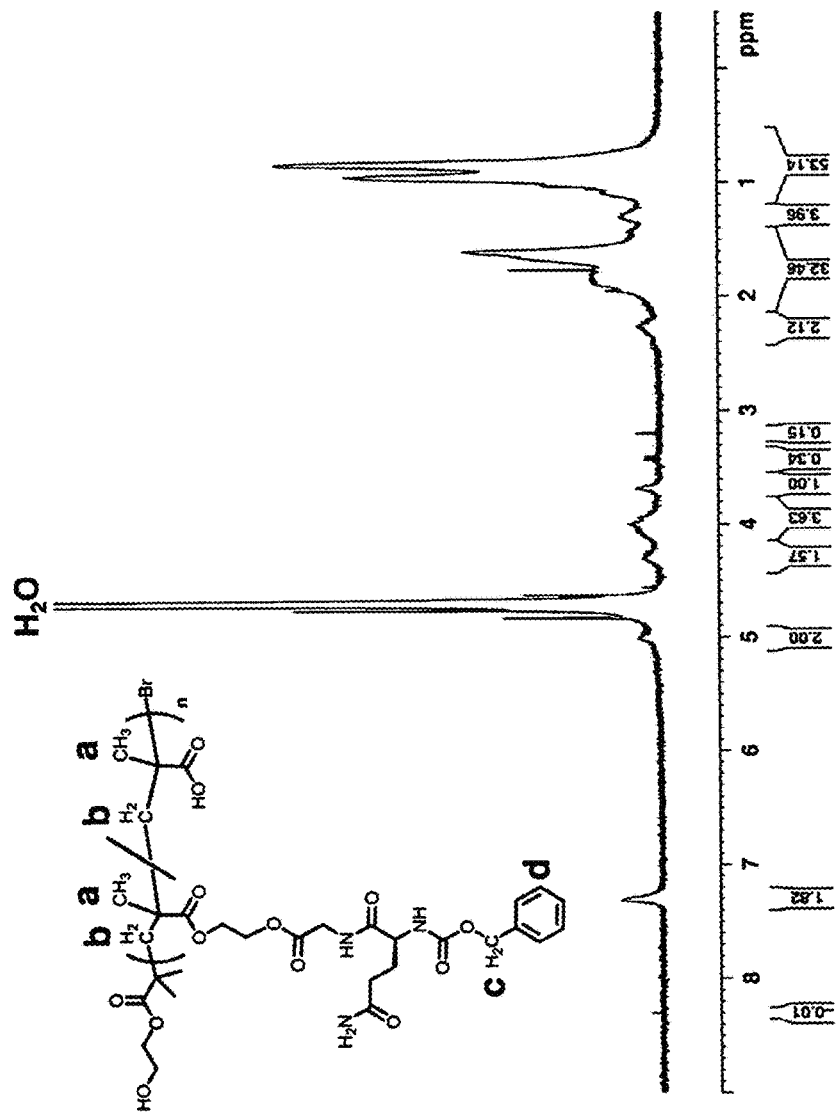
FIG. 11 is a diagram illustrating the $^1$H-NMR spectrum (300 MHz, deuterium oxide) of a Z-QG-containing polymer in an example.

The product was a white powder (yield: 39 mg), the ¹H-NMR spectrum and the peak assignments for which are shown in FIG. 11 and Table 12 respectively. It was confirmed that peaks attributable to the trityl group and the tert-butyl group had disappeared. Further, based on peak integrals, it was estimated that about 2% of Z-QG had been introduced into the polymer chain. It is assumed that the reason for the reduction in the Z-QG content is because the oligomers having a higher Z-QG content were more readily soluble in the solvent (diethyl ether) used in the precipitation operation. Further, as was the case prior to the deprotection, no signal derived from the initiator could be confirmed.

TABLE 12

¹H-NMR spectral assignments for Z-QG-containing polymer
(following purification) (300 MHz, deuterium oxide)

| Chemical shift δ (ppm) | Peak splitting (J Hz) | Assignment |
| --- | --- | --- |
| 0.8 to 1.2 | br | a |
| 1.6 to 2.2 | br | b |
| 5.01 | s | c |
| 7.31 | m | d |

[Introduction of K-Tag into Protein G]
(Expression and Purification of Recombinant Protein G (K-Tag pG))

Figure 13:
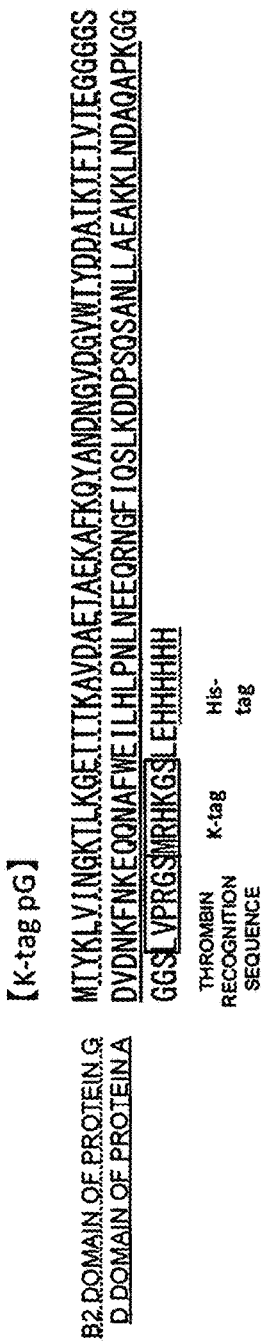
FIG. 13 is a diagram illustrating the amino acid sequence of a protein used in an example.

The gene sequence (SEQ ID NO: 26) of the vector used, and the amino acid sequence (SEQ ID NO: 27) of the protein are shown in FIG. 12 and FIG. 13 respectively. A thrombin recognition sequence (LVPRGS) is introduced between the K-tag sequence and the pG sequence, and by treating the K-tag pG with thrombin, the wild-type pG having no introduced K-tag that is used in the control experiments can be produced easily.

Figure 14:
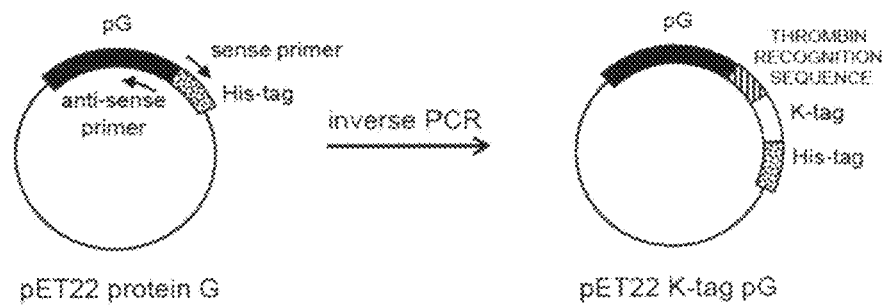
FIG. 14 is a diagram illustrating the preparation of pET22 K-tag pG in an example.

The vector used was prepared by recombination of an artificially synthesized protein G gene into a pET22b+ vector using two restriction enzymes NdeI and XhoI. Using an inverse PCR method, the K-tag sequence and the thrombin recognition sequence were introduced at the C-terminal side of the protein G (FIG. 14). Further, a K-tag protein G containing the thrombin recognition sequence may be synthesized from the beginning as an artificial synthetic gene, and the restriction enzymes then used to achieve recombination of the pET22 plasmid vector.

K-tag pG was expressed from the prepared vector using *E. coli* (BL21 strain). The *E. coli* (BL21 strain) having the transformed vector was precultured overnight at 37° C. and 200 rpm in an LB medium (30 mL) containing ampicillin (100 μg/mL). Culturing was then performed at 37° C. and 200 rpm in an LB medium (1 L) containing ampicillin (100 μg/mL) until the absorbance at 600 nm reached a value of 0.5 to 0.6, and isopropyl β-D-1-thiogalactopyranoside was then added in an amount sufficient to achieve a final concentration of 0.5 mM. Subsequently, culturing was continued at 27° C. and 200 rpm for 8 hours. Following collection of the obtained bacterial cells, the cells were pulverized by an ultrasonic treatment and subjected to His-tag purification using filtration and an Ni-NTA column, and following concentration by ultrafiltration (fraction molecular weight: 10 kDa), a PD-10 column was used to perform a buffer substitution with a 10 mM Tris-HCl buffer solution (pH 8.0), and the resulting sample was then stored at −80° C. The protein concentration of the K-tag pG was calculated by bicinchoninic acid assay (BCA assay), using bovine serum albumin as a standard protein. The expression, isolation and purification were confirmed by SDS-PAGE (15% acrylamide, electrophoresis conditions: 200 V, 20 mA, 70 min) and CBB staining.

Figure 28:
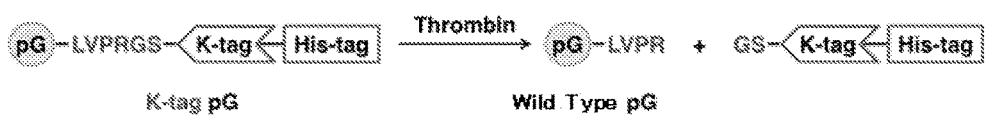
FIG. 28 illustrates a reaction subjecting a purified K-tag pG to a thrombin treatment.

Further, as shown in FIG. 28, by subjecting the purified K-tag pG to a thrombin treatment, the wild-type pG containing no introduced K-tag was also prepared. To 1 mg of the K-tag pG was added sufficient thrombin to achieve 10 units, and the resulting mixture was reacted at 25° C. for 6 hours. His-tag purification was performed using an Ni-NTA column, and following collection of the flow-through fraction, the thrombin was removed using a benzamidine column. Following concentration of the resulting flow-through fraction by ultrafiltration (fraction molecular weight: 5 kDa), a PD-10 column was used to perform a buffer substitution with a 10 mM Tris-HCl buffer solution (pH 8.0), and the resulting sample was then stored at −80° C. The protein concentration of the K-tag pG was calculated by BCA assay, using bovine serum albumin as a standard protein. Isolation and purification were confirmed by SDS-PAGE (15% acrylamide, electrophoresis conditions: 200 V, 20 mA, 70 min) and CBB staining.

[Cross-Linking of K-Tag Protein G and Z-QG-Containing Polymer Using MTG]

Figure 29:
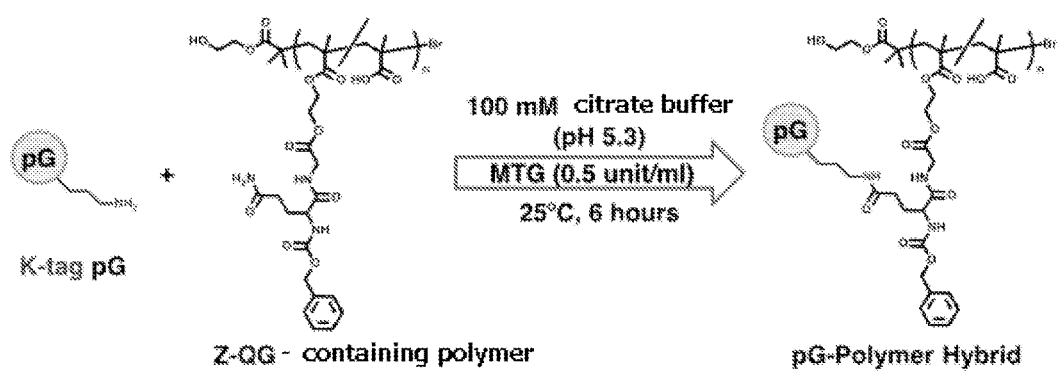
FIG. 29 illustrates a cross-linking reaction of a K-tag pG and a Z-QG-containing polymer using MTG.

As shown in FIG. 29, cross-linking of the K-tag pG and the Z-QG-containing polymer was performed using MTG.

The composition of each reagent is shown in Table 13. In terms of the concentration of the Z-QG-containing polymer, the polymer was prepared with a Z-QG equivalent content of 2%. The reaction time was set to 6 hours and the reaction temperature was set to 25° C. A 2×SDS sample buffer was added to the collected samples of the reaction solution, and following halting of the reaction by heating at 94° C. for 15 minutes, SDS-PAGE (10 to 20% gradient gel, electrophoresis conditions: 200 V, 20 mA, 95 min) was performed, and the products were confirmed by CBB staining.

A sample to which MTG had not been added, and a sample to which wild-type pG with no introduced K-tag had been added were tested in a similar manner as negative controls.

TABLE 13

Composition of reaction solution for cross-linking using MTG

| Reagent | Final concentration |
| --- | --- |
| K-tag pG | 10 µM |
| Z-QG-containing polymer | 200 µM (Z-QG equivalent) |
| MTG | 0.5 unit/ml |
| Citrate buffer solution (pH 5.3) | 100 mM |

Figure 15:
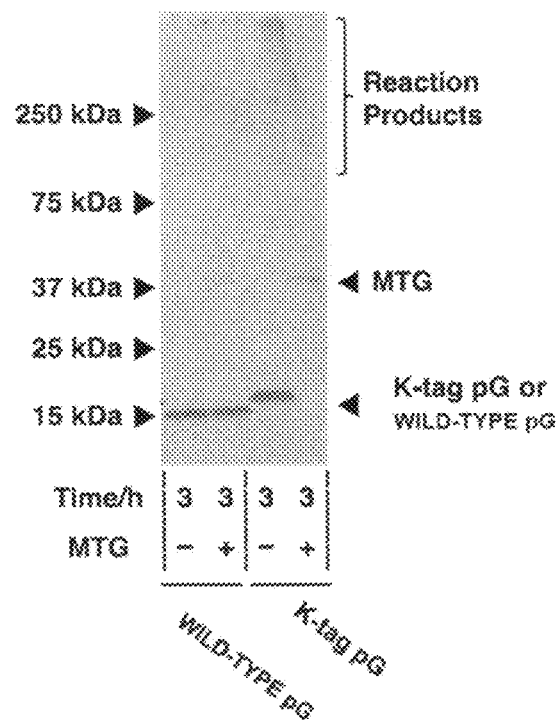
FIG. 15 is a diagram illustrating a reaction trace by SDS-PAGE in an example.

The cross-linking of the K-tag pG and the Z-QG-containing polymer using MTG was traced by SDS-PAGE (FIG. 15). In the results, no change in the bands was observed in the negative control samples. On the other hand, in the sample in which reaction with the Z-QG-containing polymer was conducted using MTG, the intensity of the K-tag pG band decreased, and a new broad signal was confirmed at a higher molecular weight. This confirmed clearly that K-tag pG could be introduced into the Z-QG-containing polymer.

(Evaluation of pH Dependency of Cross-Linking Reaction Using MTG)

In order to evaluate the pH dependency of the cross-linking reaction between K-tag pG and the Z-QG-containing polymer, MTG-catalyzed reactions were performed at different pH levels in buffer solutions of different buffers. The composition of each reagent is shown in Table 14. In terms of the concentration of the Z-QG-containing polymer, the polymer was prepared with a Z-QG equivalent content of 2%.

TABLE 14

Composition of reaction solution for cross-linking using MTG

| Reagent | Final concentration |
| --- | --- |
| K-tag pG | 10 µM |
| Z-QG-containing polymer | 200 µM (Z-QG equivalent) |
| MTG | 0.5 unit/ml |
| Phosphate, citrate, Tris-HCl buffer solutions (pH 4.6 to 8.5) | 100 mM |

The reaction time was set to 3 hours and the reaction temperature was set to 25° C. A 2×SDS sample buffer was added to the collected samples of the reaction solution, and following halting of the reaction by heating at 94° C. for 15 minutes, SDS-PAGE (10 to 20% gradient gel, electrophoresis conditions: 200 V, 20 mA, 95 min) was performed, and the products were confirmed by CBB staining (FIG. 16).

A sample to which MTG had not been added was tested in a similar manner as a negative control. Using the image analysis software Image J, the band intensities of the CBB-stained SDS-PAGE gel were quantified, and the reaction rate of the K-tag pG was calculated from the reduction in the intensity of the K-tag pG band. When calculating band intensities, 5 separate analyses were performed for a single band, and the average value was used.

Figure 16:
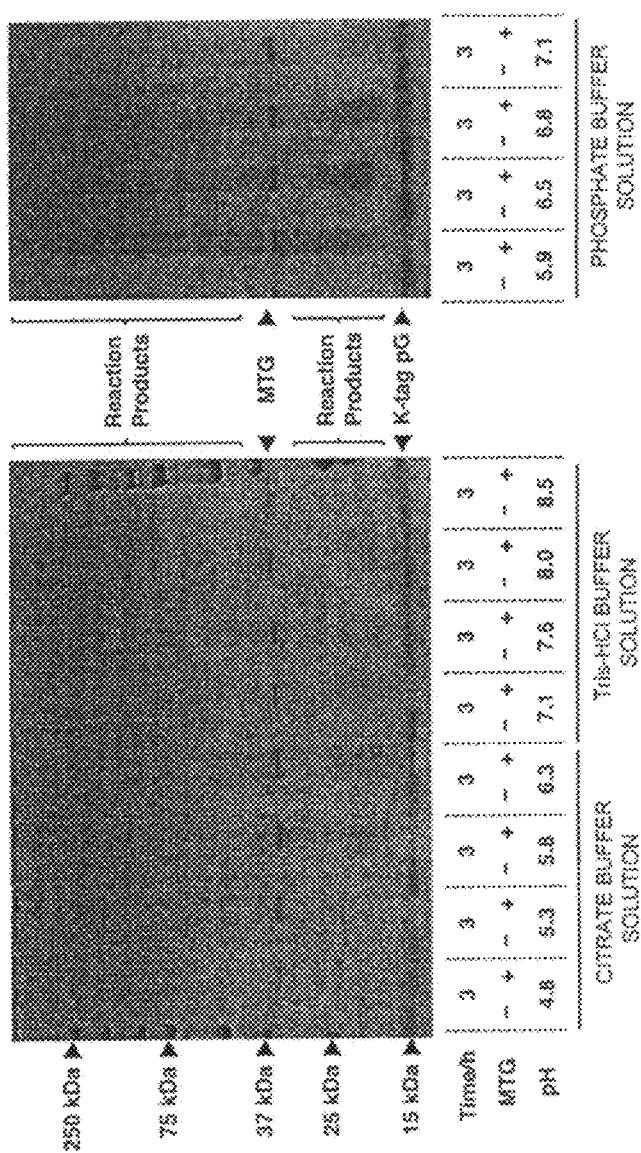
FIG. 16 is a diagram illustrating an evaluation by SDS-PAGE of the pH dependency of an MTG cross-linking reaction in an example.

The fact that differences in the intensity of the K-tag pG band and the intensity of the reaction product bands could be seen in each of the lanes of FIG. 16 confirmed that the MTG reactivity varied depending on the pH. Further, in those lanes in which reaction products were observed, among the two types of reaction products which were observed at a higher molecular weight and a lower molecular weight, the proportion of the lower molecular weight reaction product increased as the pH increased. At present, little detail is known about this change in the reaction products depending on the pH. In the citrate buffer solution (pH 5.3), only the higher molecular weight reaction product was obtained, and based on the assumption that this product is the result of a plurality of K-tag pG molecules undergoing cross-linking with the Z-QG-containing polymer, ELISA was performed to investigate whether a protein accumulation effect could be seen.

Figure 17:
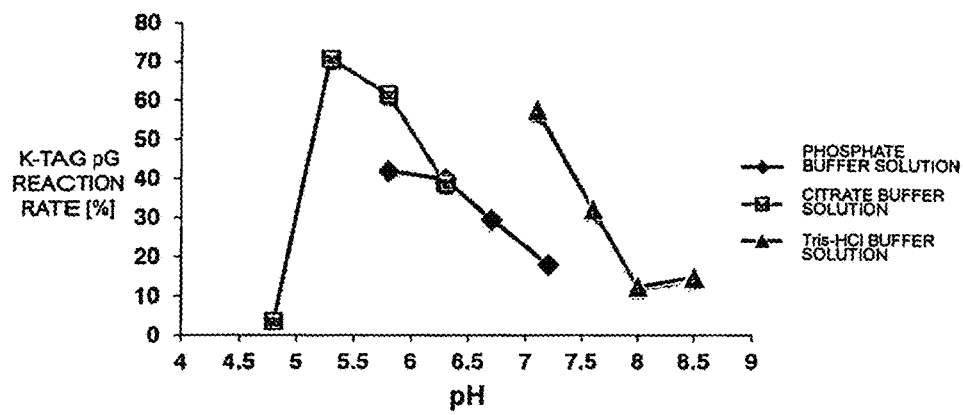
FIG. 17 is a diagram illustrating an evaluation of the pH dependency of a cross-linking reaction by MTG in an example.

Further, the K-tag pG reaction rates at each of the pH levels, calculated by image analysis of the CBB-stained SDS-PAGE gels, are illustrated in FIG. 17. It was evident that even at the same pH, the MTG reactivity changed depending on the buffer solution. Because metal ions such as $Ca^{2+}$ are not required for MTG activity expression, it was predicted that the reactivity would be independent of the type of buffer, but it is thought that the type of buffer does have an effect on the cross-linking between pG and the Z-QG-containing polymer.

[Functional Evaluation of Protein G-Polymer Hybrid Using ELISA Method]

Figure 18:
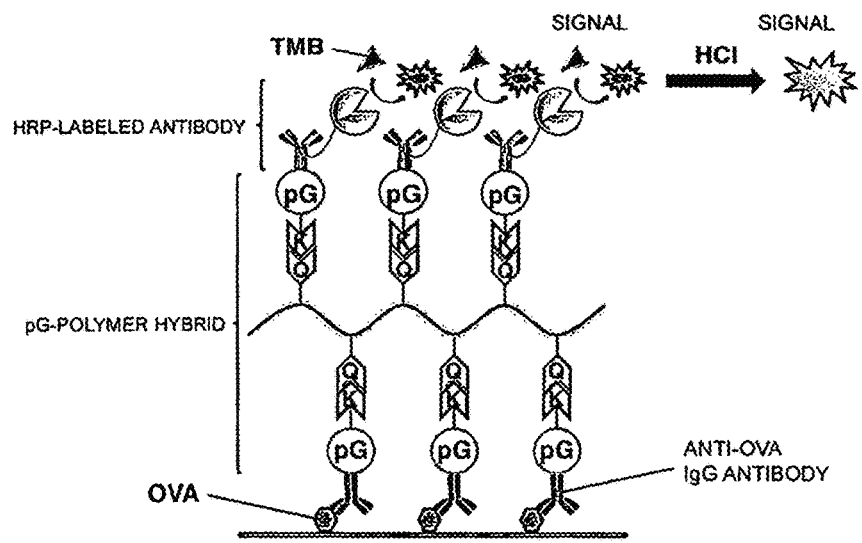
FIG. 18 is a schematic view illustrating ELISA in an example.

In order to illustrate the effects of accumulation of the protein G (pG) on the polymer, ELISA was performed using ovalbumin (OVA) as a model antigen. An outline of the ELISA method used in this investigation is illustrated in FIG. 18.

First, a pG-polymer hybrid (pG-polymer complex) was prepared. The composition of each reagent is shown in Table 15. In terms of the concentration of the Z-QG-containing polymer, the polymer was prepared with a Z-QG equivalent content of 2%. An MTG-catalyzed reaction was conducted with the reaction time set to 6 hours and the reaction temperature set to 25° C. N-ethylmaleimide (NEM) was added in an amount sufficient to obtain a final concentration of 1 mM, thereby halting the reaction, and the reaction solution was then diluted 1,000-fold with Tris-buffered saline (TBS), thus preparing a pG-polymer hybrid solution (pG concentration: 0.01 µM).

A sample to which wild-type pG with no introduced K-tag had been added, and a sample containing only added K-tag pG were prepared in a similar manner as negative controls.

TABLE 15

Composition of reaction solution for cross-linking using MTG

| Reagent | Final concentration |
|---|---|
| K-tag pG | 10 µM |
| Z-QG-containing polymer | 200 µM (Z-QG equivalent) |
| MTG | 0.5 unit/ml |
| Citrate buffer solution (pH 5.3) | 100 mM |

ELISA operations were performed using the procedure described below. First, 100 µL/well of a 50 µg/mL OVA aqueous solution was added to each well of a 96-well immunoplate, and following storage overnight at 4° C., each well was washed with 0.1% Tween20/TBS (TBST) (5 washing repetitions/well). In order to suppress non-specific adsorption to the plate, 200 µL/well of 2% bovine serum albumin/TBS was added, and following standing for 2 hours at 37° C. and blocking, the wells were washed with TBST (5 washing repetitions/well). Next, 100 µL/well of Anti-OVA IgG (rabbit-derived) was added, and following standing for 2 hours at 37° C., the wells were washed with TBST (5 washing repetitions/well). Subsequently, 100 µL/well of the prepared pG-polymer hybrid solution was added, and following standing for 2 hours at 37° C., the wells were washed with TBST (5 washing repetitions/well). Next, 100 µL/well of HRP-labeled anti-guinea pig IgG was added, and following standing for 2 hours at 37° C., the wells were washed with TBST (5 washing repetitions/well). Finally, 100 µL/well of 3,3',5,5'-tetramethylbenzidine (TMB) was added, and the change over time in the absorbance (O.D.) at 370 nm and 37° C. was measured over a period of 30 minutes.

The same tests were performed on a total of 8 samples including the negative controls (Table 16).

TABLE 16

|  | 1 | 2 | 3 | 4 | 5 | 6 | 7 | 8 |
|---|---|---|---|---|---|---|---|---|
| Antigen | − | − | − | − | + | + | + | + |
| Primary antibody | − | − | + | + | − | − | + | + |
| pG or pG-polymer hybrid | − | + | − | + | − | + | − | + |

Figure 19:
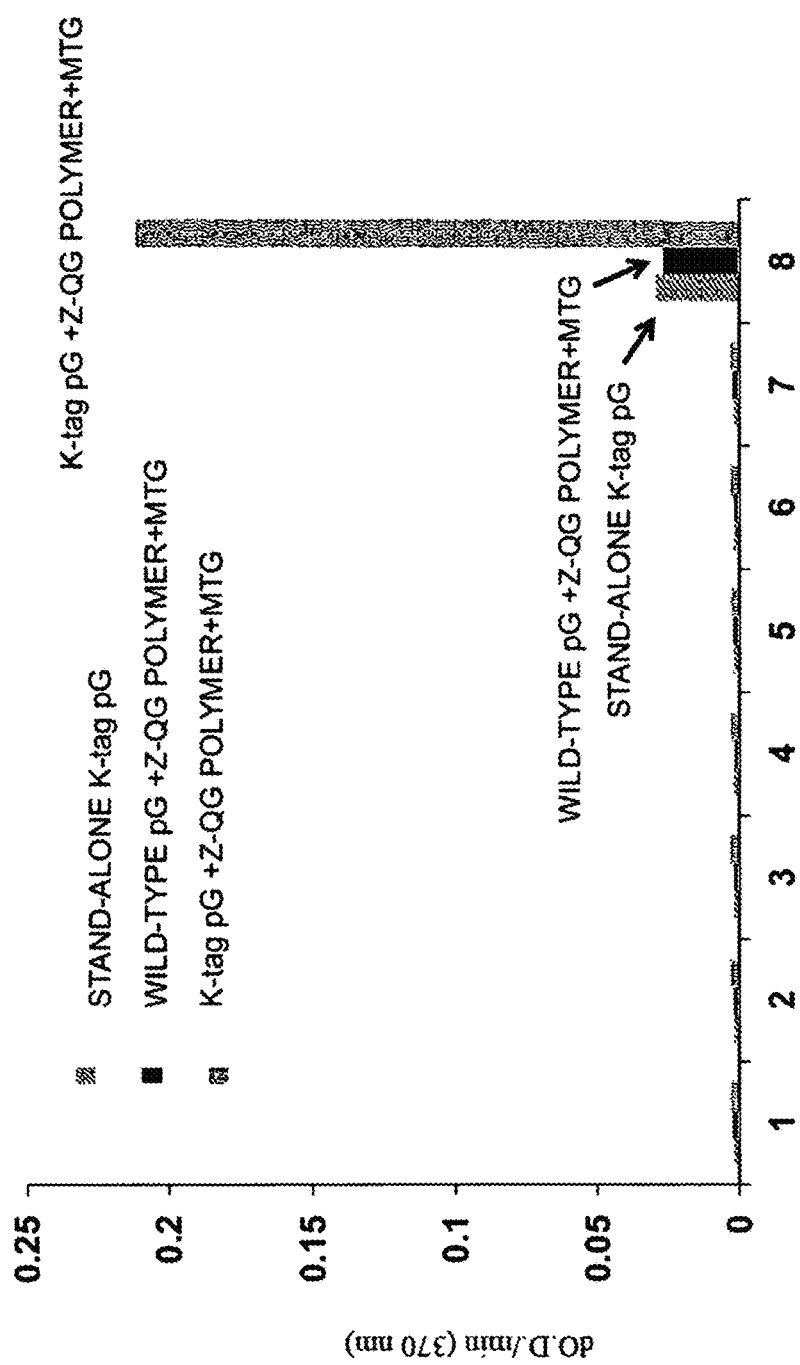
FIG. 19 is a diagram illustrating the results of using ELISA to evaluate the effect of accumulating a protein G on a polymer in an example.

FIG. 19 illustrates the change in the absorbance at 370 nm for each sample. In the samples that were used as negative controls, namely the sample to which wild-type pG with no introduced K-tag had been added and the sample containing only added K-tag pG, the change in the absorbance at 370 nm (dO.D./min) was 0.03 or less, whereas in the K-tag pG sample in which it is thought that a pG-polymer hybrid had been formed, a large difference of about 0.2 was observed (No. 8). It is thought that this observation indicates that the HRP-labeled IgG was able to bind to the pG on the Z-QG-containing polymer that was not bound to the Anti-OVA IgG, resulting in labeling of the pG-polymer hybrid with a plurality of enzymes. Accordingly, it was assumed that a plurality of pG units existed in the prepared pG-polymer hybrid, namely the K-tag pG had been accumulated on the Z-QG-containing polymer. Further, the fact that strong signals were only observed for the samples in which all three of OVA, Anti-OVA IgG and pG existed confirmed that the result was not due to non-specific adsorption such as physical adsorption, but was rather due to specific binding of the pG to Anti-OVA IgG.

[Evaluation of the Effects of Protein G-Polymer Hybrid Using ELISA Method]

Figure 20:
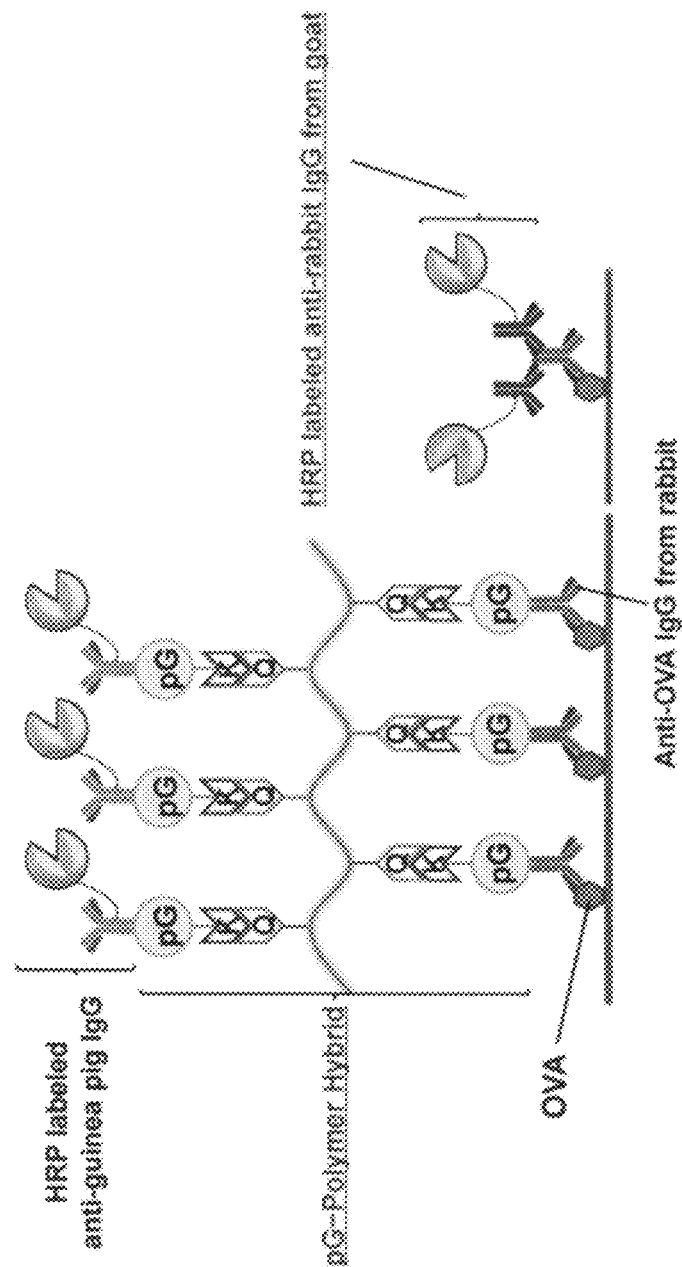
FIG. 20 is a schematic view illustrating ELISA in an example.

In order to illustrate the advantages of the protein G (pG)-polymer hybrid, ELISA was performed using ovalbumin (OVA) as a model antigen. An outline of the ELISA method performed in this test is illustrated in FIG. 20.

The pG-polymer hybrid was prepared in the same manner as above.

A commercially available HRP-labeled anti-rabbit IgG was used as a control.

The procedure for the ELISA operations was the same as described in above. However, in the case of the commercially available HRP-labeled anti-rabbit IgG used as a control, this control was added to the reaction system instead of using the pG-polymer hybrid.

The same tests were performed on a total of 8 samples including the negative control (Table 17).

TABLE 17

|  | 1 | 2 | 3 | 4 | 5 | 6 | 7 | 8 |
|---|---|---|---|---|---|---|---|---|
| Antigen | − | − | − | − | + | + | + | + |
| Primary antibody | − | − | + | + | − | − | + | + |
| Labeled secondary antibody or pG-polymer hybrid | − | + | − | + | − | + | − | + |

Figure 21:
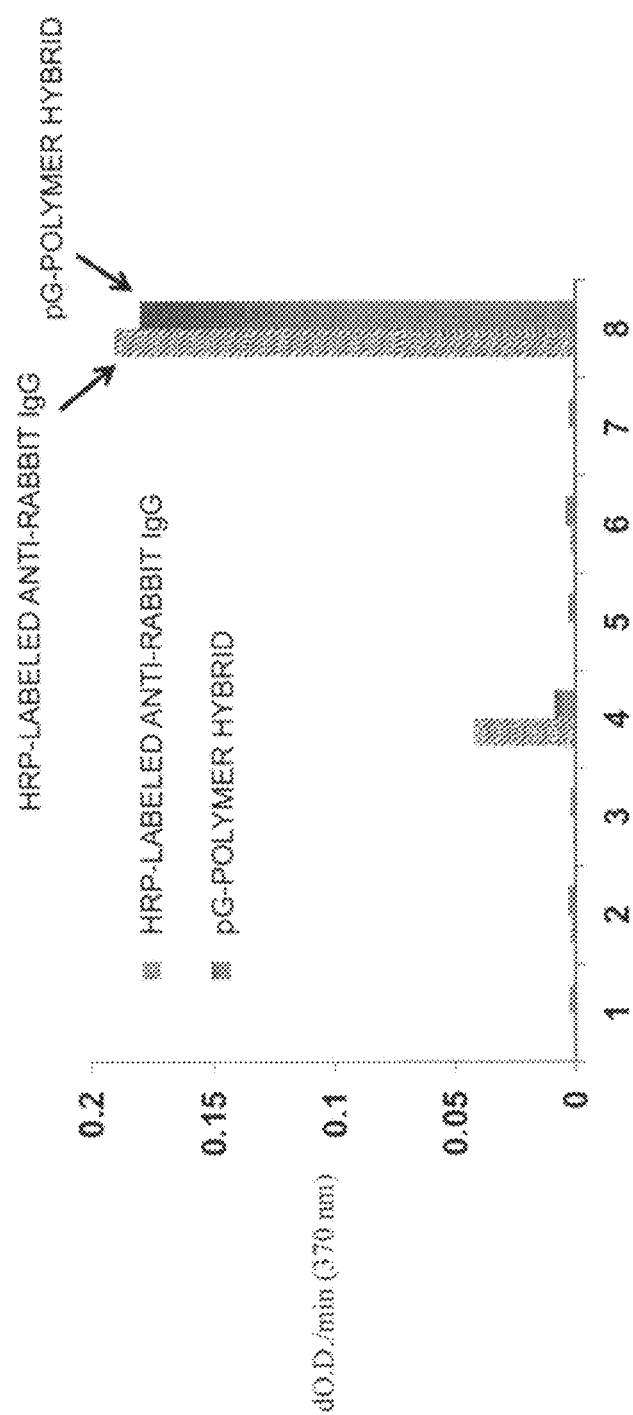
FIG. 21 is a diagram illustrating an ELISA evaluation of a protein G-polymer hybrid.

FIG. 21 illustrates the change in the absorbance (dO.D./min) at 370 nm for each of the samples. The change in absorbance for the pG-polymer hybrid was about 0.18, which was substantially the same change in absorbance as that observed for the commercially available HRP-labeled anti-rabbit IgG (No. 8). But, when the respective negative controls (No. 4) in which the antigen did not exist were compared, the commercially available HRP-labeled anti-rabbit IgG exhibited a background of about 0.042, whereas the pG-polymer hybrid value was less than 0.01, indicating that the background was able to be lowered.

Comparing the results for No. 4 and No. 8, the S/N ratio for the prepared pG-polymer hybrid was about 23, which was considerably higher than the S/N ratio observed for the commercially available HRP-labeled IgG antibody (about 4.6).

Example 2

(Synthesis 2 of Z-QG-EMA)

A 200 mL round-bottom flask was charged with Z-QG-OH (0.51 g, 1.5 mmol), anhydrous N,N-dimethylformamide (anhydrous DMF) (15 mL) and HEMA (0.39 g, 3.0 mmol, 2.0 eq./Z-QG-OH) were added, and the mixture was cooled in ice. Subsequently, DCC (0.37 g, 1.8 mmol, 1.2 eq./Z-QG-OH) and HOBt (0.29 g, 1.9 mmol, 1.3 eq./Z-QG-OH) were added. DMAP (37 mg, 0.30 mmol, 0.21 eq./Z-QG-OH) was then added, the temperature was raised gradually to room temperature, and the mixture was then stirred at 40° C. for 20 hours. The white solid that formed in the reaction solution was removed by suction filtration, and the solvent was then removed by distillation under reduced pressure. The product was dissolved in dimethyl sulfoxide (DMSO), ethyl acetate was used as the organic layer, and the organic layer was washed with a 10% aqueous solution of citric acid and then a 5% aqueous solution of sodium bicarbonate. The organic layer was then washed in a saturated saline solution, and following drying over anhydrous sodium sulfate, the solvent was removed by distillation under reduced pressure, yielding a white powder. Identification of the product was performed by $^1$H-NMR. The product was a white powder (yield: 0.63 g, yield: 93%). In this manner, Z-QG-EMA was able to be recovered by performing only liquid separation operations.

(Synthesis of TEGMA)

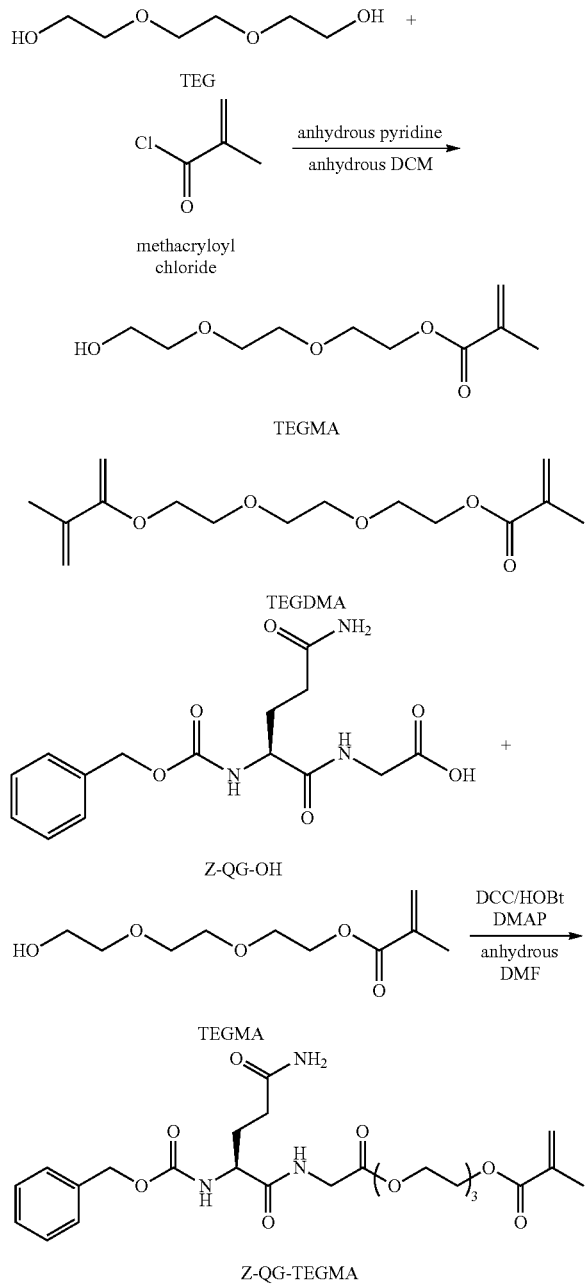

A 300 mL three-neck round-bottom flask was charged with TEG (3.4 mL, 26 mmol) and anhydrous pyridine (2.1 mL, 26 mmol, 1.0 eq./TEG), anhydrous dichloromethane (anhydrous DCM) (80 mL) was added, and the resulting mixture was stirred at room temperature for 30 minutes while undergoing Ar bubbling. The reaction container was then cooled in ice, methacryloyl chloride (2.4 mL, 25 mmol, 0.96 eq./TEG) was added dropwise under an Ar atmosphere, and stirring was continued for 2 hours in the ice bath. The temperature was then gradually raised to room temperature, and following stirring for a further 2 hours under an Ar atmosphere, the solvent was removed by distillation under reduced pressure, and the resulting product was suspended in ethyl acetate. Silica gel was added and a rotary evaporation was performed, thereby adsorbing the product to the silica. Following purification by flash column chromatography (silica gel, ethyl acetate:n-hexane=7:3 (v/v)), the solvent was removed by distillation under reduced pressure, yielding a colorless transparent liquid. The product was identified by $^1$H-NMR.

The product was a colorless transparent liquid (yield: 2.2 g, yield: 69°), and the $^1$H-NMR confirmed that the by-product TEGDMA had been removed. The product was used in the subsequent tests at a purity of 83%.

(Synthesis of Z-QG-TEGMA)

A 50 mL round-bottom flask was charged with Z-QG-OH (0.50 g, 1.5 mmol), anhydrous N,N-dimethylformamide (anhydrous DMF) (15 mL) and TEGMA (0.44 g, 1.7 mmol, 1.1 eq./Z-QG-OH) were added, and the mixture was cooled in ice while undergoing Ar bubbling. Subsequently, DCC (0.37 g, 1.8 mmol, 1.2 eq./Z-QG-OH) and HOBt (0.28 g, 1.8 mmol, 1.2 eq./Z-QG-OH) were added. DMAP (37 mg, 0.30 mmol, 0.21 eq./Z-QG-OH) was then added, the temperature was raised gradually to room temperature, and the mixture was then stirred at 40° C. for 23 hours under an Ar atmosphere. The white solid that formed in the reaction solution was removed by suction filtration, the solvent was then removed by distillation under reduced pressure, and the product was dissolved in ethyl acetate. A 10% aqueous solution of citric acid was added, and the resulting mixture was stirred at room temperature and then extracted twice into ethyl acetate. The organic phase was washed with a 5% aqueous solution of sodium bicarbonate and then washed with a saturated saline solution, and following drying over anhydrous sodium sulfate, the solvent was removed by distillation under reduced pressure, yielding a crude product. This product was dissolved in a mixed methanol/DCM solvent, silica gel was added, and a rotary evaporation was performed, thereby adsorbing the product to the silica. Following purification by flash column chromatography (silica gel, methanol:DCM=1:15 (v/v)), the solvent was removed by distillation under reduced pressure, yielding a white powder. The product was identified by $^1$H-NMR and $^1$H-$^1$H COSY.

The product was a white powder (yield: 0.55 g, yield: 40%), and assignment of the $^1$H-NMR and $^1$H-$^1$H COSY spectra confirmed the production of Z-QG-TEGMA. The solubility was improved compared with Z-QG-EMA, and the product was soluble not only in DMF and DMSO, but also in solvents such as chloroform and DCM.

(Copolymerization of Z-QG Monomer and Acrylamide or MPC)

Z-QG-EMA and Z-QG-TEGMA were selected as the Z-QG monomers, acrylamide and 2-methacryloyloxyethyl phosphorylcholine (MPC) were selected as water-soluble comonomers, and Z-QG polymer syntheses were performed by free radical polymerization. Acrylamide was used as a nonionic monomer. MPC was used as an amphoteric ionic monomer. Further, MPC polymers are known to have a protein non-specific adsorption suppression effect, and it was thought that it may enable suppression of the background and an improvement in the S/N ratio when applied to ELISA.

(Copolymerization with Acrylamide)

Each of the Z-QG monomers (Z-QG-EMA and Z-QG-TEGMA) was copolymerized with Acrylamide.

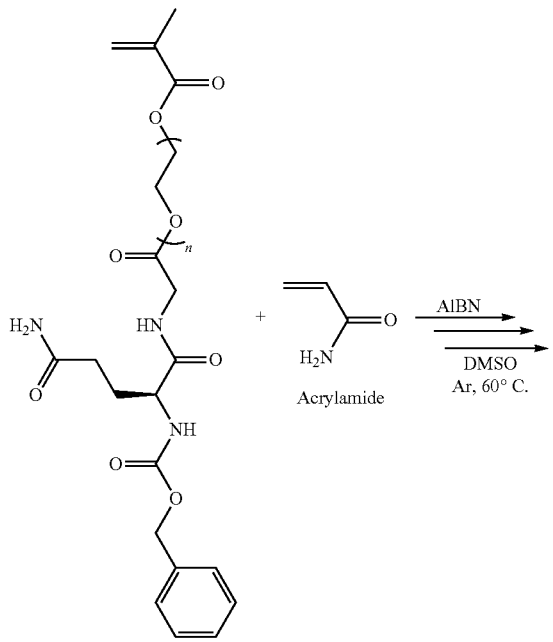

n = 1; Z-QG-EMA
n = 3; Z-QG-TEGMA

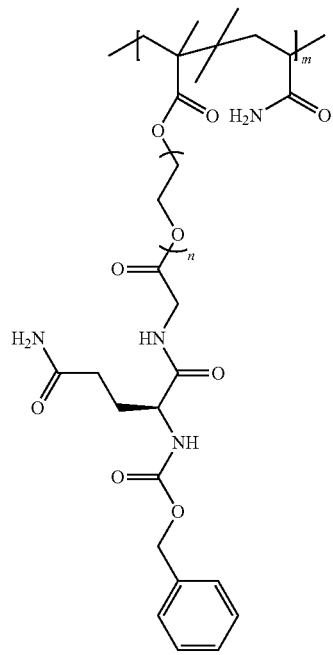

n = 1; Poly(Z-QG-EMA-co-Acrylamide)
n = 3; Poly(Z-QG-TEGMA-co-Acrylamide)

Using the amounts shown in Table 18, each of the reagents was placed in a microtube, and after 30 minutes of Ar bubbling, the microtube was sealed. The microtube was then immersed in an oil bath at 60° C., and stirred for 56 hours (in the case of Z-QG-EMA) or 24 hours (in the case of Z-QG-TEGMA). Each reaction solution was then diluted with Milli-Q water, re-precipitated in cold acetone, and then dried under vacuum. Each of the products was dissolved in Milli-Q water or DMSO/Milli-Q water, and freeze drying was then performed to obtain a white powder. Each product was then identified by $^1$H-NMR.

TABLE 18

| | Reagent | Final concentration |
|---|---|---|
| Z-QG-containing monomer | Z-QG-EMA or Z-QG-TEGMA | 0.04M |
| | Acrylamide | 0.96M |
| Comonomer Initiator | 2,2'-azobis(isobutyronitrile) (AIBN) | 1 mM |

[monomer]=1 M in DMSO

Polymerization temperature=60° C.

Total liquid volume=1.0 mL

The yield of each of the synthesized Z-QG-containing polymers and the copolymer composition calculated from the $^1$H-NMR are shown in Table 19. By using free radical copolymerization, the Z-QG content in the Z-QG-containing polymer could be controlled as desired, and synthesis of the polymers was simple.

TABLE 19

| | Mole fraction (Z-QG/Acrylamide) | | |
|---|---|---|---|
| Sample/abbreviation | in feed | in copolymer | Yield (%) |
| Poly(Z-QG-EMA-co-Acrylamide)/P1 | 0.04/0.96 | 0.041/0.959 | — |
| Poly(Z-QG-TEGMA-co-Acrylamide)/P2 | 0.04/0.96 | 0.036/0.964 | 19 |
| Poly(Z-QG-TEGMA-co-Acrylamide)/P3 | 0.01/0.99 | 0.013/0.987 | 83 |

(Copolymerization with MPC)

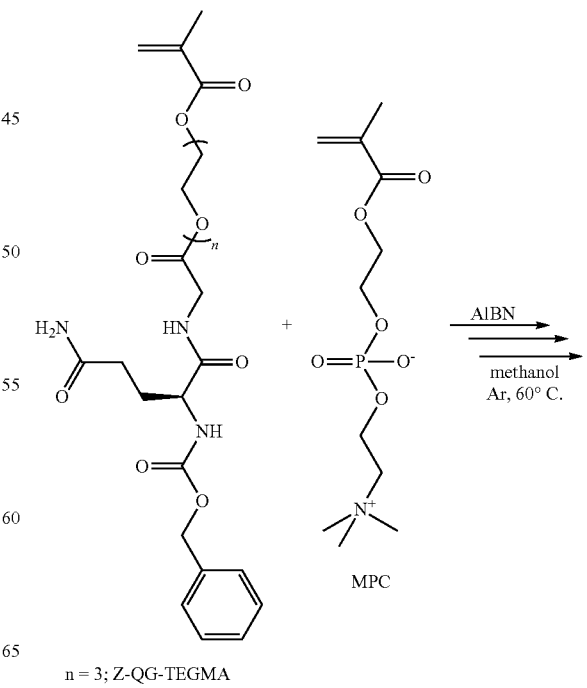

n = 3; Z-QG-TEGMA

-continued

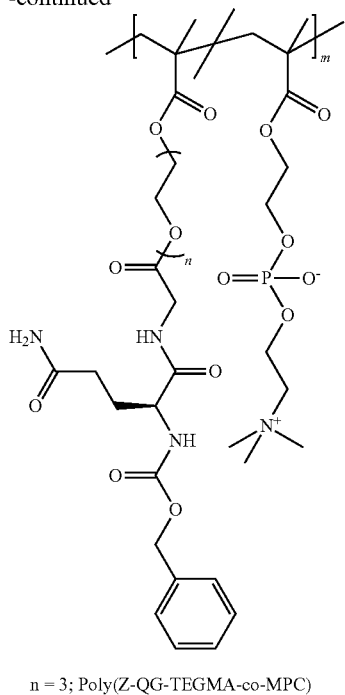

n = 3; Poly(Z-QG-TEGMA-co-MPC)

In order to remove the polymerization inhibitor contained in the MPC, the MPC was decanted several times from cold acetonitrile, and a 2M methanol solution of MPC was then prepared.

Using the amounts shown in Table 20, each of the reagents was placed in a microtube, and after 30 minutes of Ar bubbling, the microtube was sealed. The microtube was then immersed in an oil bath at 60° C. and stirred for 24 hours. The reaction solution was then diluted with methanol, re-precipitated in cold chloroform, and then dried under vacuum. The product was dissolved in Milli-Q water, and freeze drying was then performed to obtain a white powder. The product was then identified by $^1$H-NMR.

TABLE 20

| | Reagent | Final concentration |
|---|---|---|
| Z-QG-containing monomer | Z-QG-TEGMA | 0.04M |
| | MPC | 0.96M |
| Comonomer Initiator | 2,2'-azobis(isobutyronitrile) (AIBN) | 1 mM |

[monomer]=1 M in methanol
Polymerization temperature=60° C.
Total liquid volume=1.0 mL The yield of the synthesized Z-QG-containing polymer and the copolymer composition calculated from the $^1$H-NMR are shown in Table 21.

TABLE 21

| Sample/abbreviation | Mole fraction (Z-QG/MPC) in feed | in copolymer | Yield (%) |
|---|---|---|---|
| Poly(Z-QG-TEGMA-co-MPC)/P4 | 0.04/0.96 | 0.044/0.956 | 17 |

(Preparation of K-Tag EGFP)

For the K-tag EGFP and wild-type EGFP, recombinant proteins prepared in *E. coli* were used. Preparation was performed in accordance with the method disclosed in Protein Lipidation Catalyzed by Microbial Transglutaminase, Hiroki Abe, Masahiro Goto, Noriho Kamiya, Chem. Eur. J. 2011, 17, pp. 14004 to 14008.

(Evaluation of MTG Reactivity of Z-QG-Containing Polymer)

The MTG reactivity of each Z-QG-containing polymer was evaluated using K-tag EGFP.

Figure 22:
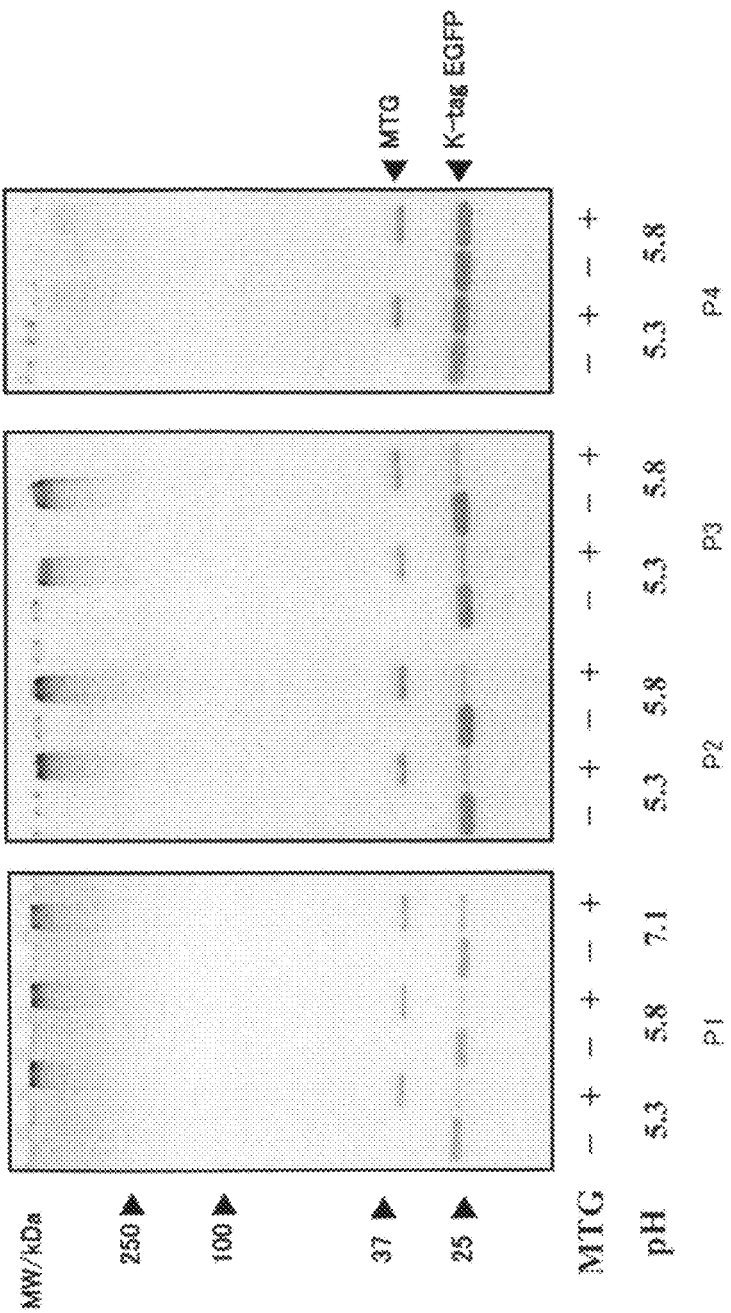
FIG. 22 is a diagram illustrating an evaluation by SDS-PAGE of the MTG reactivity of each Z-QG-containing polymer (P1, P2, P3 and P4) and K-tag EGFP in Example 2.
Figure 30:
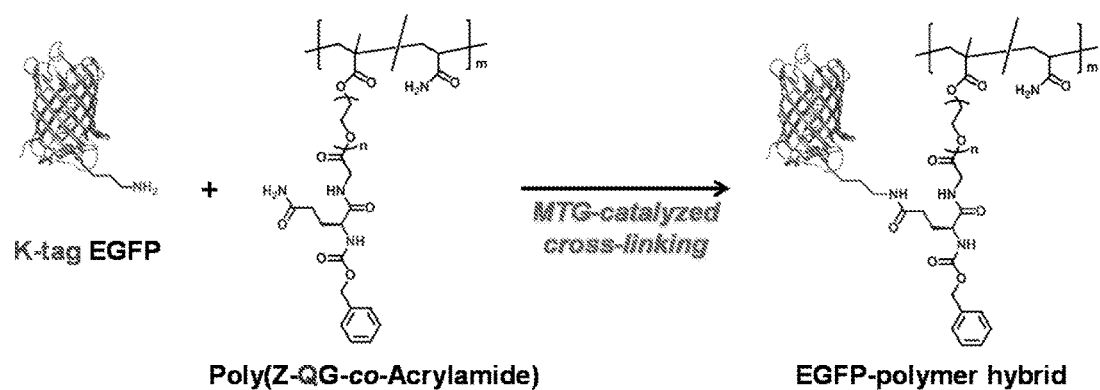
FIG. 30 illustrates a MTG-catalyzed cross-linking reaction for evaluation of MTG reactivity of Z-QG-containing polymer.

The composition of each reagent is shown in Table 22. In terms of the concentration of the Z-QG-containing polymer, preparation was performed with a Z-QG equivalent content, and the Z-QG-containing polymer used and the Z-QG content are shown in Table 23. An MTG-catalyzed reaction as shown in FIG. 30 was performed with the reaction time set to 3 hours and the reaction temperature set to 25° C. N-ethylmaleimide (NEM) was added in an amount sufficient to obtain a final concentration of 1 mM, thereby halting the reaction. SDS-PAGE (10 to 20% gradient gel, electrophoresis conditions: 200 V, 20 mA, 110 min) was then performed, and the products were confirmed by CBB staining (FIG. 22). A sample to which MTG had not been added was tested in a similar manner as a negative control.

TABLE 22

| Reagent | Final concentration |
|---|---|
| Z-QG-containing polymer | 200 μM (Z-QG equivalent) |
| K-tag EGFP | 10 μM |
| MTG | 1.0 unit/ml |

Reaction time=3 hours
Reaction temperature=25° C.
Total liquid volume=50 μL

TABLE 23

| Abbreviation | Copolymer | Z-QG mole fraction |
|---|---|---|
| P1 | Poly(Z-QG-EMA-co-Acrylamide) * | 0.041 |
| P2 | Poly(Z-QG-TEGMA-co-Acrylamide) * | 0.036 |
| P3 | Poly(Z-QG-TEGMA-co-Acrylamide) | 0.013 |
| P4 | Poly(Z-QG-TEGMA-co-MPC) | 0.044 |

P1 and P2 were insoluble in water, and were therefore dissolved in DMSO (final concentration: 2% DMSO (v/v))

Comparing P1 with P2 containing the introduced TEG linker, P2 showed a greater reduction in the K-tag EGFP band intensity, making it clear that the introduction of the TEG linker had improved the MTG reactivity. Further, comparing P2 and P3, which have different Z-QG contents, it was evident that P2, having the higher Z-QG content, had a higher MTG reactivity. Further, almost no reduction in the K-tag EGFP band intensity could be confirmed in P4, but it is thought the fact that a new band was observed at the high-molecular weight side in only the sample containing added MTG suggests that, although minimal, some cross-linking had occurred between the Z-QG-containing polymer and the K-tag EGFP.

It can be said that the above results indicate that by introducing a TEG linker, the MTG reactivity of the Acrylamide copolymers and the MPC copolymer were able to be improved.

Example 3

A poly(Z-QG-TEGMA-co-Acrylamide) (Z-QG content 4%), as Z-QG-containing polymer, synthesized by radical copolymerization of Z-QG-TEGMA and Acrylamide, and K-tag EG were complexed using MTG.

(Preparation of K-Tag EG and CBM-Deficient K-Tag EG)

For the K-tag EG and CBM-deficient K-tag EG, recombinant proteins prepared in E. coli were used. The amino acid sequences of these proteins are shown in SEQ ID NO: 28 and 29 respectively.

Using the genomic DNA of the BAA-629D-5 strain of Thermobifida fusca purchased from ATCC (American Type Culture Collection) as a template, and using primers of SEQ ID NO: 30 and 31 respectively, the full length EG gene was amplified by PCR. Moreover, by subjecting the obtained amplified product to repeated PCR using primer pairs of SEQ ID NO: 30 and 32, and SEQ ID NO: 31 and 33, K-tag was introduced at the downstream of the EG gene. The DNA fragment of the thus obtained full length K-tag EG gene was recombined with the pET22b+ vector using an in-Fusion cloning method (SEQ ID NO: 34).

Furthermore, using the genomic DNA of the BAA-629D-5 strain as a template, and using a primer pair of SEQ ID NO: 35 and 31, PCR was used to amplify the region excluding the secretion signal sequence from the full length EG gene. The obtained amplified fragment was recombined by in-Fusion cloning with a linear pET22b+ vector obtained by performing PCR using SEQ ID NO: 34 as a template and using a primer pair of SEQ ID NO: 36 and 37. This yielded a vector plasmid for K-tag EG expression (SEQ ID NO: 38).

Further, in a similar manner, using a primer pair of SEQ ID NO: 39 and 31, a portion excluding the CBM region from the EG gene was amplified by PCR, and the resulting amplified fragment was recombined with the pET22b+ vector by in-Fusion cloning to obtain a vector plasmid for expressing CBM-deficient K-tag EG (SEQ ID NO: 40).

K-tag EG and CBM-deficient K-tag EG were expressed from the prepared vector plasmids using E. coli (BL21 strain). The vector plasmids were transformed into E. coli (BL21 strain), the E. coli were then subjected to shake-culturing in an LB medium containing ampicillin (100 μg/mL) at 37° C., and when the absorbance at 600 nm reached about 1, isopropyl β-D-1-thiogalactopyranoside was added in an amount sufficient to achieve a final concentration of 0.5 mM. Subsequently, shake-culturing was continued at 25° C. overnight, thus expressing the protein. The thus obtained bacterial cells were collected by centrifugal separation, pulverized by an ultrasonic treatment, subjected to His-tag purification using filtration and an Ni-NTA column, and then dialyzed in PBS, yielding the K-tag EG and CBM-deficient K-tag EG.

(Z-QG-Containing Polymer-K-Tag EG Complex)

The reaction conditions are shown in Table 24. In terms of the concentration of the Z-QG-containing polymer, preparation was performed with a Z-QG equivalent content. The reaction temperature was set to 25° C., samples of the reaction solution were collected 1, 3 and 6 hours after the start of the reaction, a 2× sample buffer was added to each collected sample, and the reaction was halted by heating at 94° C. for 15 minutes. Subsequently, a reaction trace was performed by SDS-polyacrylamide gel electrophoresis (SDS-PAGE), and the image analysis software Image J was used to calculate the reaction rate of the complexed K-tag EG. A sample to which MTG had not been added, and a sample using wild-type EG were tested in a similar manner as negative controls.

TABLE 24

| Reagent | Final concentration |
|---|---|
| Poly(Z-QG-TEGMA-co-Acrylamide) | 200 μM (Z-QG equivalent) |
| Ktag-EG (Tfu0901) | 10 μM |
| MTG | 0.1 unit/ml |
| Phosphate buffer (pH 6.0) | 50 mM |

Reaction time=1, 3, 6 hours

Reaction temperature=25° C.

Total liquid volume=50 μL

Figure 23:
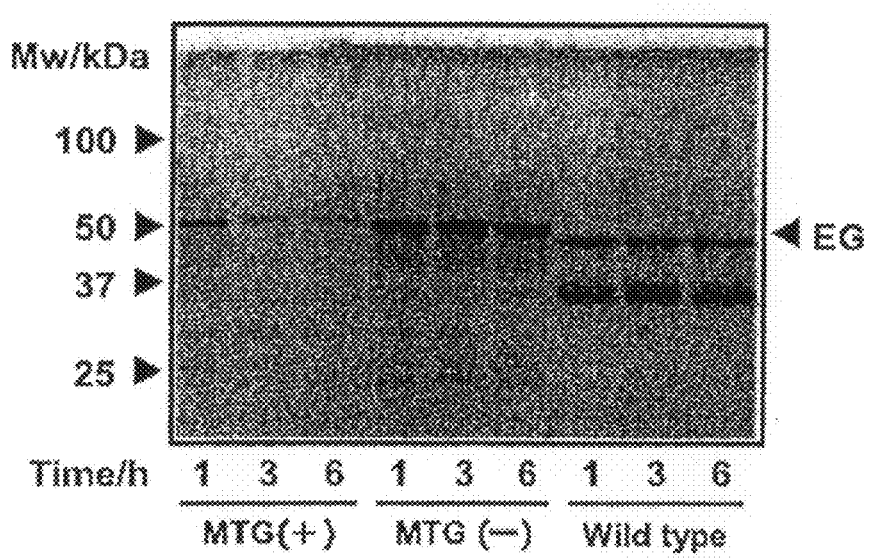
FIG. 23 is a diagram illustrating an evaluation by SDS-PAGE of the MTG reactivity of a Z-QG-containing polymer and K-tag EG in Example 3.

The results of the SDS-PAGE analyses are shown in FIG. 23. The fact that no reduction in band intensity was observed in the two negative control samples confirmed a K-tag-specific cross-linking reaction catalyzed by MTG. The results of image analysis using the image analysis software Image J revealed that the reaction rates after reaction times of 1, 3 and 5 hours were 51%, 91% and 90° respectively.

(Z-QG-Containing Polymer-CBM-Deficient EG Complex)

The Z-QG-containing polymer and CBM-deficient K-tag fused EG (ΔCBM-EG-Ktag) were complexed.

The reaction conditions are shown in Table 25. In terms of the concentration of the Z-QG-containing polymer, preparation was performed with a Z-QG equivalent content. The reaction temperature was set to 25° C., samples of the reaction solution were collected 1, 3 and 6 hours after the start of the reaction, a 2× sample buffer was added to each collected sample, and the reaction was halted by heating at 94° C. for 15 minutes. Subsequently, a reaction trace was performed by SDS-polyacrylamide gel electrophoresis (SDS-PAGE). The thus obtained gel was stained using Coomassie Brilliant Blue (CBB) to confirm the products. Further, an image of the gel was acquired, and the image analysis software Image J was used to calculate the band intensities. Using the ΔCBM-EG-Ktag band intensity of the sample containing no added MTG as a standard, the reduction in the band intensity was calculated as an indicator of the reaction rate of the ΔCBM-EG-Ktag

TABLE 25

| Reagent | Final concentration |
|---|---|
| Poly(Z-QG-TEGMA-co-Acrylamide) | 200 μM (Z-QG equivalent) |
| ΔCBM-EG-Ktag | 10 μM |
| MTG | 0.1 unit/ml |
| Phosphate buffer (pH 6.0) | 50 mM |

Reaction time=1, 3, 6 hours

Reaction temperature=25° C.

Figure 24:
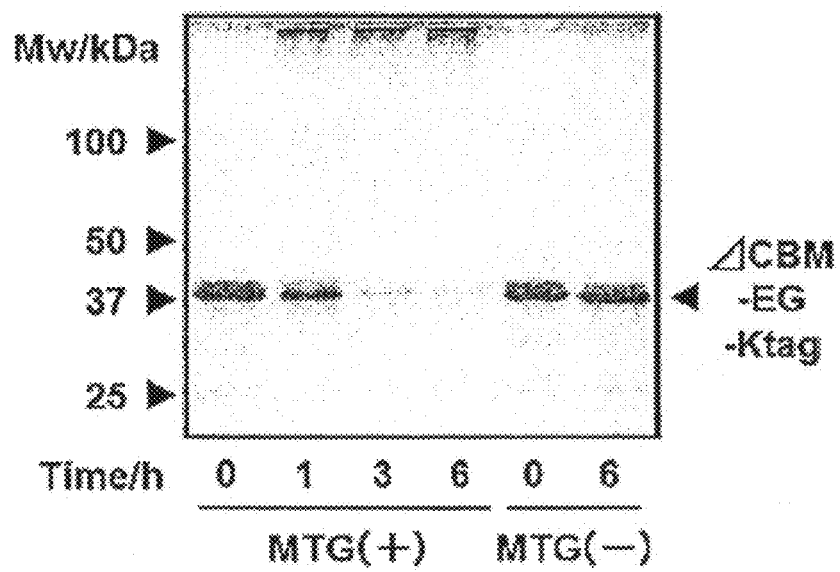
FIG. 24 is a diagram illustrating an evaluation by SDS-PAGE of the MTG reactivity of a Z-QG-containing polymer and ΔCBM-EG-Ktag in Example 3.

The results of the SDS-PAGE analyses are shown in FIG. 24. The reaction rates after reaction times of 1, 3 and 6 hours were 6.7%, 60% and 85% respectively. In this manner, a high reaction rate of 85% had been achieved after reaction for 6 hours.

(Evaluation of Enzyme Activity)

Carboxymethyl cellulose (CMC) was used as a soluble cellulose substrate, and Avicel was used as an insoluble cellulose substrate. Enzyme solutions were added to 50 mM phosphate buffer solutions containing 0.5 wt % of CMC or Avicel that had been heated to 50° C. so that the final concentrations of the various components in the solution were as shown in Table 26, and a hydrolysis reaction was started by stirring with a vortex stirrer.

TABLE 26

| Reagent | Final concentration |
|---|---|
| CMC or Avicel | 0.5 wt % |
| EG | 100 nM |
| BGL | 100 nM |
| Phosphate buffer (pH 7.0) | 50 mM |

Reaction time=5, 24 hours
Reaction temperature=50° C., 1000 rpm

The reaction temperature was set to 50° C., and the reaction time was set to 5 hours for the CMC and 24 hours for the Avicel. Following completion of each reaction, a 100 µL sample was extracted, and the reaction was halted by immersion in an ice bath. Subsequently, the sample was mixed with 100 µL of 3,5-dinitrosalicylic acid (DNS) reagent, and following heating at 99° C. for 5 minutes with rapid stirring, the sample was again cooled in an ice bath. After cooling, the sample was subjected to centrifugal separation (15,000 G, 1 min, 25° C.), the supernatant was added to a 96-well plate, and the absorbance at 540 nm was measured using a plate reader. The amount of reducing sugars in each sample was calculated from the absorbance value. Samples containing only the stand-alone K-tag EG or ΔCBM-EG-Ktag, and samples prepared by physically mixing the K-tag EG or ΔCBM-EG-Ktag with the Z-QG-containing polymer were tested in a similar manner as controls.

Figure 25:
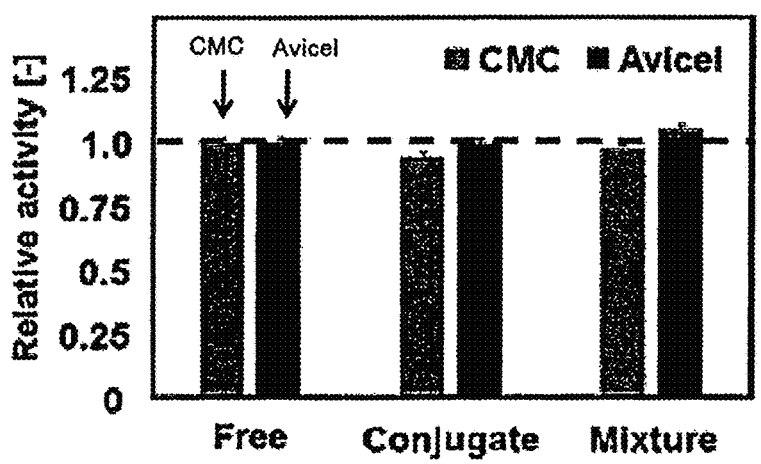
FIG. 25 is a diagram illustrating the results of calculating the amount of reducing sugars when a Z-QG-containing polymer/K-tag EG complex (conjugate) acts upon a cellulose substrate in Example 3.
Figure 26:
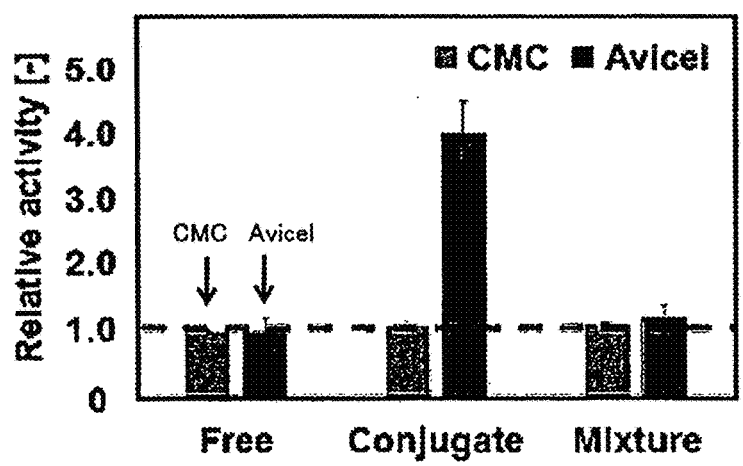
FIG. 26 is a diagram illustrating the results of calculating the amount of reducing sugars when a Z-QG-containing polymer/ΔCBM-EG-Ktag complex (conjugate) acts upon a cellulose substrate in Example 3.

The relative activities of each of the complexes relative to unmodified EG are shown in FIG. 25 and FIG. 26. In the case of the Z-QG-containing polymer/K-tag EG complex, which was prepared using CBM-containing EG that has a high affinity for the substrates, similar activity to the unmodified EG was observed for both substrates. These results suggested that the enzyme activity of each of the accumulated EG enzymes was favorably maintained even after accumulation on the Z-QG-containing polymer.

Further, in the case of the Z-QG-containing polymer/ ΔCBM-EG-Ktag complex, which was prepared using CBM-deficient EG, the activity was similar to the unmodified EG for the soluble substrate. It is known that the existence of CBM has almost no effect on the activity relative to soluble substrates, and therefore it was thought that this result strongly suggested that the enzyme activity of each of the accumulated EG enzymes was able to be maintained. Moreover, the activity relative to the insoluble substrate was about 4 times that of the unmodified EG. It is thought that in the Z-QG-containing polymer/ΔCBM-EG-Ktag complex, although each of the accumulated EG enzymes lacked CBM, the enzyme domains that have slight activity relative to the insoluble substrate interact with the substrate at multiple locations, causing an increase in the apparent affinity for the substrate.

In this manner, the Z-QG-containing polymer/K-tag EG complex which has an extremely strong affinity for the insoluble substrate exhibited similar activity to the unmodified EG, whereas the Z-QG-containing polymer/ΔCBM-EG-Ktag complex which interacted comparatively weakly with the substrate exhibited activity that was about 4 times that of the unmodified ΔCBM-EG. These results suggested that by controlling the affinity of the accumulated enzyme molecules for the substrate, an improvement in the enzyme activity was possible.

As described above, a protein-polymer complex which was capable of detecting a target protein with good sensitivity, and a TGase substrate-containing polymer and a TGase substrate-containing monomer that could be used for obtaining the protein-polymer complex were able to be obtained. Further, a target protein was able to be detected with good sensitivity using the protein-polymer complex. Moreover, by using the protein-polymer complex, the efficiency of the enzyme reaction was able to be improved compared with the stand-alone enzyme.

The invention claimed is:

1. A protein-polymer complex, wherein a protein having a primary amine is bound to the side chain of a glutamine (Gln) residue in a polymer of monomers including an acrylate ester or a methacrylate ester having the glutamine (Gln) residue, represented by the following Formula (1):

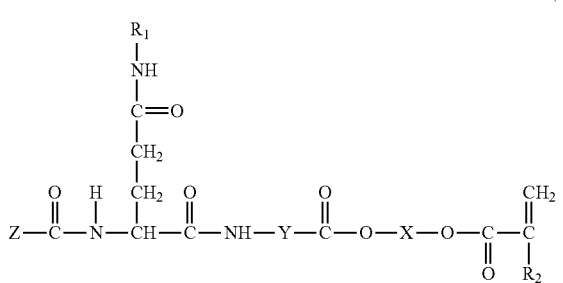

wherein in Formula (1), $R_1$ represents a hydrogen atom or a protective group, $R_2$ represents a hydrogen atom or a methyl group, each of X and Y independently represents an alkylene group having a carbon number of 1 to 48 or an alkenylene group having a carbon number of 2 to 48, which may be substituted with an ethenylene group or $-(C_2H_4O)_n-$ or $-(C_3H_6O)_n-$, wherein n represents the number of repeating units, and Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or L-3,4-dihydroxyphenyl group, and wherein at least one of Y and Z may be independently substituted with an amino acid other than Lys.

2. A method for producing a protein-polymer complex, the method comprising a protein binding step of using a transglutaminase (TGase) to bind a protein having a primary amine to a glutamine (Gln) residue of a polymer of monomers including an acrylate ester or a methacrylate ester having the glutamine (Gln) residue represented by following Formula (1):

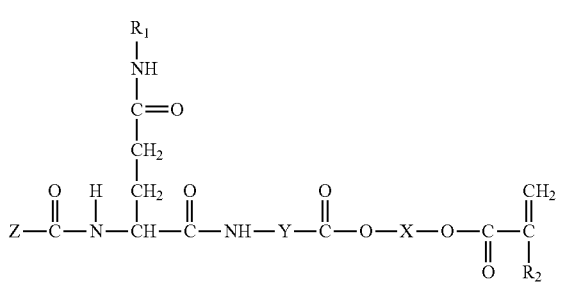

wherein in Formula (1), $R_1$ represents a hydrogen atom or a protective group, $R_2$ represents a hydrogen atom or a methyl group, each of X and Y independently represents an alkylene group having a carbon number of 1 to 48 or an alkenylene group having a carbon number of 2 to 48, which may be substituted with an ethenylene group or $-(C_2H_4O)_n-$ or $-(C_3H_6O)_n-$, wherein n represents the number of repeating units, and Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or L-3,4-dihydroxyphenyl group, and wherein at least one of Y and Z may be independently substituted with an amino acid other than Lys.

3. A method for detecting a protein, the method comprising binding, either directly or indirectly, a protein-polymer complex in which a protein having a primary amine is bound to the side chain of a glutamine (Glu) in a polymer of monomers including an acrylate ester or a methacrylate ester having the glutamine (Gln) residue represented by following Formula (1), and a target protein that exists within a target material, binding a labeling molecule comprising a portion that binds specifically to the protein of the bound protein-polymer complex, and detecting the labeling molecule,

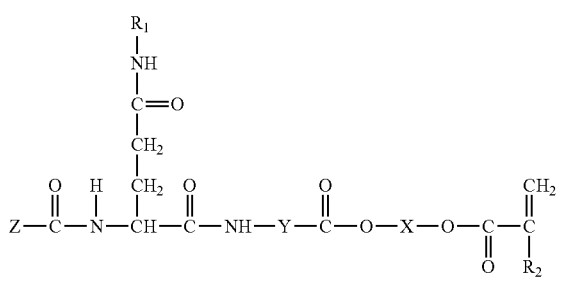

wherein in Formula (1), $R_1$ represents a hydrogen atom or a protective group, $R_2$ represents a hydrogen atom or a methyl group, each of X and Y independently represents an alkylene group having a carbon number of 1 to 48 or an alkenylene group having a carbon number of 2 to 48, which may be substituted with an ethenylene group or $-(C_2H_4O)_n-$ or $-(C_3H_6O)_n-$, wherein n represents the number of repeating units, and Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or L-3,4-dihydroxyphenyl group, and wherein at least one of Y and Z may be independently substituted with an amino acid other than Lys.

* * * * *

SEQUENCE LISTING

```
<160> NUMBER OF SEQ ID NOS: 40

<210> SEQ ID NO 1
<211> LENGTH: 4
<212> TYPE: PRT
<213> ORGANISM: Artificial Sequence
<220> FEATURE:
<223> OTHER INFORMATION: chemically synthesized peptides

<400> SEQUENCE: 1

Leu Leu Gln Gly
1

<210> SEQ ID NO 2
<211> LENGTH: 4
<212> TYPE: PRT
<213> ORGANISM: Artificial Sequence
<220> FEATURE:
<223> OTHER INFORMATION: chemically synthesized peptides

<400> SEQUENCE: 2

Leu Ala Gln Gly
1

<210> SEQ ID NO 3
<211> LENGTH: 4
<212> TYPE: PRT
```

```
<213> ORGANISM: Artificial Sequence
<220> FEATURE:
<223> OTHER INFORMATION: chemically synthesized peptides

<400> SEQUENCE: 3

Leu Gly Gln Gly
1

<210> SEQ ID NO 4
<211> LENGTH: 6
<212> TYPE: PRT
<213> ORGANISM: Artificial Sequence
<220> FEATURE:
<223> OTHER INFORMATION: chemically synthesized peptides

<400> SEQUENCE: 4

Pro Leu Ala Gln Ser His
1               5

<210> SEQ ID NO 5
<211> LENGTH: 8
<212> TYPE: PRT
<213> ORGANISM: Artificial Sequence
<220> FEATURE:
<223> OTHER INFORMATION: chemically synthesized peptides

<400> SEQUENCE: 5

Phe Glu Arg Gln His Met Asp Ser
1               5

<210> SEQ ID NO 6
<211> LENGTH: 11
<212> TYPE: PRT
<213> ORGANISM: Artificial Sequence
<220> FEATURE:
<223> OTHER INFORMATION: chemically synthesized peptides

<400> SEQUENCE: 6

Thr Glu Gln Lys Leu Ile Ser Glu Glu Asp Leu
1               5                   10

<210> SEQ ID NO 7
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 7

Gly Leu Gly Gln Gly Gly Gly
1               5

<210> SEQ ID NO 8
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 8

Gly Phe Gly Gln Gly Gly Gly
1               5

<210> SEQ ID NO 9
<211> LENGTH: 7
<212> TYPE: PRT
<213> ORGANISM: Artificial Sequence
```

```
<220> FEATURE:
<223> OTHER INFORMATION: chemically synthesized peptides

<400> SEQUENCE: 9

Gly Val Gly Gln Gly Gly Gly
1               5

<210> SEQ ID NO 10
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 10

Gly Gly Leu Gln Gly Gly Gly
1               5

<210> SEQ ID NO 11
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 11

Glu Ala Gln Gln Ile Val Met
1               5

<210> SEQ ID NO 12
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 12

Gly Gly Gly Gln Leu Gly Gly
1               5

<210> SEQ ID NO 13
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 13

Gly Gly Gly Gln Val Gly Gly
1               5

<210> SEQ ID NO 14
<211> LENGTH: 7
<212> TYPE: PRT
<213> ORGANISM: Artificial
<220> FEATURE:
<223> OTHER INFORMATION: chemically synthesized peptides

<400> SEQUENCE: 14

Gly Gly Gly Gln Arg Gly Gly
1               5

<210> SEQ ID NO 15
<211> LENGTH: 6
<212> TYPE: PRT
<213> ORGANISM: Artificial Sequence
<220> FEATURE:
```

<223> OTHER INFORMATION: chemically synthesized peptides

<400> SEQUENCE: 15

Gly Gln Gln Gln Leu Gly
1               5

<210> SEQ ID NO 16
<211> LENGTH: 7
<212> TYPE: PRT
<213> ORGANISM: Artificial
<220> FEATURE:
<223> OTHER INFORMATION: chemically synthesized peptides

<400> SEQUENCE: 16

Pro Asn Pro Gln Leu Pro Phe
1               5

<210> SEQ ID NO 17
<211> LENGTH: 7
<212> TYPE: PRT
<213> ORGANISM: Artificial Sequence
<220> FEATURE:
<223> OTHER INFORMATION: chemically synthesized peptides

<400> SEQUENCE: 17

Pro Lys Pro Gln Gln Phe Met
1               5

<210> SEQ ID NO 18
<211> LENGTH: 6
<212> TYPE: PRT
<213> ORGANISM: Artificial
<220> FEATURE:
<223> OTHER INFORMATION: chemically synthesized peptides

<400> SEQUENCE: 18

Met Lys His Lys Gly Ser
1               5

<210> SEQ ID NO 19
<211> LENGTH: 21
<212> TYPE: PRT
<213> ORGANISM: Artificial Sequence
<220> FEATURE:
<223> OTHER INFORMATION: chemically synthesized peptides

<400> SEQUENCE: 19

Gly Ser Gly Met Lys Glu Thr Ala Ala Ala Arg Phe Glu Arg Ala His
1               5                   10                  15

Met Asp Ser Gly Ser
            20

<210> SEQ ID NO 20
<211> LENGTH: 13
<212> TYPE: PRT
<213> ORGANISM: Artificial
<220> FEATURE:
<223> OTHER INFORMATION: chemically synthesized peptides

<400> SEQUENCE: 20

Met Gly Gly Ser Thr Lys His Lys Ile Pro Gly Gly Ser
1               5                   10

<210> SEQ ID NO 21
<211> LENGTH: 5
<212> TYPE: PRT

<210> SEQ ID NO 21
<211> LENGTH: 5
<212> TYPE: PRT
<213> ORGANISM: Artificial Sequence
<220> FEATURE:
<223> OTHER INFORMATION: chemically synthesized peptides

<400> SEQUENCE: 21

Gly Gly Gly Gly Gly
1               5

<210> SEQ ID NO 22
<211> LENGTH: 14
<212> TYPE: PRT
<213> ORGANISM: Artificial
<220> FEATURE:
<223> OTHER INFORMATION: chemically synthesized peptides

<400> SEQUENCE: 22

Met Lys His Lys Gly Ser Gly Gly Gly Ser Gly Gly Gly Ser
1               5                   10

<210> SEQ ID NO 23
<211> LENGTH: 6
<212> TYPE: PRT
<213> ORGANISM: Artificial Sequence
<220> FEATURE:
<223> OTHER INFORMATION: chemically synthesized peptides

<400> SEQUENCE: 23

Met Arg His Lys Gly Ser
1               5

<210> SEQ ID NO 24
<211> LENGTH: 6
<212> TYPE: PRT
<213> ORGANISM: Artificial
<220> FEATURE:
<223> OTHER INFORMATION: chemically synthesized peptides

<400> SEQUENCE: 24

Met Arg Arg Lys Gly Ser
1               5

<210> SEQ ID NO 25
<211> LENGTH: 6
<212> TYPE: PRT
<213> ORGANISM: Artificial
<220> FEATURE:
<223> OTHER INFORMATION: chemically synthesized peptides

<400> SEQUENCE: 25

Met His Arg Lys Gly Ser
1               5

<210> SEQ ID NO 26
<211> LENGTH: 5778
<212> TYPE: DNA
<213> ORGANISM: Artificial Sequence
<220> FEATURE:
<223> OTHER INFORMATION: chemically synthesized DNA

<400> SEQUENCE: 26
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttta gg     180 gttccgattt agtgctttac ggcacctcga ccccaaaaaa cttgattagg gtgatggttc     240

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta aagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg agacaataac cctgataaat gcttcaataa tattgaaaaa ggaagagtat    600
gagtattcaa catttccgtg tcgcccttat ccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gacccgtag aaagatcaa    1620 aggatcttct tgagatcctt ttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag cgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
```

```
gcatgtgtca gaggttttca ccgtcatcac cgaaacgcgc gaggcagctg cggtaaagct      2700
catcagcgtg gtcgtgaagc gattcacaga tgtctgcctg ttcatccgcg tccagctcgt      2760
tgagtttctc cagaagcgtt aatgtctggc ttctgataaa gcgggccatg ttaagggcgg      2820 tttttttcctg tttggtcact gatgcctccg tgtaagggggg atttctgttc atgggggtaa   2880
tgataccgat gaaacgagag aggatgctca cgatacgggt tactgatgat gaacatgccc      2940
ggttactgga acgttgtgag ggtaaacaac tggcggtatg gatgcggcgg gaccagagaa      3000
aaatcactca gggtcaatgc cagcgcttcg ttaatacaga tgtaggtgtt ccacagggta      3060
gccagcagca tcctgcgatg cagatccgga acataatggt gcagggcgct gacttccgcg      3120
tttccagact ttacgaaaca cggaaaccga agaccattca tgttgttgct caggtcgcag      3180
acgttttgca gcagcagtcg cttcacgttc gctcgcgtat cggtgattca ttctgctaac      3240
cagtaaggca accccgccag cctagccggg tcctcaacga caggagcacg atcatgcgca      3300
cccgtggggc cgccatgccg gcgataatgg cctgcttctc gccgaaacgt ttggtggcgg      3360
gaccagtgac gaaggcttga gcgagggcgt gcaagattcc gaataccgca agcgacaggc      3420
cgatcatcgt cgcgctccag cgaaagcggt cctcgccgaa aatgacccag agcgctgccg      3480
gcacctgtcc tacgagttgc atgataaaga agacagtcat aagtgcggcg acgatagtca      3540
tgccccgcgc ccaccggaag gagctgactg ggttgaaggc tctcaagggc atcggtcgag      3600
atcccggtgc ctaatgagtg agctaactta cattaattgc gttgcgctca ctgcccgctt      3660
tccagtcggg aaacctgtcg tgccagctgc attaatgaat cggccaacgc gcggggagag      3720
gcggtttgcg tattgggcgc cagggtggtt tttcttttca ccagtgagac gggcaacagc      3780
tgattgccct tcaccgcctg gccctgagag agttgcagca agcggtccac gctggtttgc      3840
cccagcaggc gaaaatcctg tttgatggtg gttaacggcg ggatataaca tgagctgtct      3900
tcggtatcgt cgtatcccac taccgagata tccgcaccaa cgcgcagccc ggactcggta      3960
atggcgcgca ttgcgcccag cgccatctga tcgttggcaa ccagcatcgc agtgggaacg      4020
atgccctcat tcagcatttg catggtttgt tgaaaaccgg acatggcact ccagtcgcct      4080
tcccgttccg ctatcggctg aatttgattg cgagtgagat atttatgcca gccagccaga      4140
cgcagacgcg ccgagacaga acttaatggg cccgctaaca gcgcgatttg ctggtgaccc      4200
aatgcgacca gatgctccac gcccagtcgc gtaccgtctt catgggagaa ataatactg      4260 ttgatgggtg tctggtcaga gacatcaaga aataacgccg gaacattagt gcaggcagct      4320
tccacagcaa tggcatcctg gtcatccagc ggatagttaa tgatcagccc actgacgcgt      4380
tgcgcgagaa gattgtgcac cgccgcttta caggcttcga cgccgcttcg ttctaccatc      4440
gacaccacca cgctggcacc cagttgatcg gcgcgagatt taatcgccgc gacaatttgc      4500
gacggcgcgt gcagggccag actggaggtg gcaacgccaa tcagcaacga ctgtttgccc      4560
gccagttgtt gtgccacgcg gttgggaatg taattcagct ccgccatcgc cgcttccact      4620
ttttcccgcg ttttcgcaga aacgtggctg gcctggttca ccacgcggga aacggtctga      4680
taagagacac cggcatactc tgcgacatcg tataacgtta ctggtttcac attcaccacc      4740
ctgaattgac tctcttccgg cgctatcat gccataccgc gaaaggtttt gcgccattcg      4800
atggtgtccg ggatctcgac gctctccctt atgcgactcc tgcattagga agcagcccag      4860
tagtaggttg aggccgttga gcaccgccgc cgcaaggaat ggtgcatgca aggagatggc      4920
gcccaacagt cccccggcca cggggcctgc caccataccc acgccgaaac aagcgctcat      4980
```

```
gagcccgaag tggcgagccc gatcttcccc atcggtgatg tcggcgatat aggcgccagc   5040
aaccgcacct gtggcgccgg tgatgccggc cacgatgcgt ccggcgtaga ggatcgagat   5100
ctcgatcccg cgaaattaat acgactcact ataggggaat tgtgagcgga taacaattcc   5160
cctctagaaa taattttgtt taactttaag aaggagatat acatatgact tacaaattgg   5220
tcattaacgg gaaaaccctt aaaggggaaa ccaccactaa ggcggttgac gcggaaacgg   5280
ccgagaaagc gttcaagcag tatgctaacg acaatggtgt tgatggcgtg tggacctatg   5340
atgatgctac aaaaacattt acggtgaccg aaggtggcgg cggttccgat gtcgacaata   5400
agttcaataa agagcagcag aacgccttct gggagattct ccacctcccg aatctgaacg   5460
aggagcagcg taacggtttt attcaatctc tgaaagacga tccgtcacag agcgctaacc   5520
tgctggcaga agcaaaaaaa ttaaatgatg cccaggcgcc gaaaggcggt gggggatccc   5580
tggttcctcg tggttctatg agacacaaag gttccctcga gcaccaccac caccaccact   5640
gagatccggc tgctaacaaa gcccgaaagg aagctgagtt ggctgctgcc accgctgagc   5700
aataactagc ataacccctt ggggcctcta acgggtctt gaggggtttt ttgctgaaag   5760
gaggaactat atccggat                                                 5778
```

<210> SEQ ID NO 27
<211> LENGTH: 145
<212> TYPE: PRT
<213> ORGANISM: Artificial Sequence
<220> FEATURE:
<223> OTHER INFORMATION: chemically synthesized peptides

<400> SEQUENCE: 27

Met Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
            20                  25                  30

Tyr Ala Asn Asp Asn Gly Val Asp Gly Val Trp Thr Tyr Asp Asp Ala
        35                  40                  45

Thr Lys Thr Phe Thr Val Thr Glu Gly Gly Gly Ser Asp Val Asp
    50                  55                  60

Asn Lys Phe Asn Lys Glu Gln Gln Asn Ala Phe Trp Glu Ile Leu His
65                  70                  75                  80

Leu Pro Asn Leu Asn Glu Glu Gln Arg Asn Gly Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Gly Gly Gly Gly Ser Leu Val Pro
        115                 120                 125

Arg Gly Ser Met Arg His Lys Gly Ser Leu Glu His His His His
    130                 135                 140

His
145

<210> SEQ ID NO 28
<211> LENGTH: 454
<212> TYPE: PRT
<213> ORGANISM: Artificial Sequence
<220> FEATURE:
<223> OTHER INFORMATION: chemically synthesized peptides

<400> SEQUENCE: 28

Met Thr Ala Thr Val Thr Lys Glu Ser Ser Trp Asp Asn Gly Tyr Ser

-continued

```
1               5                   10                  15
Ala Ser Val Thr Val Arg Asn Asp Thr Ser Ser Thr Val Ser Gln Trp
            20                  25              30

Glu Val Val Leu Thr Leu Pro Gly Gly Thr Val Ala Gln Val Trp
            35              40                  45

Asn Ala Gln His Thr Ser Ser Gly Asn Ser His Thr Phe Thr Gly Val
        50              55                  60

Ser Trp Asn Ser Thr Ile Pro Pro Gly Gly Thr Ala Ser Phe Gly Phe
65              70                  75                      80

Ile Ala Ser Gly Ser Gly Glu Pro Thr His Cys Thr Ile Asn Gly Ala
                85                  90                  95

Pro Cys Asp Glu Gly Ser Glu Pro Gly Gly Pro Gly Gly Pro Gly Thr
                100                 105                 110

Pro Ser Pro Asp Pro Gly Thr Gln Pro Gly Thr Gly Thr Pro Val Glu
            115                 120                 125

Arg Tyr Gly Lys Val Gln Val Cys Gly Thr Gln Leu Cys Asp Glu His
        130                 135                 140

Gly Asn Pro Val Gln Leu Arg Gly Met Ser Thr His Gly Ile Gln Trp
145                 150                 155                 160

Phe Asp His Cys Leu Thr Asp Ser Ser Leu Asp Ala Leu Ala Tyr Asp
                165                 170                 175

Trp Lys Ala Asp Ile Ile Arg Leu Ser Met Tyr Ile Gln Glu Asp Gly
                180                 185                 190

Tyr Glu Thr Asn Pro Arg Gly Phe Thr Asp Arg Met His Gln Leu Ile
            195                 200                 205

Asp Met Ala Thr Ala Arg Gly Leu Tyr Val Ile Val Asp Trp His Ile
        210                 215                 220

Leu Thr Pro Gly Asp Pro His Tyr Asn Leu Asp Arg Ala Lys Thr Phe
225                 230                 235                 240

Phe Ala Glu Ile Ala Gln Arg His Ala Ser Lys Thr Asn Val Leu Tyr
                245                 250                 255

Glu Ile Ala Asn Glu Pro Asn Gly Val Ser Trp Ala Ser Ile Lys Ser
                260                 265                 270

Tyr Ala Glu Glu Val Ile Pro Val Ile Arg Gln Arg Asp Pro Asp Ser
            275                 280                 285

Val Ile Ile Val Gly Thr Arg Gly Trp Ser Ser Leu Gly Val Ser Glu
        290                 295                 300

Gly Ser Gly Pro Ala Glu Ile Ala Ala Asn Pro Val Asn Ala Ser Asn
305                 310                 315                 320

Ile Met Tyr Ala Phe His Phe Tyr Ala Ala Ser His Arg Asp Asn Tyr
                325                 330                 335

Leu Asn Ala Leu Arg Glu Ala Ser Glu Leu Phe Pro Val Phe Val Thr
            340                 345                 350

Glu Phe Gly Thr Glu Thr Tyr Thr Gly Asp Gly Ala Asn Asp Phe Gln
            355                 360                 365

Met Ala Asp Arg Tyr Ile Asp Leu Met Ala Glu Arg Lys Ile Gly Trp
        370                 375                 380

Thr Lys Trp Asn Tyr Ser Asp Asp Phe Arg Ser Gly Ala Val Phe Gln
385                 390                 395                 400

Pro Gly Thr Cys Ala Ser Gly Gly Pro Trp Ser Gly Ser Ser Leu Lys
                405                 410                 415

Ala Ser Gly Gln Trp Val Arg Ser Lys Leu Gln Ser Tyr Pro Tyr Asp
            420                 425                 430
```

-continued

Val Pro Asp Tyr Ala Gly Gly Ser Met Arg His Lys Gly Ser His
        435                 440                 445

His His His His His His
    450

<210> SEQ ID NO 29
<211> LENGTH: 357
<212> TYPE: PRT
<213> ORGANISM: Artificial Sequence
<220> FEATURE:
<223> OTHER INFORMATION: chemically synthesized peptides

<400> SEQUENCE: 29

Met Asp Glu Gly Ser Glu Pro Gly Gly Pro Gly Gly Pro Gly Thr Pro
1               5                   10                  15

Ser Pro Asp Pro Gly Thr Gln Pro Gly Thr Gly Thr Pro Val Glu Arg
            20                  25                  30

Tyr Gly Lys Val Gln Val Cys Gly Thr Gln Leu Cys Asp Glu His Gly
        35                  40                  45

Asn Pro Val Gln Leu Arg Gly Met Ser Thr His Gly Ile Gln Trp Phe
    50                  55                  60

Asp His Cys Leu Thr Asp Ser Ser Leu Asp Ala Leu Ala Tyr Asp Trp
65                  70                  75                  80

Lys Ala Asp Ile Ile Arg Leu Ser Met Tyr Ile Gln Glu Asp Gly Tyr
                85                  90                  95

Glu Thr Asn Pro Arg Gly Phe Thr Asp Arg Met His Gln Leu Ile Asp
            100                 105                 110

Met Ala Thr Ala Arg Gly Leu Tyr Val Ile Val Asp Trp His Ile Leu
        115                 120                 125

Thr Pro Gly Asp Pro His Tyr Asn Leu Asp Arg Ala Lys Thr Phe Phe
    130                 135                 140

Ala Glu Ile Ala Gln Arg His Ala Ser Lys Thr Asn Val Leu Tyr Glu
145                 150                 155                 160

Ile Ala Asn Glu Pro Asn Gly Val Ser Trp Ala Ser Ile Lys Ser Tyr
                165                 170                 175

Ala Glu Glu Val Ile Pro Val Ile Arg Gln Arg Asp Pro Asp Ser Val
            180                 185                 190

Ile Ile Val Gly Thr Arg Gly Trp Ser Ser Leu Gly Val Ser Glu Gly
        195                 200                 205

Ser Gly Pro Ala Glu Ile Ala Ala Asn Pro Val Asn Ala Ser Asn Ile
    210                 215                 220

Met Tyr Ala Phe His Phe Tyr Ala Ala Ser His Arg Asp Asn Tyr Leu
225                 230                 235                 240

Asn Ala Leu Arg Glu Ala Ser Glu Leu Phe Pro Val Phe Val Thr Glu
                245                 250                 255

Phe Gly Thr Glu Thr Tyr Thr Gly Asp Gly Ala Asn Asp Phe Gln Met
            260                 265                 270

Ala Asp Arg Tyr Ile Asp Leu Met Ala Glu Arg Lys Ile Gly Trp Thr
        275                 280                 285

Lys Trp Asn Tyr Ser Asp Phe Arg Ser Gly Ala Val Phe Gln Pro
    290                 295                 300

Gly Thr Cys Ala Ser Gly Gly Pro Trp Ser Gly Ser Ser Leu Lys Ala
305                 310                 315                 320

Ser Gly Gln Trp Val Arg Ser Lys Leu Gln Ser Tyr Pro Tyr Asp Val
                325                 330                 335

```
Pro Asp Tyr Ala Gly Gly Gly Ser Met Arg His Lys Gly Ser His His
            340                 345                 350

His His His His
        355

<210> SEQ ID NO 30
<211> LENGTH: 38
<212> TYPE: DNA
<213> ORGANISM: Artificial Sequence
<220> FEATURE:
<223> OTHER INFORMATION: chemically synthesized DNA

<400> SEQUENCE: 30
aaggagatat acatatggcg aaatcccccg ccgcccgg                          38

<210> SEQ ID NO 31
<211> LENGTH: 52
<212> TYPE: DNA
<213> ORGANISM: Artificial Sequence
<220> FEATURE:
<223> OTHER INFORMATION: chemically synthesized DNA

<400> SEQUENCE: 31
agcataatct ggaacatcat atggatagga ctggagcttg ctccgcaccc ac          52

<210> SEQ ID NO 32
<211> LENGTH: 54
<212> TYPE: DNA
<213> ORGANISM: Artificial Sequence
<220> FEATURE:
<223> OTHER INFORMATION: chemically synthesized DNA

<400> SEQUENCE: 32
gcccttatga cgcatcgagc cacctccagc ataatctgga acatcatatg gata        54

<210> SEQ ID NO 33
<211> LENGTH: 51
<212> TYPE: DNA
<213> ORGANISM: Artificial Sequence
<220> FEATURE:
<223> OTHER INFORMATION: chemically synthesized DNA

<400> SEQUENCE: 33
gtggtggtgg tggtggtgag agcccttatg acgcatcgag ccacctccag c           51

<210> SEQ ID NO 34
<211> LENGTH: 6819
<212> TYPE: DNA
<213> ORGANISM: Artificial Sequence
<220> FEATURE:
<223> OTHER INFORMATION: chemically synthesized DNA

<400> SEQUENCE: 34
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tcccttagg     180 gttccgattt agtgctttac ggcacctcga ccccaaaaaa cttgattagg gtgatggttc   240
acgtagtggg ccatcgccct gatagacggt ttttcgccct tgacgttgg agtccacgtt   300 ctttaatagt ggactcttgt tccaaactgg aacaacactc aacccatct cggtctattc   360 ttttgattta agggatttt tgccgatttc ggcctattg ttaaaaaatg agctgattta    420
```

| | | | | | |
|---|---|---|---|---|---|
| acaaaaattt | aacgcgaatt | ttaacaaaat | attaacgttt | acaatttcag | gtggcacttt | 480 |
| tcggggaaat | gtgcgcggaa | cccctatttg | tttattttc | taaatacatt | caaatatgta | 540 |
| tccgctcatg | agacaataac | cctgataaat | gcttcaataa | tattgaaaaa | ggaagagtat | 600 |
| gagtattcaa | catttccgtg | tcgcccttat | tccctttttt | gcggcatttt | gccttcctgt | 660 |
| ttttgctcac | ccagaaacgc | tggtgaaagt | aaaagatgct | gaagatcagt | tgggtgcacg | 720 |
| agtgggttac | atcgaactgg | atctcaacag | cggtaagatc | cttgagagtt | ttcgccccga | 780 |
| agaacgtttt | ccaatgatga | gcacttttaa | agttctgcta | tgtggcgcgg | tattatcccg | 840 |
| tattgacgcc | gggcaagagc | aactcggtcg | ccgcatacac | tattctcaga | atgacttggt | 900 |
| tgagtactca | ccagtcacag | aaaagcatct | tacggatggc | atgacagtaa | gagaattatg | 960 |
| cagtgctgcc | ataaccatga | gtgataaac | tgcggccaac | ttacttctga | caacgatcgg | 1020 |
| aggaccgaag | gagctaaccg | cttttttgca | caacatgggg | gatcatgtaa | ctcgccttga | 1080 |
| tcgttgggaa | ccggagctga | atgaagccat | accaaacgac | gagcgtgaca | ccacgatgcc | 1140 |
| tgcagcaatg | gcaacaacgt | tgcgcaaact | attaactggc | gaactactta | ctctagcttc | 1200 |
| ccggcaacaa | ttaatagact | ggatggaggc | ggataaagtt | gcaggaccac | ttctgcgctc | 1260 |
| ggcccttccg | gctggctggt | ttattgctga | taaatctgga | gccggtgagc | gtgggtctcg | 1320 |
| cggtatcatt | gcagcactgg | ggccagatgg | taagccctcc | cgtatcgtag | ttatctacac | 1380 |
| gacggggagt | caggcaacta | tggatgaacg | aaatagacag | atcgctgaga | taggtgcctc | 1440 |
| actgattaag | cattggtaac | tgtcagacca | agtttactca | tatatacttt | agattgattt | 1500 |
| aaaacttcat | ttttaattta | aaaggatcta | ggtgaagatc | cttttgata | atctcatgac | 1560 |
| caaaatccct | taacgtgagt | tttcgttcca | ctgagcgtca | gaccccgtag | aaaagatcaa | 1620 |
| aggatcttct | tgagatcctt | tttttctgcg | cgtaatctgc | tgcttgcaaa | caaaaaaacc | 1680 |
| accgctacca | gcggtggttt | gtttgccgga | tcaagagcta | ccaactcttt | ttccgaaggt | 1740 |
| aactggcttc | agcagagcgc | agataccaaa | tactgtcctt | ctagtgtagc | cgtagttagg | 1800 |
| ccaccacttc | aagaactctg | tagcaccgcc | tacatacctc | gctctgctaa | tcctgttacc | 1860 |
| agtggctgct | gccagtggcg | ataagtcgtg | tcttaccggg | ttggactcaa | gacgatagtt | 1920 |
| accggataag | gcgcagcggt | cgggctgaac | ggggggttcg | tgcacacagc | ccagcttgga | 1980 |
| gcgaacgacc | tacaccgaac | tgagatacct | acagcgtgag | ctatgagaaa | gcgccacgct | 2040 |
| tcccgaaggg | agaaaggcgg | acaggtatcc | ggtaagcggc | agggtcggaa | caggagagcg | 2100 |
| cacgagggag | cttccagggg | gaaacgcctg | gtatctttat | agtcctgtcg | ggtttcgcca | 2160 |
| cctctgactt | gagcgtcgat | ttttgtgatg | ctcgtcaggg | gggcggagcc | tatggaaaaa | 2220 |
| cgccagcaac | gcggcctttt | tacggttcct | ggccttttgc | tggccttttg | ctcacatgtt | 2280 |
| ctttcctgcg | ttatcccctg | attctgtgga | taaccgtatt | accgcctttg | agtgagctga | 2340 |
| taccgctcgc | cgcagccgaa | cgaccgagcg | cagcgagtca | gtgagcgagg | aagcggaaga | 2400 |
| gcgcctgatg | cggtattttc | tccttacgca | tctgtgcggt | atttcacacc | gcatatatgg | 2460 |
| tgcactctca | gtacaatctg | ctctgatgcc | gcatagttaa | gccagtatac | actccgctat | 2520 |
| cgctacgtga | ctgggtcatg | gctgcgcccc | gacacccgcc | aacacccgct | gacgcgccct | 2580 |
| gacgggcttg | tctgctcccg | gcatccgctt | acagacaagc | tgtgaccgtc | tccgggagct | 2640 |
| gcatgtgtca | gaggttttca | ccgtcatcac | cgaaacgcgc | gaggcagctg | cggtaaagct | 2700 |
| catcagcgtg | gtcgtgaagc | gattcacaga | tgtctgcctg | ttcatccgcg | tccagctcgt | 2760 |
| tgagtttctc | cagaagcgtt | aatgtctggc | ttctgataaa | gcgggccatg | ttaagggcgg | 2820 |

```
tttttttcctg tttggtcact gatgcctccg tgtaagggggg atttctgttc atggggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat attttatgcca gccagccaga    4140 cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
gccagttgtt gtgccacgcg gttgggaatg taattcagct ccgccatcgc cgcttccact    4620 tttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg cgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact ataggggaat tgtgagcgga taacaattcc    5160
```

```
cctctagaaa taattttgtt taactttaag aaggagatat acatatggcg aaatcccccg    5220
ccgcccggaa gggcggccct ccggtcgctg tcgcggtgac cgcggccctc gccctgctga    5280
tcgcgctcct ctccccgga gtcgcgcagg ccgccggtct caccgccaca gtcaccaaag    5340
aatcctcgtg ggacaacggc tactccgcgt ccgtcaccgt ccgcaacgac acctcgagca    5400
ccgtctccca gtgggaggtc gtcctcaccc tgcccggcgg cactacagtg gcccaggtgt    5460
ggaacgccca gcacaccagc agcggcaact cccacacctt caccggggtt tcctggaaca    5520
gcaccatccc gcccggaggc accgcctcct tcggcttcat cgcttccggc agcggcgaac    5580
ccacccactg caccatcaac ggcgcccct gcgacgaagg ctccgagccg gcggccccg    5640 gcggtcccgg aaccccctcc cccgaccccg gcacgcagcc cggcaccggc accccggtcg    5700
agcggtacgg caaagtccag gtctgcggca cccagctctg cgacgagcac ggcaacccgg    5760
tccaactgcg cggcatgagc acccacgca tccagtggtt cgaccactgc ctgaccgaca    5820
gctcgctgga cgccctggcc tacgactgga aggccgacat catccgcctg tccatgtaca    5880
tccaggaaga cggctacgag accaacccgc gcggcttcac cgaccggatg caccagctca    5940
tcgacatggc cacggcgcgc ggcctgtacg tgatcgtgga ctggcacatc ctcaccccgg    6000
gcgatcccca ctacaacctg gaccgggcca agaccttctt cgcggaaatc gcccagcgcc    6060
acgccagcaa gaccaacgtg ctctacgaga tcgccaacga acccaacgga gtgagctggg    6120
cctccatcaa gagctacgcc gaagaggtca tcccggtgat ccgccagcgc gacccccgact    6180 cggtgatcat cgtgggcacc ccgcggctggt cgtcgctcgg cgtctccgaa ggctccggcc    6240
ccgccgagat cgcggccaac ccggtcaacg cctccaacat catgtacgcc ttccacttct    6300
acgcggcctc gcaccgcgac aactacctca cgcgctgcg tgaggcctcc gagctgttcc    6360
cggtcttcgt caccgagttc ggcaccgaga cctacaccgg tgacgcgcc aacgacttcc    6420 agatggccga ccgctacatc gacctgatgg cggaacggaa gatcgggtgg accaagtgga    6480
actactcgga cgacttccgt tccggcgcgg tcttccagcc gggcacctgc gcgtccggcg    6540
gcccgtggag cggttcgtcg ctgaaggcgt ccggacagtg ggtgcggagc aagctccagt    6600
cctatccata tgatgttcca gattatgctg gaggtggctc gatgcgtcat aagggctctc    6660
accaccacca ccaccaccac tgagatccgg ctgctaacaa agcccgaaag gaagctgagt    6720
tggctgctgc caccgctgag caataactag cataaccccct tggggcctct aaacgggtct    6780 tgagggggttt tttgctgaaa ggaggaacta tatccggat                          6819

<210> SEQ ID NO 35
<211> LENGTH: 42
<212> TYPE: DNA
<213> ORGANISM: Artificial Sequence
<220> FEATURE:
<223> OTHER INFORMATION: chemically synthesized DNA

<400> SEQUENCE: 35
ggagatatac atatgaccgc cacagtcacc aaagaatcct cg                        42

<210> SEQ ID NO 36
<211> LENGTH: 50
<212> TYPE: DNA
<213> ORGANISM: Artificial Sequence
<220> FEATURE:
<223> OTHER INFORMATION: chemically synthesized DNA

<400> SEQUENCE: 36
catatgtata tctccttctt aaagttaaac aaaattattt ctagagggga              50
```

<210> SEQ ID NO 37
<211> LENGTH: 41
<212> TYPE: DNA
<213> ORGANISM: Artificial Sequence
<220> FEATURE:
<223> OTHER INFORMATION: chemically synthesized DNA

<400> SEQUENCE: 37
tatccatatg atgttccaga ttatgctgga ggtggctcga t					41

<210> SEQ ID NO 38
<211> LENGTH: 6705
<212> TYPE: DNA
<213> ORGANISM: Artificial Sequence
<220> FEATURE:
<223> OTHER INFORMATION: chemically synthesized DNA

<400> SEQUENCE: 38

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcggggggc tcccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta tagggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg agacaataac cctgataaat gcttcaataa tattgaaaaa ggaagagtat | 600 |
| gagtattcaa catttccgtg tcgcccttat tccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt ttcgccccga | 780 |
| agaacgtttt ccaatgatga gcacttttaa agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca acatggggg atcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacggggagt caggcaacta tggatgaacg aaatagacag atcgctgaga taggtgcctc | 1440 |
| actgattaag cattggtaac tgtcagacca agtttactca tatatacttt agattgattt | 1500 |
| aaaacttcat ttttaattta aaaggatcta ggtgaagatc ctttttgata atctcatgac | 1560 |
| caaaatccct taacgtgagt tttcgttcca ctgagcgtca gaccccgtag aaaagatcaa | 1620 |
| aggatcttct tgagatcctt tttttctgcg cgtaatctgc tgcttgcaaa caaaaaaacc | 1680 |

```
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcc agcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca acccgccag cctagccggg tcctcaacga caggagcacg atcatgcgca    3300
cccgtggggc cgccatgccg gcgataatgg cctgcttctc gccgaaacgt tggtggcgg    3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
```

```
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt taactttaag aaggagatat acatatgacc gccacagtca    5220
ccaaagaatc ctcgtgggac aacggctact ccgcgtccgt caccgtcgc aacgacacct    5280 cgagcaccgt ctcccagtgg gaggtcgtcc tcaccctgcc cggcggcact acagtggccc    5340
aggtgtggaa cgcccagcac accagcagcg gcaactccca caccttcacc ggggtttcct    5400
ggaacagcac catcccgccc ggaggcaccg cctccttcgg cttcatcgct tccggcagcg    5460
gcgaacccac ccactgcacc atcaacggcg cccctgcga cgaaggctcc gagccgggcg    5520
gccccggcgg tcccggaacc ccctcccccg acccggcac gcagcccggc accggcaccc    5580
cggtcgagcg gtacggcaaa gtccaggtct gcggcaccca gctctgcgac gagcacggca    5640
acccggtcca actgcgcggc atgagcaccc acggcatcca gtggttcgac cactgcctga    5700
ccgacagctc gctggacgcc ctggcctacg actggaaggc cgacatcatc cgcctgtcca    5760
tgtacatcca ggaagacggc tacgagacca acccgcgcgg cttcaccgac cggatgcacc    5820
agctcatcga catggccacg gcgcgcggcc tgtacgtgat cgtggactgg cacatcctca    5880 cccccgggcga tccccactac aacctggacc gggccaagac cttcttcgcg gaaatcgccc    5940
agcgccacgc cagcaagacc aacgtgctct acgagatcgc caacgaaccc aacggagtga    6000
gctgggcctc catcaagagc tacgccgaag aggtcatccc ggtgatccgc cagcgcgacc    6060
ccgactcggt gatcatcgtg ggcacccgcg gctggtcgtc gctcggcgtc tccgaaggct    6120 ccggcccccgc cgagatcgcg gccaacccgg tcaacgcctc caacatcatg tacgccttcc    6180
acttctacgc ggcctcgcac cgcgacaact acctcaacgc gctgcgtgag gcctccgagc    6240
tgttcccggt cttcgtcacc gagttcggca ccgagaccta caccggtgac ggcgccaacg    6300
acttccagat ggccgaccgc tacatcgacc tgatggcgga acggaagatc gggtggacca    6360
agtggaacta ctcggacgac ttccgttccg gcgcggtctt ccagccgggc acctgcgcgt    6420
```

| | |
|---|---|
| ccggcggccc gtggagcggt tcgtcgctga aggcgtccgg acagtgggtg cggagcaagc | 6480 |
| tccagtccta tccatatgat gttccagatt atgctggagg tggctcgatg cgtcataagg | 6540 |
| gctctcacca ccaccaccac caccactgag atccggctgc taacaaagcc cgaaaggaag | 6600 |
| ctgagttggc tgctgccacc gctgagcaat aactagcata ccccttggg gcctctaaac | 6660 |
| gggtcttgag gggttttttg ctgaaaggag gaactatatc cggat | 6705 |

<210> SEQ ID NO 39
<211> LENGTH: 38
<212> TYPE: DNA
<213> ORGANISM: Artificial Sequence
<220> FEATURE:
<223> OTHER INFORMATION: chemically synthesized DNA

<400> SEQUENCE: 39

| | |
|---|---|
| ggagatatac atatggacga aggctccgag ccgggcgg | 38 |

<210> SEQ ID NO 40
<211> LENGTH: 6414
<212> TYPE: DNA
<213> ORGANISM: Artificial Sequence
<220> FEATURE:
<223> OTHER INFORMATION: chemically synthesized DNA

<400> SEQUENCE: 40

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc aaccctatct cggtctattc | 360 |
| ttttgattta agggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgcccttat tccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt ttcgccccga | 780 |
| agaacgtttt ccaatgatga gcacttttaa agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca caacatgggg gatcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacggggagt caggcaacta tggatgaacg aaatagacag atcgctgaga taggtgcctc | 1440 |

```
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacgttcct ggccttttgc tggccttttg ctcacatgtt    2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt tggtggcgg    3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
```

```
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatcccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt taactttaag aaggagatat acatatggac gaaggctccg    5220
agccgggcgg ccccggcggt cccggaaccc cctcccccga ccccggcacg cagcccggca    5280
ccggcacccc ggtcgagcgg tacggcaaag tccaggtctg cggcacccag ctctgcgacg    5340
agcacggcaa cccggtccaa ctgcgcggca tgagcaccca cggcatccag tggttcgacc    5400
actgcctgac cgacagctcg ctggacgccc tggcctacga ctggaaggcc gacatcatcc    5460
gcctgtccat gtacatccag gaagacggct acgagaccaa cccgcgcggc ttcaccgacc    5520
ggatgcacca gctcatcgac atggccacgg cgcgcggcct gtacgtgatc gtggactggc    5580
acatcctcac cccgggcgat ccccactaca acctggaccg ggccaagacc ttcttcgcgg    5640
aaatcgccca gcgccacgcc agcaagacca acgtgctcta cgagatcgcc aacgaaccca    5700
acggagtgag ctgggcctcc atcaagagct acgccgaaga ggtcatcccg gtgatccgcc    5760
agcgcgaccc cgactcggtg atcatcgtgg gcacccgcgg ctggtcgtcg ctcggcgtct    5820
ccgaaggctc cggccccgcc gagatcgcgg ccaacccggt caacgcctcc aacatcatgt    5880
acgccttcca cttctacgcg gcctcgcacc gcgacaacta cctcaacgcg ctgcgtgagg    5940
cctccgagct gttcccggtc ttcgtcaccg agttcggcac cgagacctac accggtgacg    6000
gcgccaacga cttccagatg gccgaccgct acatcgacct gatggcggaa cggaagatcg    6060
ggtggaccaa gtggaactac tcggacgact tccgttccgg cgcggtcttc cagccgggca    6120
cctgcgcgtc cggcggcccg tggagcggtt cgtcgctgaa ggcgtccgga cagtgggtgc    6180
```

-continued

```
ggagcaagct ccagtcctat ccatatgatg ttccagatta tgctggaggt ggctcgatgc    6240
gtcataaggg ctctcaccac caccaccacc accactgaga tccggctgct aacaaagccc    6300
gaaaggaagc tgagttggct gctgccaccg ctgagcaata actagcataa ccccttgggg    6360
cctctaaacg ggtcttgagg ggttttttgc tgaaaggagg aactatatcc ggat          6414
```